United States Patent [19]
Rice et al.

[11] Patent Number: 6,040,504
[45] Date of Patent: Mar. 21, 2000

[54] COTTON PROMOTER

[75] Inventors: Douglas Rice, Durham; Nadine Carozzi, Raleigh, both of N.C.; David M. Anderson, Altadena, Calif.; Kanniah Rajasekaran, Sierra Madre, Calif.; Thirumale S. Rangan, Pasadena, Calif.; Richard Yenofsky, Arcadia, Calif.; Richard Lotstein, Durham, N.C.

[73] Assignee: Novartis Finance Corporation, New York, N.Y.

[21] Appl. No.: 09/021,203

[22] Filed: Feb. 10, 1998

Related U.S. Application Data

[63] Continuation of application No. 08/218,697, Mar. 28, 1994, which is a continuation of application No. 07/759,969, Sep. 16, 1991, abandoned, which is a continuation of application No. 07/274,452, Nov. 18, 1988, abandoned, which is a continuation-in-part of application No. 07/122,209, Nov. 18, 1987, abandoned.

[51] Int. Cl.[7] .............................. A01H 5/00; C07H 21/04; C12N 1/21; C12N 5/14; C12N 15/82
[52] U.S. Cl. .................. 800/314; 435/252.3; 435/320.1; 435/419; 536/23.1; 536/24.1; 800/298
[58] Field of Search .................. 536/24.1, 23.71, 536/23.1; 435/320.1, 252.3, 419; 800/298, 314

[56] References Cited

PUBLICATIONS

Herrera–Estrella L, et al. "Light–inducible and chloroplast–associated expression of a chimaeric gene introduced into Nicotiana tabacum using a Ti plasmid vector," Nature 310: 115–120, Jul. 1984.

Benfey, PN, et al. "The cauliflower mosaic virus 35S promoter: Combinatorial regulation of transcription in plants." Science 250: 959–966, Nov. 1990.

Kim Y, et al. "A 20 nucleotide upstream element is essential for the nopaline synthase (nos) promoter activity." Plant Mol. Biol. 24: 105–117, 1994.

*Primary Examiner*—Lynette R. F. Smith
*Assistant Examiner*—Amy J. Nelson
*Attorney, Agent, or Firm*—J. Timothy Meigs; Gary M. Pace; Thomas Hoxie

[57] ABSTRACT

A promoter isolated from a cotton gene encoding the small subunit of ribulose bisphosphate carboxylase is described. The isolated promoter is operably linked to a coding sequence of interest to make a chimeric gene.

15 Claims, 26 Drawing Sheets

```
  1 CTACTAGCAATGGCTTCCTCAATGATCTCATCGGCTACCATTGCCACTGCCTCTCCGGCA  60
    ------+---------+---------+---------+---------+---------+
    GATGATCGTTACCGAAGGAGTTACTAGAGTAGCCGATGGTAACGGTGACGGAGAGCCCGT

L  L  A  M  A  S  S  M  I  S  S  A  T  I  A  T  A  S  P  A

61 CAGGCTAACATGGTCGCTCCTTTCACCGGCCCTCAAGTCTCTGCCTCTGCTTTCCCAGTCATC 120
    ------+---------+---------+---------+---------+---------+
    GTCCGATTGTACCAGCGAGGAAAGTGGCCGGGAGTTCAGAGACGGAGACGAAAGGGTCAGTAG

Q  A  N  M  V  A  P  F  T  G  L  K  S  A  S  A  F  P  V  I

121 AGGAAGGCCAACAACGACATTACTTCTCTCGCAAGCAATGGGGGCAGAGTGCAATGC
    ------+---------+---------+---------+---------+---------+
    TCCTTCCGGTTGTTGCTGTAATGAAGAGAGCGTTCGTTACCCCGTCTCACGTTACG

```
        AAGCAGTAATAGCAATGGCCTCCTCCTCCATGATCTCATCGGCAACCATTGCCACCGTGAACT
    1   ----------+---------+---------+---------+---------+---------+   60
        TTCGTCATTATCGTTACCGGAGGAGGAGTACTAGAGTAGCCGTTGGTAACGGTGCCACTTGA

A  V  I  A  M  A  S  S  M  I  S  S  A  T  I  A  T  V  N  C

GCTCCTCCCCGGCACAGGCCAACATGGTGCCCCTTCACCGGCCTCAAGTCTGCCTCTG
   61   ----------+---------+---------+---------+---------+---------+  120
        CGAGGAGGGGCCGTGTCCGGTTGTACCACGGGGAAGTGGCCGGAGTTCAGACGGAGAC

S  S  P  A  Q  A  N  M  V  A  P  F  T  G  L  K  S  A  S  A

CTTTCCCAGTCACTAGGAAGGCCAACAACGACATCACTTCTCTTGCAAGCAATGGTGGGA
  121   ----------+---------+---------+---------+---------+---------+  180
        GAAAGGGTCAGTGATCCTTCCGGTTGTTGCTGTAGTGAAGAGAACGTTCGTTACCACCCT

F  P  V  T  R  K  A  N  N  D  I  T  S  L  A  S  N  G  G  R

GAGTGCAATGC
  181   ----------+
        CTCACGTTACG

COTTON PROMOTER

This application is a continuation of U.S. Ser. No. 08/218,697, filed Mar. 28, 1994, which is a continuation of U.S. Ser. No. 07/759,969, filed Sep. 16, 1991, now abandoned, which is a continuation of U.S. Ser. No. 07/274,452, filed Nov. 18, 1988, now abandoned, which is a continuation-in-part of U.S. Ser. No. 07/122,209, filed Nov. 18, 1987, now abandoned.

BACKGROUND OF THE INVENTION

The present invention is directed to a chimeric gene that expresses in cotton cells insecticides having substantially the insect toxicity properties of the crystal protein produced by *Bacillus thuringiensis*.

*Bacillus thuringiensis* is a species of bacteria that produces a crystal protein, also referred to as delta-endotoxin. This crystal protein is, technically, a protoxin that is converted into a toxin upon being ingested by larvae of lepidopteran and dipteran insects.

The crystal protein from *Bacillus thuringiensis* is a potentially important insecticide having no known harmful effects on humans, other mammals, birds, fish or on insects other than the larvae of lepidopteran, coleopteran and dipteran insects. Other advantages of the use of the crystal protein from *B. thuringiensis* as an insecticide include its broad spectrum of activity against lepidopteran and dipteran insect larvae, and the apparent difficulty of such larvae to develop resistance against the crystal protein, even where the crystal protein is used on a large scale.

The crystal protein is effective as an insecticide when it is applied to plants subject to lepidopteran larvae infestation. Such plants include broccoli, lettuce and cotton. Lepidopteran larvae infestation is especially serious in cotton plants. Application of the crystal protein to plants has usually been accomplished by standard methods such as by dusting or spraying.

The use of the crystal protein as a commercial insecticide has, however, been inhibited by a number of disadvantages. For example, the protoxin remains on the surface of the plants being treated, where it is effective only against surface-feeding larvae, and where it is inactivated by prolonged exposure to ultraviolet radiation. This inactivation may be at least one cause of the general lack of persistance of the crystal protein in the environment. Accordingly, frequent and expensive application of the crystal protein is necessary.

By taking advantage of genetic engineering, a gene responsible for the production of a useful polypeptide can be transferred from a donor cell, in which the gene naturally occurs, to a host cell, in which the gene does not naturally occur; Cohen and Boyer, U.S. Pat. Nos. 4,237,224 and 4,468,464. There are, in fact, few inherent limits to such transfers. Genes can be transferred between viruses, bacteria, plants and animals. In some cases, the transferred gene is functional, or can be made to be functional, in the host cell. When the host cell is a plant cell, whole plants can sometimes be regenerated from the cell.

Genes typically contain regions of DNA sequences including a promoter and a transcribed region. The transcribed region normally contains a 5' untranslated region, a coding sequence, and a 3' untranslated region.

The promoter contains the DNA sequence necessary for the initiation of transcription, during which the transcribed region is converted into mRNA. In eukaryotic cells, the promoter is believed to include a region recognized by RNA polymerase and a region which positions the RNA polymerase on the DNA for the initiation of transcription. This latter region, which is referred to as the TATA box, usually occurs about 30 nucleotides upstream from the site of transcription initiation.

Following the promoter region is a sequence that is transcribed into mRNA but is not translated into polypeptide. This sequence constitutes the so-called 5' untranslated region and is believed to contain sequences that are responsible for the initiation of translation, such as a ribosome binding site.

The coding region is the sequence that is just downstream from the 5' untranslated region in the DNA or the corresponding RNA. It is the coding region that is translated into polypeptides in accordance with the genetic code. *B. thuringiensis*, for example, has a gene with a coding sequence that translates into the amino acid sequence of the insecticidal crystal protein.

The coding region is followed by a sequence that is transcribed into mRNA, but is not translated into polypeptide. This sequence is called the 3' untranslated region and is believed to contain a signal that leads to the termination of transcription and, in eukaryotic mRNA, a signal that causes polyadenylation of the transcribed mRNA strand. Polyadenylation of the mRNA is believed to have processing and transportation functions.

Natural genes can be transferred in their entirety from a donor cell to a host cell. It is often preferable, however, to construct a gene containing the desired coding region with a promoter and, optionally, 5' and 3' untranslated regions that do not, in nature, exist in the same gene as the coding region. Such constructs are known as chimeric genes.

Genetic engineering methods have been described for improved ways of producing the crystal protein. For example, Schnepf et al, U.S. Pat. Nos. 4,448,885 and 4,467,036, describe plasmids for producing crystal protein in bacterial strains other than *B. thuringiensis*. These methods permit production of the crystal protein, but do not overcome the disadvantages of using the crystal protein as a commercial insecticide.

Suggestions have been made to clone *B. thuringiensis* toxin genes directly into plants in order to permit the plants to protect themselves; Klausner, A, Bio/Technology 2:408–419 (1984). Adang et al, European Patent Application 142, 924 (Agrigenetics), allege a method for cloning toxin genes from *B. thuringiensis* in tobacco and suggest protecting cotton the same way. Such a suggestion constitutes mere speculation, however, until methods for transforming cotton cells and regenerating plants from the cells are available. Such methods are described in U.S. patent application Ser. No. 122,200 filed Nov. 18, 1987 entitled "Regeneration and Transformation of Cotton", assigned to Phytogen, and U.S. patent application Ser. No. 122,162 filed Nov. 18, 1987 entitled "Regenerating Cotton from Cultured Cells", assigned to CIBA-GEIGY. U.S patent applications Ser. No. 122,200 and Ser. No. 122,162 were filed the same day as the present application. The disclosure of methods for transforming cotton cells in Phytogen patent application Ser. No. 122,200 and for regenerating cotton plants in Phytogen and CIBA-GEIGY patent applications Ser. No. 122,200 and Ser. No. 122,162 are incorporated herein be reference.

A need exists for developing new methods for producing the crystal protein of *B. thuringiensis* in cells of cotton plants and for new methods of killing lepidopteran larvae by feeding them cells of cotton plants containing a *B. thuringiensis* crystal protein or a similar polypeptide.

OBJECTS OF THE INVENTION

It is an object of the present invention to provide a method for producing in cotton cells a toxin that has substantially the insect toxicity properties of B. thuringiensis crystal protein.

It is a further object of the present invention to provide a method for killing lepidopteran larvae by feeding them cotton plant cells containing chimeric genes that express an insecticidal amount of a toxin having substantially the insect toxicity properties of B. thuringiensis crystal protein. The insecticidal cotton plant cells include those from whole plants and parts of plants as well as individual cotton cells in culture.

It is an additional object of the present invention to provide the genes and other DNA segments as well as the cells and plants associated with the above methods.

SUMMARY OF THE INVENTION

These and other objects of the present invention have been achieved by providing chimeric genes capable of expressing in cotton cells a polypeptide having substantially the insect toxicity properties of Bacillus thuringiensis crystal protein (hereinafter, chimeric Bt toxin gene).

Additional embodiments of the present invention include the chimeric Bt toxin gene in vectors, bacteria, plant cells in culture, and plant cells in living plants, as well as methods for producing a toxin having substantially the insect toxicity properties of Bacillus thuringiensis crystal protein in cotton cells and methods for killing insects by feeding them cotton cells containing a gene that expresses such a toxin.

DESCRIPTION OF THE DRAWINGS

FIG. 25. Nucleotide and amino acid sequences of rbc-gY (SEQ ID NOS 3 and 4). The first ATG and methionine of the transit peptide are boxed in the figure.

FIG. 26. Nucleotide and amino acid sequences of rbc-gX (SEQ ID NOS 5 and 6). The first ATG and methionine of the transit peptide are boxed in the figure.

DEPOSITS

Figure 1:
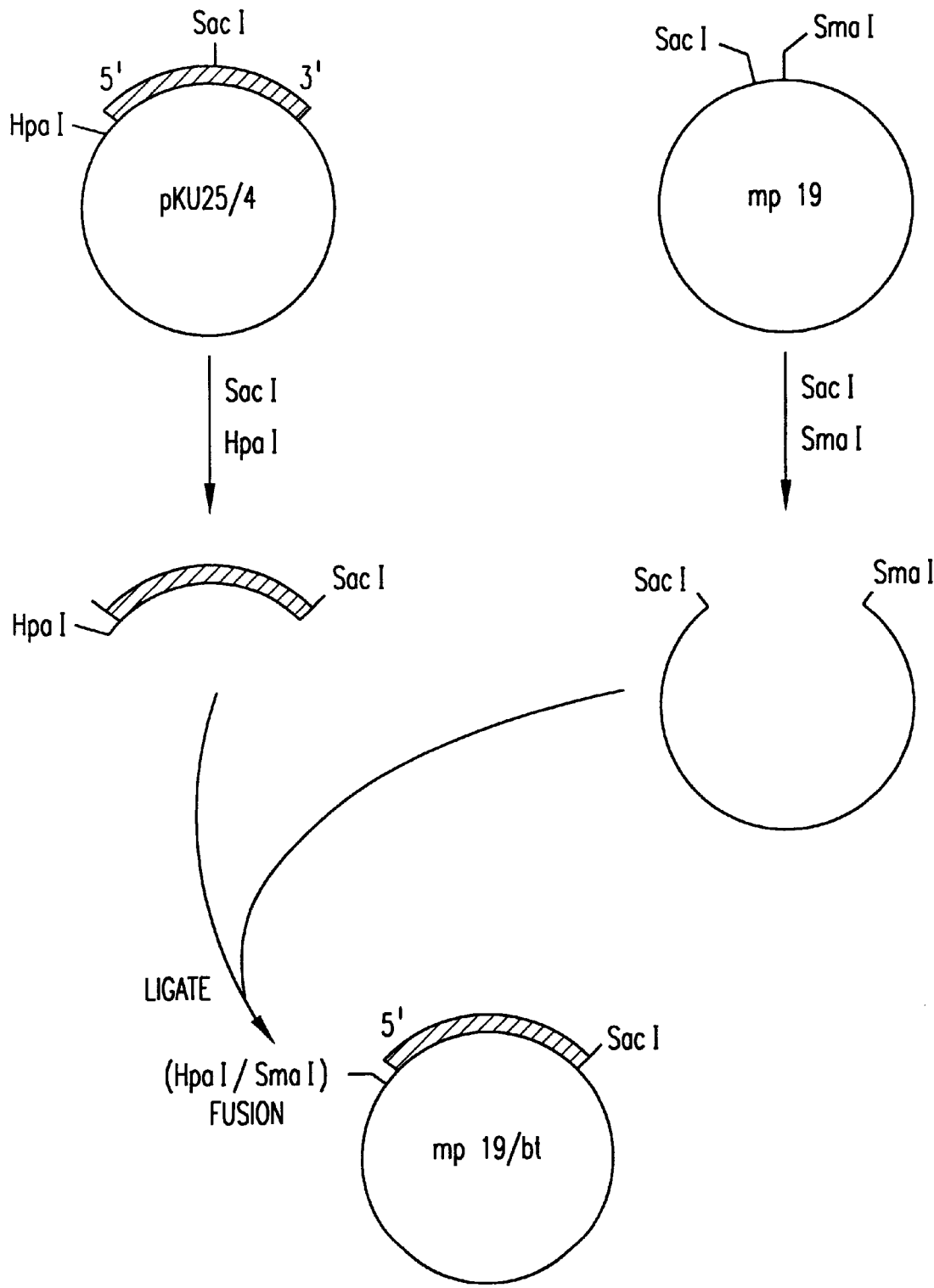
FIG. 1. Construction of mp 19/Bt, a plasmid containing the 5' end of the Bt protoxin gene.

Escherichia coli MC1061, pCIB10/35SBt . . . ATCC 67329

Escherichia coli HB101, pCIB/19SBt . . . ATCC 67330

Plasmid pLV111 . . . ATCC 40235

The first two deposits listed above were made on Feb. 27, 1987 and the third on May 14, 1986 in the American Type Culture Collection, Rockville, Md. in accordance with the Budapest Treaty.

Phage lambda/rbc-gY . . . ATCC 40486

Phage lambda/rbc-gX . . . ATCC 40487

These two deposits were made on Aug. 25, 1988 in the American Type Culture Collection in accordance with the Budapest Treaty.

DETAILED DESCRIPTION

The present invention is directed to the production of a chimeric BT toxin gene. The cotton plant cells contemplated include cells from any and all cotton plants into which foreign DNA can be introduced, replicated and expressed. Some suitable examples of cotton plant species include Gossypium hirsutum, Gossypium arboreum, and Gossypium barbadense. Gossypium hirsutum is preferred, and may be of the stripper or picker types. Stripper and picker cotton differ in their method of harvest, the stripper cotton bols being very firmly attached to the plant so that they are not released during late-season storms. Harvesting stripper cotton virtually destroys the plant. Picker cotton is less firmly attached and is harvested by less disruptive means. Some commercially available varieties of G. hirsutum capable of being regenerated by the method of the present invention include Acala 1515-75, Coker 304, Coker 315, Coker 201, Coker 310, Coker 312, DP 41, DP 90, Lankart 57, Lankart 611, McNair 235, Paymaster 145, Stoneville 506, Stoneville 825, Tomcot SP 21-S, Acala SJ-2, Acala SJ-4, Acala SJ-5, Acala SJC-1, Acala GC 510, Acala SJC-22, Acala SJC-28, Acala SJC-30, Siokra, Acala B-1644, Acala B-1810, Acala B-2724, Funk 519-2, Funk FC 3008, Funk FC 3024, Funk C 1568R, Funk FC 2005, Funk C 0947B, Funk FC 2028, Funk FC 2017, Funk C 1379, DPL 50, DPL 20, DPL 120, DPL 775, Tx-CAB-CS and Paymaster HS 26.

The preferred varieties are Acala SJ-2, Acala SJC-1, Acala GC 510, Acala SJC-28, Acala SJC-30, Acala B-1644 and Siokra.

Acala SJ-2, Acala GC 510, Acala B-1644, and Siokra are especially preferred.

The term "plant cell" refers to any cell derived from a cotton plant. Some examples of cells encompassed by the present invention include differentiated cells that are part of a living plant; undifferentiated cells in culture; the cells of undifferentiated tissue such as callus or tumors; seeds; embryos; propagules and pollen.

The chimeric gene of this invention contains a promoter region that functions efficiently in cotton plants and coding region that codes for the crystal protein from *B. thuringiensis* or for a polypeptide having substantially the insecticidal properties of the crystal protein from *B. thuringiensis*. The coding sequence of the chimeric gene is not known to be associated with the promoter in natural genes.

The 5' and/or 3' untranslated regions may, independently, be associated in nature with either the promoter or the coding region, or with neither the promoter or the coding region. Preferably, either the 5' or the 3' untranslated region is associated with the promoter in natural genes, and most preferably both the 5' and 3' regions are associated with the promoter in natural genes.

One could not predict, based on the state of the art at the time this invention was made, that a chimeric gene could be stably and functionally introduced into cotton cells. It was even less predictable that such cells would express an insecticidal polypeptide at any level, and especially at sufficient levels to impart insecticidal properties to the cells.

In order to be considered insecticidal, the plant cells must contain an insecticidal amount of toxin having substantially the insecticidal activity of the crystal protein from *Bacillus thuringiensis*. An insecticidal amount is an amount which, when present in plant cells, kills insects or at least prevents a function necessary for growth, such as feeding. Accordingly, the plant cells of the present invention are able to withstand attacks by lepidopteran larvae without, or with less, application of crystal protein or other insecticide when compared with plant cells that do not contain a gene producing an insecticidal polypeptide.

The Gene

The Transcription Control Sequences

The chimeric gene of this invention contains transcription control sequences comprising promoter and 5' and 3' untranslated sequences that are functional in cotton plants. These sequences may, independently, be derived from any source, such as, for example, virus, plant or bacterial genes.

The virus promoters and 5' and 3' untranslated sequences suitable for use are functional in cotton plants and include, for example, plant viruses such as cauliflower mosaic virus. Cauliflower mosaic virus (CaMV) has been characterized and described by Hohn et al in Current Topics in Microbiology and Immunology, 96, 194–220 and appendices A to G (1982). This description is incorporated herein by reference.

CaMV is an unusual plant virus in that it contains double-stranded DNA. At least two CaMV promoters are functional in plants, namely the 19S promoter, which results in transcription of gene VI or CaMV, and the 35S promoter. The 19S promoter and the 35S promoter are the preferred plant virus promoters for use in the present invention.

Figure 4:
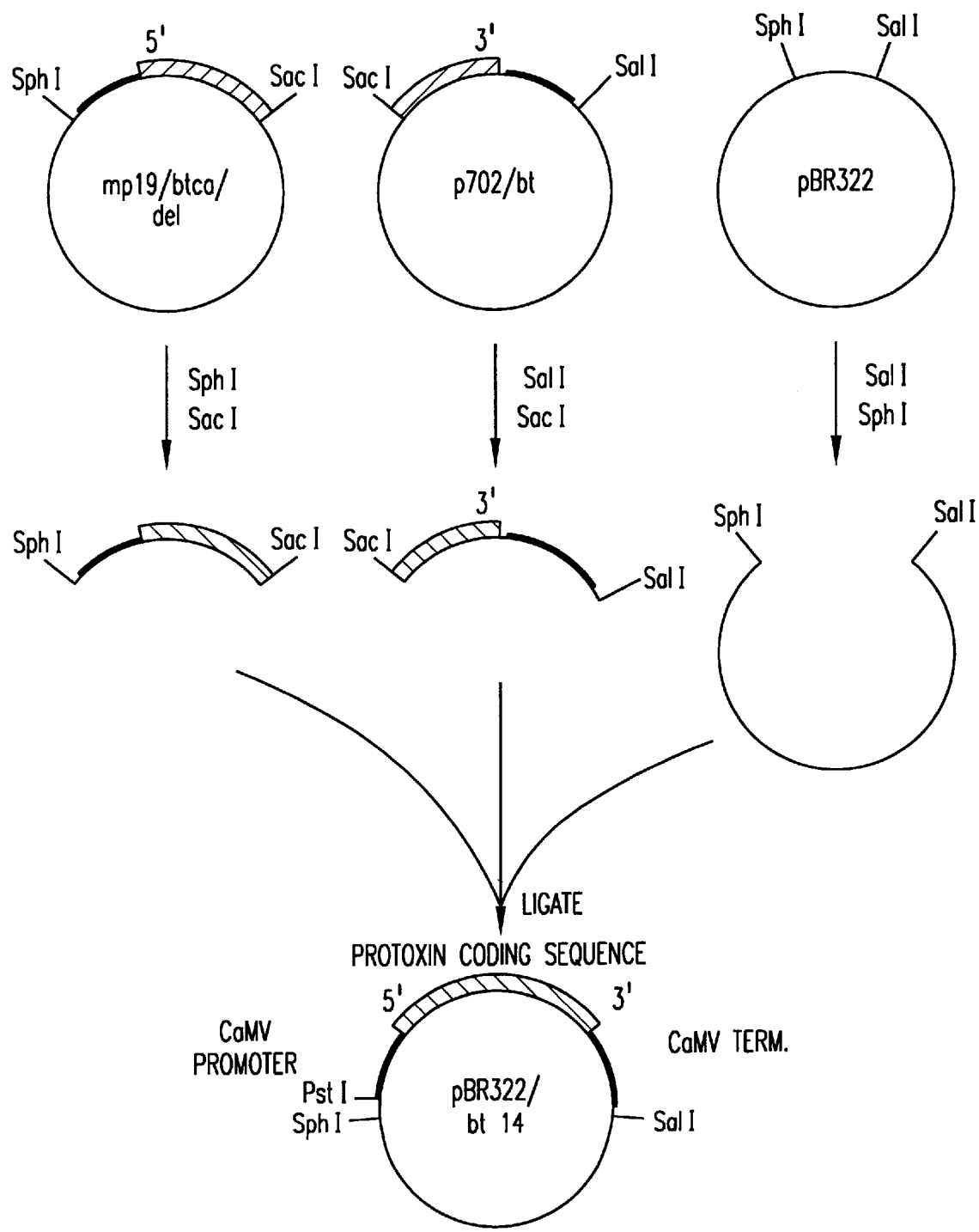
FIG. 4. Construction of pBR322/Bt 14, containing the complete protoxin coding sequence flanked by CaMV promoter and terminator sequences.

CaMV 19S promoters and 5' untranslated regions may be obtained by means of a restriction map such as the map described in FIG. 4 on page 199 of the Hohn et al article mentioned above, or from the sequence that appears in Appendix C of the Hohn et al article.

In order to isolate the CaMV 19S promoter and, optionally, the adjacent 5' untranslated region, a restriction fragment of the CaMV genome containing the desired sequences is selected. A suitable restriction fragment that contains the 19S promoter and the 5' untranslated region is the fragment between the PstI site starting at position 5386 and the HindIII site starting at position 5850 of FIG. 4 and appendix C of the Hohn et al article.

By analgous methods, the 35S promoter from CaMV may be obtained, as is described in example 6 below.

Undesired nucleotides in the restriction fragment may optionally be removed by standard methods. Some suitable methods for deleting undesired nucleotides include the use of exonucleases (Maniatis et al, Molecular Cloning, Cold Spring Harbor Laboratory, Cold Spring Harbor, N.Y. pages 135–139 (1982)) and oligonucleotide-directed mutagenesis (Zoller et al, Methods in Enzymology, 100, 468 (1983)).

A similar procedure may be used to obtain a desirable 3' untranslated region. For example, a suitable CaMV 19S gene 3' untranslated sequence may be obtained by isolating the region between the EcoRV site at position 7342 and the BglII site at position 7643 of the CaMV genome as described in FIG. 4 and appendix C of the Hohn et al article.

Examples of plant gene promoters and 5' and 3' untranslated regions suitable for use in the present invention also include those of the gene coding for the small subunit of ribulose bisphosphate carboxylase and chlorophyl a/b-binding protein. These plant gene regions may be isolated from plant cells in ways comparable to those described above for isolating the corresponding regions from CaMV; see Morelli et al, Nature, 315, 200–204 (1985).

Suitable promoters and 5' and 3' untranslated regions from bacterial genes include those present in the T-DNA region of Agrobacterium plasmids. Some examples of suitable Agrobacterium plasmids include the Ti plasmid of *A. tumefaciens* and the Ri plasmid of *A. rhizogenes*. The Agrobacterium promoters and 5' and 3' untranslated regions useful in the present invention are, in particular, those present in the gene coding for octopine and nopaline synthase. These sequences may be obtained by methods similar to those described above for isolating CaMV and plant promoters and untranslated sequences; see Bevan et al, Nature, 304, 184–187 (1983).

The Coding Region

The coding region of the chimeric gene contains a nucleotide sequence that codes for a polypeptide having substantially the toxicity properties of a *Bacillus thuringiensis* delta-endotoxin crystal protein. A polypeptide, for the purpose of the present invention, has substantially the toxicity properties of *Bacillus thuringiensis* delta-endotoxin crystal protein if it is insecticidal to a similar range of insect larvae as is the crystal protein from a subspecies of *Bacillus thuringiensis*. Some suitable subspecies include for example kurstaki, berliner, alesti, tolworthi, sotto, dendrolimus, tenebrionis, sandiego and aizawai. The preferred subspecies is kurstaki, and especially kurstaki HD1.

The coding region may exist naturally in *Bacillus thuringiensis*. Alternatively, the coding region may contain a sequence that is different from the sequence that exists in *Bacillus thuringiensis*, but is equivalent because of the degeneracy of the genetic code.

The coding sequence of the chimeric gene may also code for a polypeptide that differs from a naturally occuring crystal protein delta-endotoxin but that still has substantially the insect toxicity properties of the crystal protein. Such a coding sequence will usually be a variant of a natural coding region. A "variant" of a natural DNA sequence is a modified form of the natural sequence that performs the same function. The variant may be a mutation, or may be a synthetic DNA sequence, and is substantially homologus to the corresponding natural sequence. A DNA sequence is substantially homologous to a second DNA sequence if at least 70%, preferably at least 80% and most preferably at least 90% of the active portions of the DNA sequence are homologous. Two different nucleotides are considered to be homologous in a DNA sequence of a coding region for the purpose of determining substantial homology if the substitution of one for the other constitutes a silent mutation.

The invention thus includes cotton cells and plants containing any chimeric gene coding for a sequence of amino acids having the insecticidal properties satisfying the requirements disclosed and claimed. It is preferred that the nucleotide sequence is substantially homologous at least to that portion or to those portions of the natural sequence responsible for insecticidal activity.

The polypeptide expressed by the chimeric gene of this invention will generally also share at least some immunological properties with a natural crystal protein, since it has at least some of the same antigenic determinants.

Accordingly, the polypeptide coded for by the chimeric gene of the present invention is preferably structurally related to the delta-endotoxin of the crystal protein produced by *Bacillus thuringiensis*. *Bacillus thuringiensis* produces a crystal protein with a subunit which is a protoxin having an Mr of about 130,000 to 140,000. This subunit can be cleaved by proteases or by alkali to form insecticidal fragments having an Mr as low as about 80,000, preferably about 70,000, more preferably about 60,000, and possibly even lower. The fragments preferably have a maximum Mr of about 120,000, more preferably about 110,000 and most preferably about 100,000. Chimeric genes that code for such fragments of the protoxin according to the present invention can be constructed as long as the fragments or portions of fragments have the requisite insecticidal activity. The protoxin, insecticidal fragments of the protoxin and insecticidal portions of these fragments can also be fused to other molecules such as polypeptides and proteins.

Coding regions suitable for use in the present invention may be obtained from crystal protein toxin genes isolated from *Bacillus thuringiensis*, for example, see Whitely et al., PCT application WO 86/01536 and U.S. Pat. Nos. 4,448,885 and 4,467,036. A preferred sequence of nucleotides that codes for a crystal protein is that shown in Formula I or a shorter sequence that codes for an insecticidal fragment of such a crystal protein. The disclosure of this sequence in Geiser et al., Gene 48:109–118 (1986) is incorporated herein by reference.

The coding region of Formula I encodes the polypeptide of Formula II. The nucleotide sequence of Formula I and the amino acid sequence of Formula II are depicted in SEQ ID NOS 1 and 2 respectively.

| FORMULA I | |
|---|---|
| 1 | GTTAACACCC TGGGTCAAAA ATTGATATTT AGTAAAATTA GTTGCACTTT |
| 51 | GTGCATTTT TCATAAGATG AGTCATATGT TTTAAATTGT AGTAATGAAA |
| 101 | AACAGTATTA TATCATAATG AATTGGTATC TTAATAAAAG AGATGGAGGT |
| 151 | AACTTATGGA TAACAATCCG AACATCAATG AATGCATTCC TTATAATTGT |
| 201 | TTAAGTAACC CTGAAGTAGA AGTATTAGGT GGAGAAAGAA TAGAAACTGG |
| 251 | TTACACCCCA ATCGATATTT CCTTGTCGCT AACGCAATTT CTTTTGAGTG |
| 301 | AATTTGTTCC CGGTGCTGGA TTTGTGTTAG GACTAGTTGA TATAATATGG |
| 351 | GGAATTTTTG GTCCCTCTCA ATGGGACGCA TTTCTTGTAC AAATTGAACA |
| 401 | GTTAATTAAC CAAAGAATAG AAGAATTCGC TAGGAACCAA GCCATTTCTA |
| 451 | GATTAGAAGG ACTAAGCAAT CTTTATCAAA TTTACGCAGA ATCTTTTAGA |
| 501 | GAGTGGGAAG CAGATCCTAC TAATCCAGCA TTAAGAGAAG AGATGCGTAT |
| 551 | TCAATTCAAT GACATGAACA GTGCCCTTAC AACCGCTATT CCTCTTTTTG |
| 601 | CAGTTCAAAA TTATCAAGTT CCTCTTTTAT CAGTATATGT TCAAGCTGCA |
| 651 | AATTTACATT TATCAGTTTT GAGAGATGTT TCAGTGTTTG GACAAAGGTG |
| 701 | GGGATTTGAT GCCGCGACTA TCAATAGTCG TTATAATGAT TTAACTAGGC |
| 751 | TTATTGGCAA CTATACAGAT CATGCTGTAC GCTGGTACAA TACGGGATTA |
| 801 | GAGCGTGTAT GGGGACCGGA TTCTAGAGAT TGGATAAGAT ATAATCAATT |
| 851 | TAGAAGAGAA TTAACACTAA CTGTATTAGA TATCGTTTCT CTATTTCCGA |
| 901 | ACTATGATAG TAGAACGTAT CCAATTCGAA CAGTTTCCCA ATTAACAAGA |
| 951 | GAAATTTATA CAAACCCAGT ATTAGAAAAT TTTGATGGTA GTTTTCGAGG |
| 1001 | CTCGGCTCAG GGCATAGAAG GAAGTATTAG GAGTCCACAT TTGATGGATA |
| 1051 | TACTTAACAG TATAACCATC TATACGGATG CTCATAGAGG AGAATATTAT |
| 1101 | TGGTCAGGGC ATCAAATAAT GGCTTCTCCT GTAGGGTTTT CGGGGCCAGA |

-continued

FORMULA I

```
1151 ATTCACTTTT CCGCTATATG GAACTATGGG AAATGCAGCT CCACAACAAC
1201 GTATTGTTGC TCAACTAGGT CAGGGCGTGT ATAGAACATT ATCGTCCACT
1251 TTATATAGAA GACCTTTTAA TATAGGGATA AATAATCAAC AACTATCTGT
1301 TCTTGACGGG ACAGAATTTG CTTATGGAAC CTCCTCAAAT TTGCCATCCG
1351 CTGTATACAG AAAAAGCGGA ACGGTAGATT CGCTGGATGA AATACCGCCA
1401 CAGAATAACA ACGTGCCACC TAGGCAAGGA TTTAGTCATC GATTAAGCCA
1451 TGTTTCAATG TTTCGTTCAG GCTTTAGTAA TAGTAGTGTA AGTATAATAA
1501 GAGCTCCTAT GTTCTCTTGG ATACATCGTA GTGCTGAATT TAATAATATA
1551 ATTCCTTCAT CACAAATTAC ACAAATACCT TTAACAAAAT CTACTAATCT
1601 TGGCTCTGGA ACTTCTGTCG TTAAAGGACC AGGATTTACA GGAGGAGATA
1651 TTCTTCGAAG AACTTCACCT GGCCAGATTT CAACCTTAAG AGTAAATATT
1701 ACTGCACCAT TATCACAAAG ATATCGGGTA AGAATTCGCT ACGCTTCTAC
1751 CACAAATTTA CAATTCCATA CATCAATTGA CGGAAGACCT ATTAATCAGG
1801 GGAATTTTTC AGCAACTATG AGTAGTGGGA TAATTTACA GTCCGGAAGC
1851 TTTAGGACTG TAGGTTTTAC TACTCCGTTT AACTTTTCAA ATGGATCAAG
1901 TGTATTTACG TTAAGTGCTC ATGTCTTCAA TTCAGGCAAT GAAGTTTATA
1951 TAGATCGAAT TGAATTTGTT CCGGCAGAAG TAACCTTTGA GGCAGAATAT
2001 GATTTAGAAA GAGCACAAAA GGCGGTGAAT GAGCTGTTTA CTTCTTCCAA
2051 TCAAATCGGG TTAAAAACAG ATGTGACGGA TTATCATATT GATCAAGTAT
2101 CCAATTTAGT TGAGTGTTTA TCTGATGAAT TTTGTCTGGA TGAAAAAAAA
2151 GAATTGTCCG AGAAAGTCAA ACATGCGAAG CGACTTAGTG ATGAGCGGAA
2201 TTTACTTCAA GATCCAAACT TTAGAGGGAT CAATAGACAA CTAGACCGTG
2251 GCTGGAGAGG AAGTACGGAT ATTACCATCC AAGGAGGCGA TGACGTATTC
2301 AAAGAGAATT ACGTTACGCT ATTGGGTACC TTTGATGAGT GCTATCCAAC
2351 GTATTTATAT CAAAAAATAG ATGAGTCGAA ATTAAAAGCC TATACCCGTT
2401 ACCAATTAAG AGGGTATATC GAAGATAGTC AAGACTTAGA AATCTATTTA
2451 ATTCGCTACA ATGCCAAACA CGAAACAGTA AATGTGCCAG GTACGGGTTC
2501 CTTATGGCCG CTTTCAGCCC AAGTCCAAT CGGAAAATGT GCCCATCATT
2551 CCCATCATTT CTCCTTGGAC ATTGATGTTG GATGTACAGA CTTAAATGAG
2601 GACTTAGGTG TATGGGTGAT ATTCAAGATT AAGACGCAAG ATGGCCATGC
2651 AAGACTAGGA AATCTAGAAT TTCTCGAAGA GAAACCATTA GTAGGAGAAG
2701 CACTAGCTCG TGTGAAAAGA GCGGAGAAAA AATGGAGAGA CAAACGTGAA
2751 AAATTGGAAT GGGAAACAAA TATTGTTTAT AAAGAGGCAA AAGAATCTGT
2801 AGATGCTTTA TTTGTAAACT CTCAATATGA TAGATTACAA GCGGATACCA
2851 ACATCGCGAT GATTCATGCG GCAGATAAAC GCGTTCATAG CATTCGAGAA
2901 GCTTATCTGC CTGAGCTGTC TGTGATTCCG GGTGTCAATG CGGCTATTTT
2951 TGAAGAATTA GAAGGGCGTA TTTTCACTGC ATTCTCCCTA TATGATGCGA
3001 GAAATGTCAT TAAAAATGGT GATTTTAATA ATGGCTTATC CTGCTGGAAC
```

-continued

| FORMULA I |
|---|
| 3051 GTGAAAGGGC ATGTAGATGT AGAAGAACAA ACAACCACC GTTCGGTCCT |
| 3101 TGTTGTTCCG GAATGGGAAG CAGAAGTGTC ACAAGAAGTT CGTGTCTGTC |
| 3151 CGGGTCGTGG CTATATCCTT CGTGTCACAG CGTACAAGGA GGGATATGGA |
| 3201 GAAGGTTGCG TAACCATTCA TGAGATCGAG AACAATACAG ACGAACTGAA |
| 3251 GTTTAGCAAC TGTGTAGAAG AGGAAGTATA TCCAAACAAC ACGGTAACGT |
| 3301 GTAATGATTA TACTGCGACT CAAGAAGAAT ATGAGGGTAC GTACACTTCT |
| 3351 CGTAATCGAG GATATGACGG AGCCTATGAA AGCAATTCTT CTGTACCAGC |
| 3401 TGATTATGCA TCAGCCTATG AAGAAAAAGC ATATACAGAT GGACGAAGAG |
| 3451 ACAATCCTTG TGAATCTAAC AGAGGATATG GGGATTACAC ACCACTACCA |
| 3501 GCTGGCTATG TGACAAAAGA ATTAGAGTAC TTCCCAGAAA CCGATAAGGT |
| 3551 ATGGATTGAG ATCGGAGAAA CGGAAGGAAC ATTCATCGTG GACAGCGTGG |
| 3601 AATTACTTCT TATGGAGGAA TAATATATGC TTTATAATGT AAGGTGTGCA |
| 3651 AATAAAGAAT GATTACTGAC TTGTATTGAC AGATAAATAA GGAAATTTTT |
| 3701 ATATGAATAA AAAACGGGCA TCACTCTTAA AAGAATGATG TCCGTTTTTT |
| 3751 GTATGATTTA ACGAGTGATA TTTAAATGTT TTTTTTGCGA AGGCTTTACT |
| 3801 TAACGGGGTA CCGCCACATG CCCATCAACT TAAGAATTTG CACTACCCCC |
| 3851 AAGTGTCAAA AAACGTTATT CTTTCTAAAA AGCTAGCTAG AAAGGATGAC |
| 3901 ATTTTTTATG AATCTTTCAA TTCAAGATGA ATTACAACTA TTTTCTGAAG |
| 3951 AGCTGTATCG TCATTTAACC CCTTCTCTTT TGGAAGAACT CGCTAAAGAA |
| 4001 TTAGGTTTTG TAAAAAGAAA ACGAAAGTTT TCAGGAAATG AATTAGCTAC |
| 4051 CATATGTATC TGGGGCAGTC AACGTACAGC GAGTGATTCT CTCGTTCGAC |
| 4101 TATGCAGTCA ATTACACGCC GCCACAGCAC TCTTATGAGT CCAGAAGGAC |
| 4151 TCAATAAACG CTTTGATAAA AAAGCGGTTG AATTTTTGAA ATATATTTTT |
| 4201 TCTGCATTAT GGAAAAGTAA ACTTTGTAAA ACATCAGCCA TTTCAAGTGC |
| 4251 AGCACTCACG TATTTTCAAC GAATCCGTAT TTTAGATGCG ACGATTTTCC |
| 4301 AAGTACCGAA ACATTTAGCA CATGTATATC CTGGGTCAGG TGGTTGTGCA |
| 4351 CAAACTGCAG |

| FORMULA II | |
|---|---|
| MetAspAsnAsnProAsnIleAsnGluCysIleProTyrAsnCysLeuSerAsnProGly - | 20 |
| ValGluValLeuGlyGlyGluArgIleGluThrGlyTyrThrProIleAspIleSerLeu - | |
| SerLeuThrGlnPheLeuLeuSerGluPheValProGlyAlaGlyPheValLeuGlyLeu - | |
| ValAspIleIleTrpGlyIlePheGlyProSerGlnTrpAspAlaPheLeuValGlnIle - | |
| GluGlnLeuIleAsnGlnArgIleGluGluPheAlaArgAsnGlnAlaIleSerArgLeu - | |
| GluGlyLeuSerAsnLeuTyrGlnIleTyrAlaGluSerPheArgGluTrpGluAlaAsp - | |
| ProThrAsnProAlaLeuArgGluGluMetArgIleGlnPheAsnAspMetAsnSerAla - | |
| LeuThrThrAlaIleProLeuPheAlaValGlnAsnTyrGlnValProLeuLeuSerVal - | |

-continued

FORMULA II

| | |
|---|---|
| TyrValGlnAlaAlaAsnLeuHisLeuSerValLeuArgAspValSerValPheGlyGln - | |
| ArgTrpGlyPheAspAlaAlaThrIleAsnSerArgTyrAsnAspLeuThrArgLeuIle - | 200 |
| GlyAsnTyrThrAspHisAlaValArgTrpTyrAsnThrGlyLeuGluArgValTrpGly - | |
| ProAspSerArgAspTrpIleArgTyrAsnGlnPheArgArgGluLeuThrLeuThrVal - | |
| LeuAspIleValSerLeuPheProAsnTyrAspSerArgThrTyrProIleArgThrVal - | |
| SerGlnLeuThrArgGluIleTyrThrAsnProValLeuGluAsnPheAspGlySerPhe - | |
| ArgGlySerAlaGlnGlyIleGluGlySerIleArgSerProHisLeuMetAspIleLeu - | |
| AsnSerIleThrIleTyrThrAspAlaHisArgGlyGluTyrTyrTrpSerGlyHisGln - | |
| IleMetAlaSerProValGlyPheSerGlyProGluPheThrPheProLeuTyrGlyThr - | |
| MetGlyAsnAlaAlaProGlnGlnArgIleValAlaGlnLeuGlyGlnGlyValTyrArg - | |
| ThrLeuSerSerThrLeuTyrArgArgProPheAsnIleGlyIleAsnAsnGlnGlnLeu - | |
| SerValLeuAspGlyThrGluPheAlaTyrGlyThrSerSerAsnLeuProSerAlaVal - | 400 |
| TyrArgLysSerGlyThrValAspSerLeuAspGluIleProProGlnAsnAsnAsnVal - | |
| ProProArgGlnGlyPheSerHisArgLeuSerHisValSerMetPheArgSerGlyPhe - | |
| SerAsnSerSerValSerIleIleArgAlaProMetPheSerTrpIleHisArgSerAla - | |
| GluPheAsnAsnIleIleProSerSerGlnIleThrGlnIleProLeuThrLysSerThr - | |
| AsnLeuGlySerGlyThrSerValValLysGlyProGlyPhrThrGlyGlyAspIleLeu - | |
| ArgArgThrSerProGlyGlnIleSerThrLeuArgValAsnIleThrAlaProLeuSer - | |
| GlnArgTyrArgValArgIleArgTyrAlaSerThrThrAsnLeuGlnPheHisThrSer - | |
| IleAspGlyArgProIleAsnGlnGlyAsnPheSerAlaThrMetSerSerGlySerAsn - | |
| LeuGlnSerGlySerPheArgThrValGlyPheThrThrProPheAsnPheSerAsnGly - | 580 |
| SerSerValPheThrLeuSerAlaHisValPheAsnSerGlyAsnGluValTyrIleAsp - | 600 |
| ArgIleGluPheValProAlaGluValThrPheGluAlaGluTyrAspLeuGluArgAla - | |
| GlnLysAlaValAsnGluLeuPheThrSerSerAsnGlnIleGlyLeuLysThrAspVal - | |
| ThrAspTyrHisIleAspGlnValSerAsnLeuValGluCysLeuSerAspGluPheCys - | |
| LeuAspGluLysLysGluLeuSerGluLysValLysHisAlaLysArgLeuSerAspGlu - | |
| ArgAsnLeuLeuGlnAspProAsnPheArgGluIleAsnArgGlnLeuAspArgGlyTrp - | |
| ArgGlySerThrAspIleThrIleGlnGlyGlyAspAspValPheLysGluAsnTyrVal - | |
| ThrLeuLeuGlyThrPheAspGluCysTyrProThrTyrLeuTyrGlnLysIleAspGlu - | |
| SerLysLeuLysAlaTyrThrArgTyrGlnLeuArgGlyTyrIleGluAspSerGlnAsp - | |
| LeuGluIleTyrLeuIleArgTyrAsnAlaLysHisGluThrValAsnValProGlyThr - | |
| GlySerLeuTrpProLeuSerAlaProSerProIleGlyLysCysAlaHisHisSerHis - | 800 |
| HisPheSerLeuAspIleAspValGlyCysThrAspLeuAsnGluAspLeuGlyValTrp - | |
| ValIlePheLysIleLysThrGlnAspGlyHisAlaArgLeuGlyAsnLeuGluPheLeu - | |
| GluGluLysProLeuValGlyGluAlaLeuAlaArgValLysArgAlaGluLysLysTrp - | |
| ArgAspLysArgGluLysLeuGluTrpGluThrAsnIleValTyrLysGluAlaLysGlu - | |
| SerValAspAlaLeuPheValAsnSerGlnTyrAspArgLeuGlnAlaAspThrAsnIle - | |
| AlaMetIleHisAlaAlaAspLysArgValHisSerIleArgGluAlaTyrLeuProGlu - | |
| LeuSerValIleProGlyValAsnAlaAlaIlePheGluGluLeuGluGlyArgIlePhe - | |

-continued

FORMULA II

```
ThrAlaPheSerLeuTyrAspAlaArgAsnValIleLysAsnGlyAspPheAsnAsnGly -
LeuSerVysTrpAsnValLysGlyHisValAspValGluGluGlnAsnAsnHisArgSer -
ValLeuValValProGluTrpGluAlaGluValSerGlnGluValARgValCysProGly -   1000
ArgGlyTyrIleLeuArgValThrAlaTyrLysGluGlyTyrGlyGluGlyCysValThr -
IleHisGluIleGluAsnAsnThrAspGluLeuLysPheSerAsnCysValGluGluGlu -
ValTyrProAsnAsnThrValThrCysAsnAspTyrThrAlaThrGlnGluGluTyrGlu -
GlyThrTyrThrSerArgAsnArgGlyTyrAspGlyAlaTyrGluSerAsnSerSerVal -
ProAlaAspTyrAlaSerAlaTyrGluGluLysAlaTyrThrAspGlyArgArgAspAsn -   1100
ProCysGluSerAsnArgGlyTyrGlyAspTyrThrProLeuProAlaGlyTyrValThr -
LysGluLeuGluTyrPheProGluThrAspLysValTrpIleGluIleGlyGluThrGlu -
GlyThrPheIleValAspSerValGluLeuLeuLeuMetGluGluEnd -
```

Vectors

In order to introduce the chimeric gene of the present invention into plant cells, the gene is first inserted into a vector. If the gene is not available in an amount sufficient for transformation, the vector may be amplified by replication in a host cell. The most convenient host cells for amplification are bacterial or yeast cells. When a sufficient amount of the chimeric gene is available, it is introduced into cotton cells or tissue. The introduction of the gene into cotton plant cells or tissue may be by means of the same vector used for replication, or by means of a different vector.

Some examples of bacterial host cells suitable for replicating the chimeric gene include those of the genus Escherischia such as *E. coli* and Agrobacterium such as *A. tumefaciens* or *A. rhizogenes*. Methods for cloning heterologous genes in bacteria are described by Cohen et al, U.S. Pat. Nos. 4,448,885 and 4,467,036. The replication of genes coding for the crystal protein of *Bacillus thuringiensis* in *E. coli* is described in Wong et al., J. Biol. Chem. 258:1960–1967 (1983).

The preferred bacterium host cell for amplifying the chimeric Bt genes of this invention is Agrobacterium. The advantage of amplifying the gene in Agrobacterium is that the Agrobacterium may then be used to insert the amplified gene into plant cells without further genetic manipulation.

Some examples of yeast host cells suitable for replicating the genes of this invention include those of the genus Saccharomyces.

Any vector into which the chimeric gene can be inserted and which replicates in a suitable host cell, such as in bacteria or yeast, may be used to amplify the genes of this invention. The vector may, for example, be derived from a phage or a plasmid. Some examples of vectors derived from phages useful in the invention include those derived from M13 and from lambda. Some suitable vectors derived from M13 include M13mp18 and M13mp19. Some suitable vectors derived from lambda include lambda-gt11, lambda-gt7 and lambda Charon 4.

Some vectors derived from plasmids expecially suitable for replication in bacteria include pBR322 (Bolivar et al, Gene, 2, 95–113 (1977); pUC18 and pUC19 (Norrander et al, Gene, 26, 101–106 (1983)); and Ti plasmids (Bevan et al., Nature, 304, 184–187 (1983)). The preferred vector for amplifying the gene in bacteria is pBR322.

Construction of Vectors for Replication

In order to construct a chimeric gene suitable for replication in bacteria, a promoter sequence, a 5' untranslated sequence, a coding sequence and a 3' untranslated sequence are inserted into or are assembled in the proper order in a suitable vector, such as a vector described above. In order to be suitable, the vector must be able to replicate in the host cell.

The promoter, 5' untranslated region, coding region and 3' untranslated region, which comprise the chimeric gene of the invention, may first be combined in one unit outside the vector, and then inserted into the vector. Alternatively, portions of the chimeric gene may be inserted into the vector separately. The vector preferably also contains a gene that confers a trait on the host cell permitting the selection of cells containing the vector. The preferred trait is antibiotic resistance. Some examples of useful antibiotics include ampicillin, tetracycline, hygromycin, G418, chloramphenicol, kanamycin, and neomycin.

Insertion or assembly of the gene in the vector is accomplished by standard methods such as the use of recombinant DNA [Maniatis, et al., *Molecular Cloning, A Laboratory Manual*, Cold Spring Harbor Laboratory, Cold Spring Harbor, N.Y. (1982)] and homologous recombination [Hinnen et al., Proc. Natl. Acad. Sci. USA, 75:1929–1933 (1978)].

In recombinant DNA methods, the vector is cut, the desired DNA sequence is inserted between the cut pieces of the vector, and the ends of the desired DNA sequence are ligated to the corresponding ends of the vector.

The vector is most conveniently cut by means of suitable restriction endonucleases. Some suitable restriction endonucleases include those which form blunt ends, such as SmaI, HpaI and EcoRV, and those which form cohesive ends, such as EcoRI, SacI and BamHI.

The desired DNA sequence normally exists as part of a larger DNA molecule such as a chromosome, plasmid or transposon. THe desired DNA sequence is excised from its source, and optionally modified so that the ends can be joined to the ends of the cut vector. If the ends of the desired DNA sequence and of the cut vector are blunt ends, they are joined by blunt end ligases such as T4 DNA ligase.

The ends of the desired DNA sequence may also be joined to the ends of the cut vector in the form of cohesive ends, in which case a cohesive-end ligase, which may also be T4 DNA ligase; is used. Other suitable cohesive-end ligases include, for example, *E. coli* DNA ligase.

Cohesive ends are most conveniently formed by cutting the desired DNA sequence and the vector with the same restriction endonuclease. In such a case, the desired DNA sequence and the cut vector have cohesive ends that are complementary to each other.

The cohesive ends may also be constructed by adding complementary homopolymer tails to the ends of the desired DNA sequence and to the cut vector using terminal deoxynucleotidyl transferase. Cohesive ends may also be constructed by adding a synthetic oligonucleotide sequence recognized by a particular restriction endonuclease, and cleaving the sequence with the endonuclease; see, for example, Maniatis et al, *Molecular Cloning, a Laboratory Manual*, Cold Spring Harbor Laboratory, Cold Spring Harbor, N.Y., 1982. Such synthetic oligonucleotide sequences are known as linkers.

Construction of Vectors for Transformation of Plants

The Bt toxin genes of the present invention may be introduced directly into plant cells by taking advantage of certain plasmids present in Agrobacterium. These plasmids contain regions that are naturally inserted into the genome of plant cells infected by Agrobacterium. The inserted region is called T-DNA (transferred-DNA). These plasmids, examples of which include the Ti (tumor inducing) plasmid of *A. tumefacieus* and the Ri (root inducing) plasmid of *A. rhizogenes*, contain T-DNA border sequences, at least one of which is believed to be necessary for the transfer of the T-DNA region from the plasmid to the genome of the infected plant cell. Natural Ti and Ri plasmids also contain virulence regions, the location of which is believed to be outside of the T-DNA region. The virulence regions are needed for the transfer of T-DNA to plant cells.

In modified systems the virulence regions may exist on plasmids different from the plasmid that contains the T-DNA. Such virulence region-containing plasmids are called helper plasmids.

The T-DNA regions that occur naturally are oncogenic and cause plant tumors. The oncogenic portions of these T-DNA regions may be partially or fully removed before, or simultaneously with, the insertion of the desired DNA sequence. The plasmids containing such modified T-DNA regions are said to be disarmed.

The genes suitable for use in the present invention are assembled in or are inserted into a T-DNA vector system by methods known in the art (Barton and Chilton, Methods in Enzymology, 101: 527 (1984) 1983; Chilton, "Plant Gene Vectors", in "The Role of Plant Biotechnology in Plant Breeding", Report of the 1984 Plant Breeding Research Forum, Aug. 21–23 1984), Pioneer Hibred, page 177–192 (1985)). The T-DNA vector may be oncogenic (Hernalsteens et al, Nature, 287, 654 (1980)), partially disarmed (Barton et al, Cell, 32, 1033–1043 (1983)), fully disarmed (Zambryski et al, EMBO J., 2, 2143 (1983)), or may be based on artificial T-DNA vectors having synthetic T-DNA border-like sequences, (Wang et al, Cell, 38, 455 (1984). Some suitable disarmed vectors containing T-DNA border regions include pGA 436, pGA 437 and pGA 438, as are described in An et al., EMBO J. 4: 277–284 (1985), pMON120; see Fraley et al, Proc. Natl. Acad. Sci. USA, 80, 4803–4807 (1983) and pCIB10; Rothstein et al., Gene 53, 153–161 (1987). The transfer of T-DNA is usually accomplished by incubating Agrobacterium with plant cell protoplasts or wounded plant tissue, see Caplan et al, Science, 222, 815 (1983).

In addition to the chimeric gene coding for a *B. thuringiensis* or a *B. thuringiensis*-like toxin, the vectors preferably further comprise a DNA sequence that permits the selection or screening of cotton plant cells containing the vector in the presence of cells that do not contain the vector. Such selectably or screenable markers may naturally be present in the vector into which the chimeric gene of this invention is introduced, or may be introduced into the vector either before or after the chimeric gene is introduced. Alternatively, the selectable or screenable marker gene or a portion thereof may first be joined to the desired chimeric gene or any portion thereof and the combined genes or gene segments may be introduced as a unit into the vector. The selectable or screenable marker may itself be chimeric.

The preferred selectable marker is a gene coding for antibiotic resistance. The gene must be capable of expression in the cells to be transformed. The cells can be cultured in a medium containing the antibiotic, and those cells containing the vector, which have an enhanced ability to survive in the medium, are selected. Genes that confer resistance to chloramphenicol, kanamycin, G418, hygromycin or, in principle, any other antibiotic may be useful as a selectable marker.

Some examples of genes that confer antibiotic resistance include, for example, those coding for neomycin phosphotransferase (kanamycin resistance, Velten et al, EMBO J., 3, 2723–2730 (1984)); hygromycin phosphotransferase [hygromycin resistance, van den Elzen et al., Plant Molecular Biology, 5, 299–302 (1985)] and chloramephenicol acetyltransferase.

An example of a gene useful primarily as a screenable marker in tissue culture for identification of plant cells containing genetically engineered vectors is a gene that encodes an enzyme having a chromogenic substrate. For example, if the gene encodes the enzyme beta-galactosidase, the plant cells are plated on a tissue culture medium containing the chromogenic substrate Xgal (5-chloro-4-bromo-3-indolyl-beta-D-galactoside), and under appropriate conditions, plant cells containing copies of this gene are strained blue by the dye indigo which is released when beta-galactosidase cleaves Xgal.

Introduction of Genes into Plants

The introduction of chimeric genes into plants in accordance with the present invention may be carried out with any T-DNA-derived vector system capable of introducing genes into cotton plant cells from Agrobacteria. The vector system may, for example, be a cointegrate system (Comai et al., Plasmid, 10, 21, (1983); Zambryski et al., EMBO J., 2, 2143 (1983) for example the split-end vector system (Fraley et al, Bio/Technology, 3, 629 (1985) as described by Chilton, "Plant Gene Vectors", in "The Role of Plant Biotechnology in Plant Breeding", Report of the 1984 Plant Breeding Research Forum, Aug. 21–23, 1984, Pioneer Hibred, 177–192 (1985). The vector system may, on the other hand, be a binary system, de Framond et al, Bio/Technology, 1, 266 (1983); Hoekema et al, Nature, 303, 179 (1983), or a Ti plasmid engineered by homogenotization of the gene into the T-DNA, Matzke et al, J. Mol. Appl. Genet., 1, 39 (1981). A final possibility is a system wherein the T-DNA is on a plasmid and the virulence genes are on the chromosonal DNA.

The preferred T-DNA vector system is a binary vector system, and especially a system utilizing pCIB10 Rothstein et al., Gene, 53, 153–161 (1987). (See FIG. 10).

The introduction of heterologous genes by recombinant DNA manipulation into a binary vector system is described by Klee et al, Bio/Technology, 3, 637 (1985). The insertion of genes into a T-DNA vector may be by homologous recombination using a double recombination strategy, Matzke et al, J. Mol. Appl. Genet., 1, 39 (1981); single recombination strategy, Comai et al, Plasmid, 10, 21 (1983); Zambryski et al, EMBO J., 2, 2143 (1983); or a single recombination strategy with no repeats in the T-DNA, Fraley et al, Bio/Technology, 3, 629 (1985) as described by Chilton, "Plant Gene Vectors", in "The Role of Plant Biotechnology in Plant Breeding", Report of the 1984 Plant Breeding Research Forum, Aug. 21–23, 1984, Pioneer Hibred, pages 177–192 (1985).

If the vectors containing the chimeric gene are not assembled in Agrobacterium, they may be introduced into Agrobacterium by methods known in the art. These methods include transformation and conjugation.

Transformation involves adding naked DNA to bacteria. Agrobacterium may be made susceptible to the introduction of naked DNA by freezing and thawing. The transformation of Agrobacterium is described by Holsters et al, Mol. Gen. Genet., 163, 181 (1978).

Conjugation involves the mating of a cell containing the desired vector, usually E. coli, with Agrobacterium. This method is described by Comai et al, Plasmid. 10, 21 (1983), and Chilton et al, Genetics, 83, 609 (1976).

The Agrobacterium spp. may be any strain of Agrobacterium capable of introducing genes into cotton plant cells. Some suitable examples include A. tumefaciens, A. rhizogenes, and A. radiobacter.

Genes are introduced into cotton plant cells by the method described in Phytogen's U.S. patent application Ser. No. 122,200, filed Nov. 18, 1987.

Transformed cotton plant cells containing the chimeric gene may be maintained in culture or may be regenerated into living plants. Expression is preferably of sufficient efficiency to render the plant cells insecticidal.

The medium capable of sustaining a particular plant cell in culture depends on the particular variety of cotton plant cell. For example, some suitable media include approximately 10 mg/l of 2,4 dichlorophenoxyacetic acid and either Murashige and Skoog inorganic salts [Physiol. Plant, 15: 473–497 (1962)] or Gamborg B-5 inorganic salts [Exp. Cell Res., 50: 151–158 (1968)].

The invention also includes living cotton plants, the cells of which contain the chimeric gene that expresses the polypeptide having substantially the insect toxicity properties of B. thuringiensis crystal protein.

Insecticides

The plant cells of this invention contain the chimeric gene and may be used to produce the polypeptide having substantially the insect toxicity of *B. thuringiensis*. The plant cells per se may constitute the insecticide. Plant cells used directly as insecticides may be cultured plant cells, or may be components of a living plant.

The toxin may also be isolated from the plant cells by known methods such as, for example, by extraction or chromatography. The extract, may be the total plant cell extract, a partially purified extract, or a pure preparation of the polypeptide. Any such extract or chromatographic isolate may be used in the same way as crystal protein from *B. thuringiensis*; see, for example, Deacon, Aspects of Microbiology, 7, Cole et al, ed, American Society for Microbiology (1983) and Miller et al, Science, 219, 715 (1983).

The present invention also includes a method for killing Lepidopteran larvae comprising feeding the larvae an insecticidal amount of cotton plant cells that contain the chimeric gene of the invention. The plant cells may be cultured plant cells, or may be components of living plants.

The present invention further includes cotton seeds of plants genetically engineered in accordance with this invention as long as the seeds contain the inserted gene and the desirable trait resulting therefrom. Progeny of plants produced by the method of this invention, including sexual and vegatative progeny, are futher embodiments. Sexual progeny may result from selfing or cross pollination.

EXAMPLES

EXAMPLE 1

General Recombinant DNA Techniques

Since many of the recombinant DNA techniques used in this invention are routine for those skilled in the art, a brief description of these commonly used techniques is included here rather than at each instance where they appear below. Except where noted, all of these routine procedures are described in the reference by Maniatis et al., "Molecular Cloning, A Laboratory Manual" (1982).

A. Restriction endonuclease digestions. Typically, DNA is present in the reaction mixture at approximately 50–500 ug/ml in the buffer solution recommended by the manufacturer, New England Biolabs, Beverly, Mass., 2–5 units of restriction endonucleases are added for each ug of DNA, and the reaction mixture incubated at the temperature recommended by the manufacturer for one to three hours. The reaction is terminated by heating to 65° C. for ten minutes or by extraction with phenol, followed by precipitation of the DNA with ethanol. This technique is also described on pages 104–106 of the Maniatis et al., reference.

B. Treatment of DNA with polymerase to create flush ends. DNA fragments are added to a reaction mixture at 50 . 500 ug/ml in the buffer recommended by the manufacturer, New England Biolabs. The reaction mixture contains all four deoxynucleotide triphosphates at a concentration of 0.2 mM. The reaction is incubated at 15° C. for 30 minutes, and then terminated by heating to 65° C. for ten minutes. For fragments produced by digestion with restriction endonucleases that create 5'-protruding ends, such as EcoRI and BamHI, the large fragment, or Klenow fragment, of DNA polymerase is used. For fragments produced by endonucleases that produce 3'-protruding ends, such as PstI and SacI, T4 DNA polymerase is used. Use of these two enzymes is described on pages 113–121 of the Maniatis et al. reference.

C. Agarose gel electrophoresis and purification of DNA fragments from gels. Agarose gel electrophoresis is performed in a horizontal apparatus as described on pages 150–163 of Maniatis et al. reference. The buffer used is the Tris-borate buffer described therein. DNA fragments are visualized by staining with 0.5 ug/ml ethidium bromide, which is either present in the gel and tank buffer during electrophoresis or added following electrophoresis. DNA is visualized by illumination with short-wavelength or long-wavelength ultraviolet light. When the fragments are to be isolated from the gel, the agarose used is the low gelling-temperature variety, obtained from Sigma Chemical, St. Louis, Mo. After electrophoresis, the desired fragment is excised, placed in a plastic tube, heated to 65° C. for approximately 15 minutes, then extracted with phenol three times and precipitated with ethanol twice. This procedure is slightly modified from that described in the Maniatis et al. reference at page 170.

D. Addition of synthetic linker fragments to DNA ends. When it is desired to add a new restriction endonuclease site to the end of a DNA molecule, that molecule is first treated with DNA polymerase to create flush ends, if necessary, as described in the section above. Approximately 0.1–1.0 ug of this fragment is added to approximately 100 ng of phosphorylated linker DNA, obtained from New England Biolabs, in a volume of 20–30 ul containing 2 ul of T4 DNA ligase, from New England Biolabs, and 1 mM ATF in the buffer recommended by the manufacturer. After incubation overnight at 15° C., the reaction is terminated by heating the 65° C. for ten minutes. The reaction mixture is then diluted to approximately 100 ul in a buffer suitable for the restriction endonuclease that cleaves at the synthetic linker sequence, and approximately 50–200 units of this endonuclease are added. The mixture is incubated at the appropriate temperature for 2–6 hours, then the fragment is subjected to agarose gel electrophoresis and the fragment purified as described above. The resulting fragment will now have ends with termini produced by digestion with the restriction endonuclease. These termini are usually cohesive, so that the resulting fragment is now easily ligated to other fragments having the same cohesive termini.

E. Removal of 5'-terminal phosphates from DNA fragments. During plasmid cloning steps, treatment of the vector plasmid with phosphatase reduces recirculatization of the vector (discussed on page 13 of Maniatis et al. reference). After digestion of the DNA with the appropriate restriction endonuclease, one unit of calf intestine alkaline phosphatase, obtained from Boehringer-Mannheim, Indianapolis, Ind., is added. The DNA is incubated at 37° C. for one hour, then extracted twice with phenol and precitated with ethanol.

F. Ligation of DNA fragments. When fragments having complementary cohesive termini are to be joined, approximately 100 ng of each fragment are incubated in a reaction mixture of 20–40 ul containing approximately 0.2 units of T4 DNA ligase from New England Biolabs in the buffer recommended by the manufacturer. The incubation is conducted 1–20 hours at 15° C. When DNA fragments having flush ends are to be joined, they are incubated as above, except the amount of T4 DNA ligase is increased to 2–4 units.

G. Transformation of DNA into *E. coli*. *E. coli* strain HB101 is used for most experiments. DNA is introduced into *E. coli* using the calcium chloride procedure described by Maniatis et al. on pages 250–251. Transformed bacteria are selectively able to grow on medium containing appropriate antibiotics. This selective ability allows the desired bacteria to be distinguished from host bacteria not receiving transforming DNA. Determining what antibiotic is appropriate is routine, given knowledge of the drug resistance genes present on incoming transforming DNA and the drug sensitivity of the host bacteria. For example, where the host bacteria is know to be sensitive to ampicillin and there is a functional drug resistance gene for ampicillin on the incoming transforming DNA, ampicillin is an appropriate antibiotic for selection of transformants.

H. Screening *E. coli* for plasmids. Following transformation, the resulting colonies of *E. coli* are screened for the presence of the desired plasmid by a quick plasmid isolation procedure. Two convenient procedures are described on pages 366–369 of Maniatis et al. reference.

I. Large scale isolation of plasmid DNA. Procedures for isolating large amounts of plasmids in *E. coli* are found on pages 88–94 of the Maniatis et al. reference.

J. Cloning into M13 phage vectors. In the following description, it is understood that the double-stranded replicative form of the phage M13 derivatives is used for routine procedures such as restriction endonuclease digestions, ligations, etc;

EXAMPLE 2

Construction of Chimeric Gene in Plasmid pBR322

Figure 2:
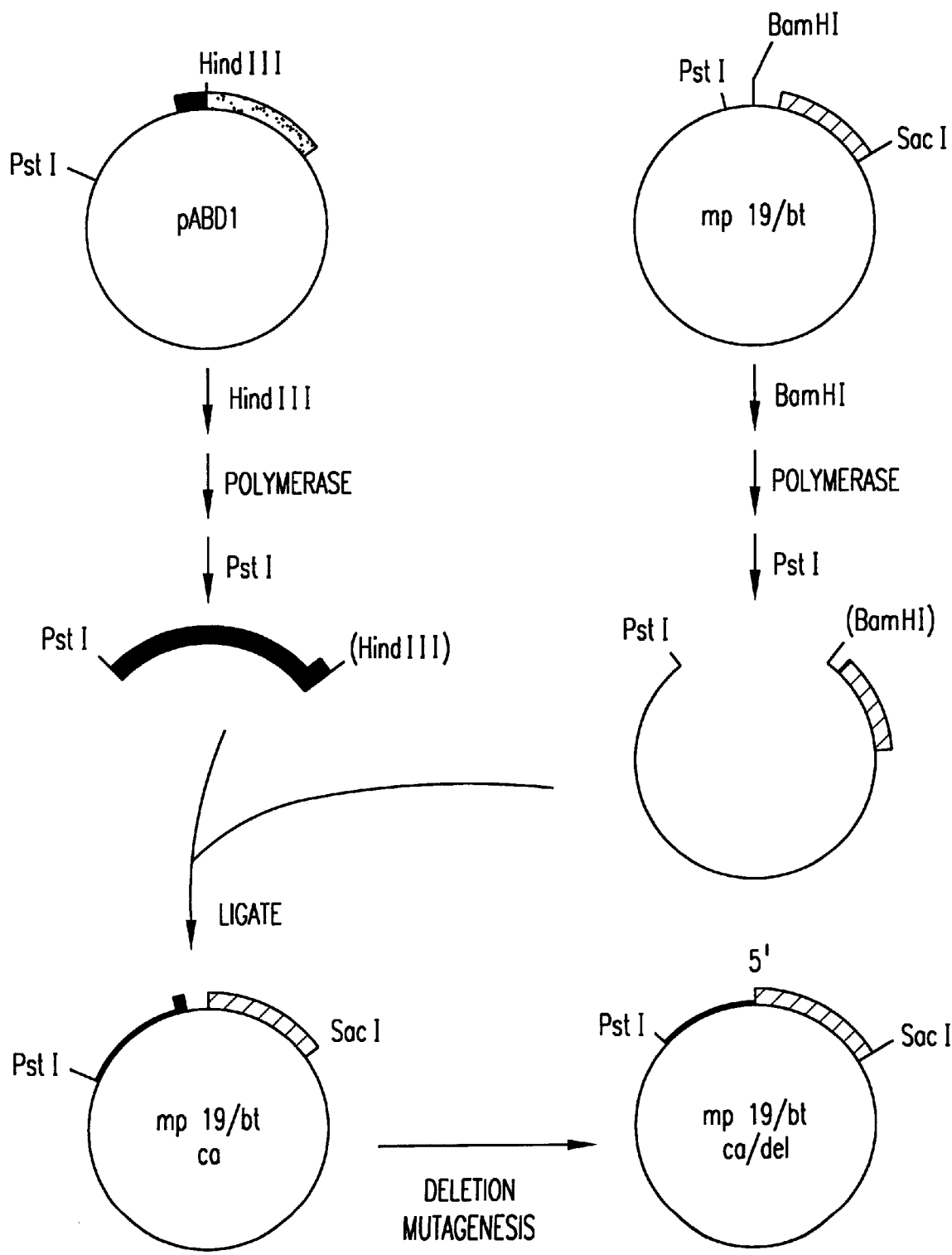
FIG. 2. Construction of mp 19/Bt ca/del, a plasmid containing the CaMV gene VI promoter fused to the 5' end of Bt protoxin coding sequence.
Figure 3:
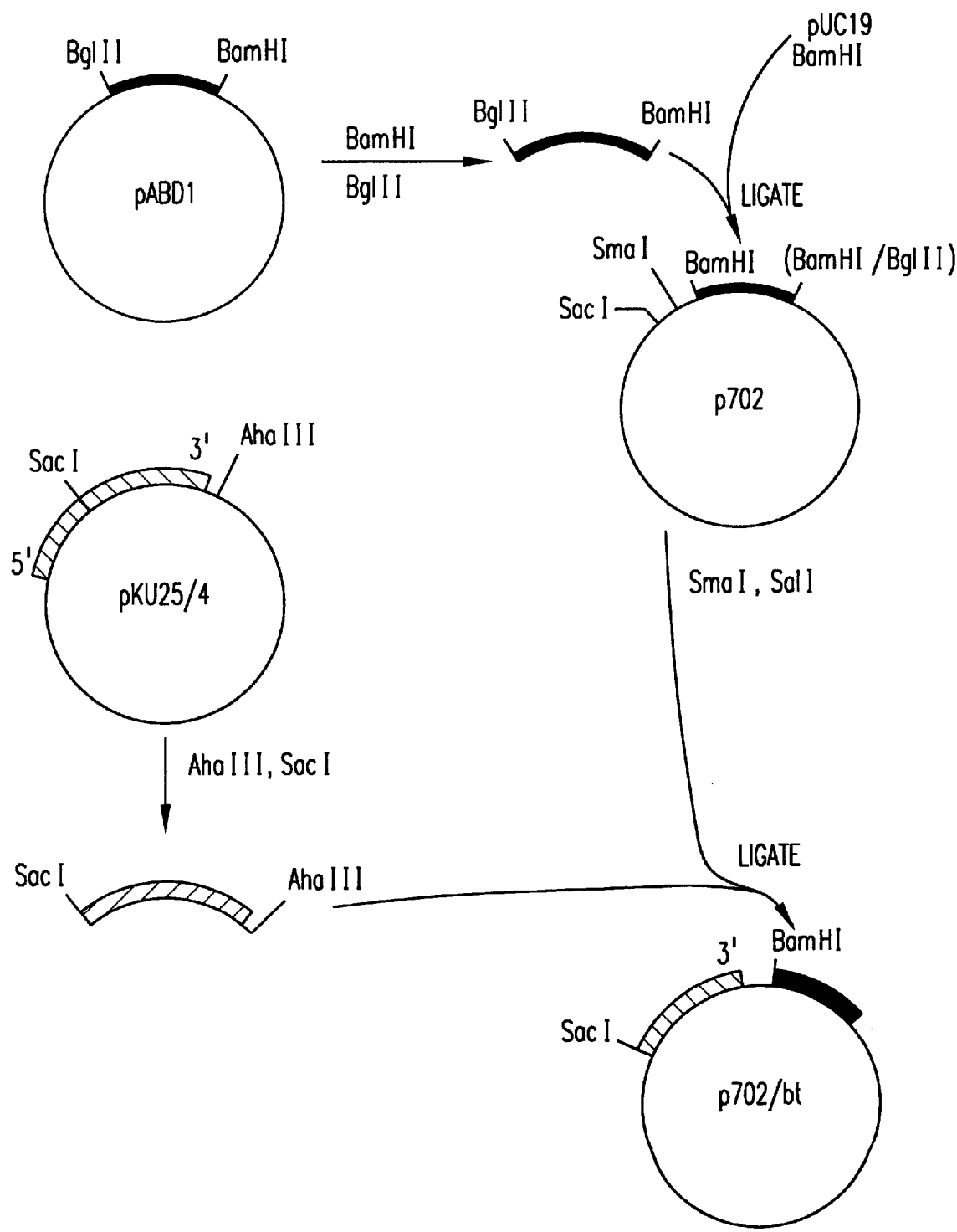
FIG. 3. Construction of p702/Bt, a plasmid having the 3' coding region of the protoxin fused to the CaMV transcription termination signals.
Figure 6:
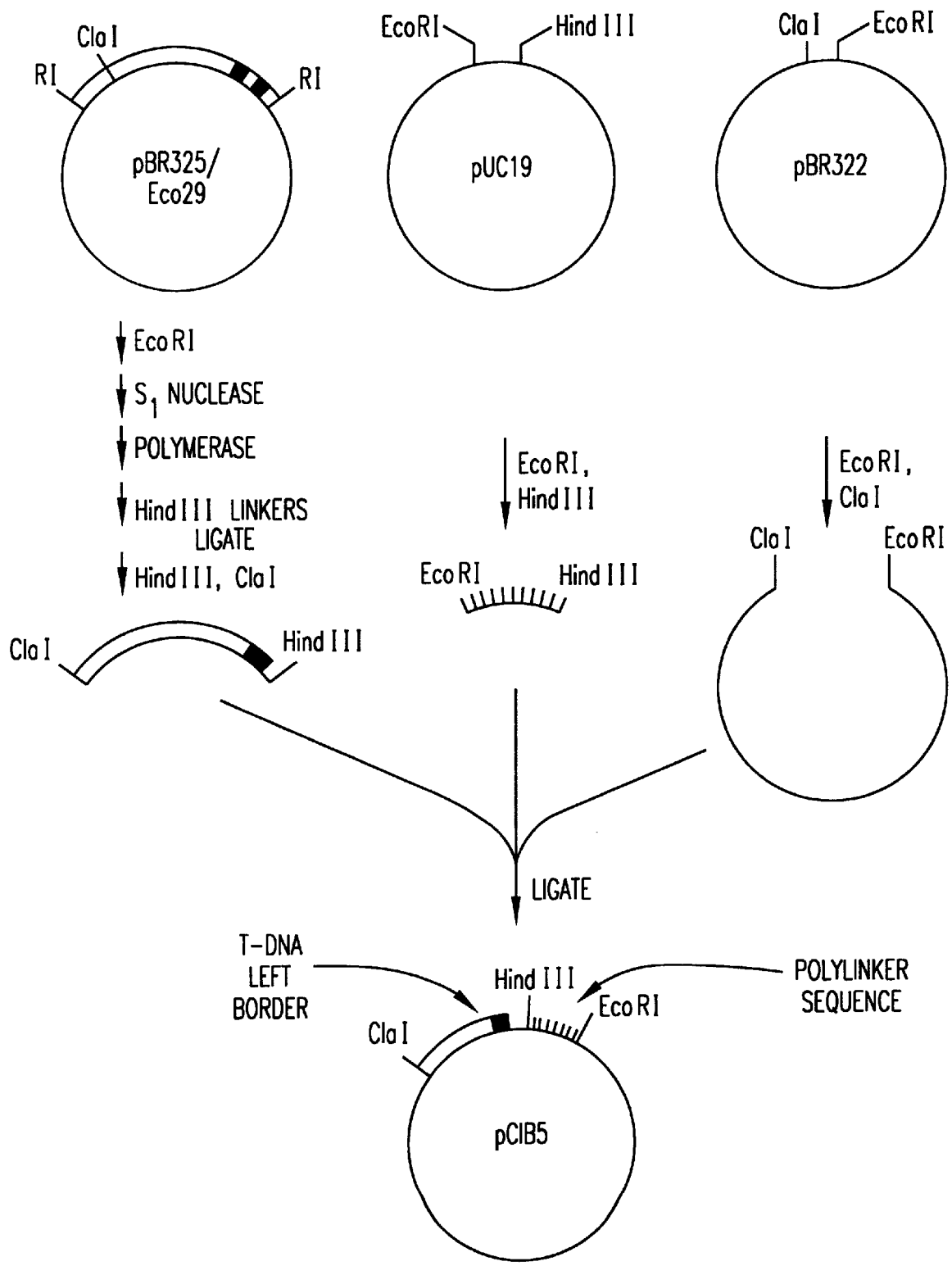
FIG. 6. Construction of pCIB 5.

In order to fuse the CaMV gene VI promoter and protoxin coding sequences, a derivative of phage vector mp19 (Yanisch-Perron et al., Gene 33: 103–119 (1985) is constructed. The following steps are shown in FIGS. 1 and 2. First, a DNA fragment containing approximately 155 nucleotides 5' to the protoxin coding region and the adjacent approximately 1346 nucleotides of coding sequence are inserted into mp19. Phage mp19 ds rf (double-stranded replicative form) DNA is digested with restriction endonucleases SacI and SmaI and the approximately 7.2-kbp vector fragment is purified after electrophoresis through low-gelling temperature agarose by standard procedures. Plasmid pKU25/4, containing approximately 10 kbp (kilobase pairs) of *Bacillus thuringiensis* DNA, including the protoxin gene, is obtained from Dr. J. Nueesch, CIBA-GEIGY Ltd., Basel, Switzerland. The nucleotide sequence of the protoxin gene present in plasmid pKU25/4 is shown in formula I above. Plasmid pKU25/4 DNA is digested with endonucleases HpaI and SacI, and a 1503 bp fragment (containing nucleotides 2 to 1505 in Formula I) is purified as above. (This fragment contains approximately 155 bp of bacteria promoter sequences and approximately 1346 bp of the start of the protoxin coding sequence.) Approximately 100 ng of each fragment is then mixed, T4 DNA ligase added, and incubated at 15° C. overnight. The resulting mixture is transformed into *E. coli* strain HB101, mixed with indicator bacteria *E. coli* JM 101 and plated as described (Messing, J., Meth. in Enzym. 101: 20–78 [1983]). One phage called mp19/bt is used for further construction below.

Next, a fragment of DNA containing the CaMV gene VI promoter, and some of the coding sequences for gene VI, is inserted into mp19/bt. Phage mp19/bt ds rf DNA is digested with BamHI, treated with the large fragment of DNA polymerase to create flush ends and recleaved with endonuclease PstI. The larger vector fragment is purified by electrophoresis as described above. Plasmid pABD1 is described in Paszkowski et al., EMBO J. 3, 2717–2722, (1984). Plasmid pABDl DNA is digested with PstI and HindIII. The fragment approximately 465 bp long containing the CaMV gene VI promoter and approximately 75 bp of gene VI coding sequence is purified. The two fragments are ligated and plated as described above. One of the resulting recombinant phages, called mp19/btca is used in the following experiment.

Phage mP19/btca contains CaMV gene VI promoter sequences, a portion of the gene VI coding sequence, approximately 155 bp of *Bacillus thuringiensis* DNA upstream of the protoxin coding sequence, and approximately 1346 bp of the protoxin coding sequence. To fuse the CaMV promoter sequences precisely to the protoxin coding sequences, the intervening DNA is deleted using oligonucleotide-directed mutagenesis of mp19/btca DNA. A DNA oligonucleotide with the sequence (5') TTCGGAT-TGTTATCCATGGTTGGAGGTCTGA (3') is synthesized by routine procedures using an Applied Biosystems DNA Synthesizer. This oligonucleotide is complimentary to those sequences in phage mp19/btca DNA at the 3' end of the CaMV promoter (nucleotides 5762 to 5778 in Hohn, Current Topics in Microbiology and Immunology 96, 193–235 (1982) and the beginning of the protoxin coding sequence (nucleotides 156 to 172 in formula I above). The general procedure for the mutagenesis is that described in Zoller and Smith, Meth. in Enzym. 100: 468–500 (1983). Approximately five ug of single-stranded phage mp19/btca DNA is mixed with 0.3 ug of phosphorylated oligonucleotide in a volume of 40 ul. The mixture is heated to 65° C. for 5 min, cooled to 50° C., and slowly cooled to 4° C. Next, buffer, nucleotide triphosphates, ATP, T4 DNA ligase and large fragment of DNA polymerase are added and incubated overnight at 15° C. as described [see Zoller and Smith, Meth. in Enzym. 100: 468–500 (1983)]. After agarose gel electrophoresis, circular double-stranded DNA is purified and transfected into *E. coli* strain JM101. The resulting plaques are screened for sequences that hybridize with $^{32}P$-labeled oligonucleotide, and phage are analyzed by DNA restriction endonuclease analysis. Among the resulting phage clones will be ones which have correctly deleted the unwanted sequences between the CaMV gene VI promoter and the protoxin coding sequence. This phage is called mp19/btca/del (see FIG. 2).

Next, a plasmid is constructed in which the 3' coding region of the protoxin gene is fused to CaMV transcription termination signals. The following steps are shown in FIG. 3. First, plasmid pABDl DNA is digested with endonucleases BamHI and BglII and a 0.5 kbp fragment containing the CaMV transcription terminator sequences is isolated. Next plasmid pUC19, Yanisch-Perron et al., Gene 33: 103–119 (1985) is digested with BamHI, mixed with the 0.5 kbp fragment and incubated with T4 DNA ligase. After transformation of the DNA into *E. coli* strain HB101, one of the resulting clones, called plasmid p702, is obtained which has the structure shown in FIG. 3. Next, plasmid p702 DNA is cleaved with endonucleases SacI and SmaI, and the larger, approximately 3.2 kbp fragment is isolated by gel electrophoresis. Plasmid pKU25/4 DNA is digested with endonucleases AhaIII and SacI, and the 2.3-kbp fragment (nucleotides 1502 to 3773 in formula I above) containing the 3' portion of the protoxin coding sequence (nt 1504 to 3773 of the sequence shown in Formula I) is isolated after gel electrophoresis. These two DNA fragments are mixed, incubated with T4 DNA ligase and transformed into *E. coli* strain HB101. The resulting plasmid is p702/bt (FIG. 3).

Finally, portions of phage mp19/btca/del ds rf DNA and plasmid p702/bt are joined to create a plasmid containing the complete protoxin coding sequence flanked by CaMV promoter and terminator sequences (see FIG. 4). Phage mp19/btca/del DNA is digested with endonucleases SacI and SphI, and a fragment of approx. 1.75 kbp is purified following agarose gel electrophoresis. Similarly, plasmid p702/bt DNA is digested with endonucleases SacI and SalI and a fragment of approximately 2.5 kbp is isolated. Finally, plasmid pBR322 DNA (Bolivar et al., Gene 2: 95–113 (1977) is digested with SalI and SphI and the larger 4.2-kbp fragment isolated. All three DNA fragments are mixed and incubated with T4 DNA ligase and transformed into *E. coli* strain HB101. The resulting plasmid, pBR322/bt14 is a derivative of pBR322 containing the CaMV gene VI promoter and translation start signals fused to the bacillus thuringiensis crystal protein coding sequence, followed by CaMV transcription termination signals (shown in FIG. 4).

3. Construction of a Ti plasmid-derived vector.

The vector pCIB10 (Rothstein et al., Gene, 53, 153–161 (1987)) is a Ti-plasmid-derived vector useful for transfer of the chimeric gene to plants via *Agrobacterium tumefaciens*. The vector is derived from the broad host range plasmid pRK252, which may be obtained from Dr. W. Barnes, Washington University, St. Louis, Mo. The vector also contains a gene for kanamycin resistance in Agrobacterium, from Tn903, and left and right T-DNA border sequences from the Ti plasmid pTiT37. Between the border sequences are the polylinker region from the plasmid pUC18 and a chimeric gene that confers kanamycin resistance in plants.

First, plasmid pRK252 is modified to replace the gene conferring tetracycline-resistance with one conferring resistance to kanamycin from the transposon Tn903 [Oka, et al., J. Mol. Biol., 147, 217–226 (1981)], and is also modified by replacing the unique EcoRI site in pRK252 with a Bg1II site (see FIG. 5 for a summary of these modifications). Plasmid pRK252 is first digested with endonucleases SalI and SmaI, then treated with the large fragment of DNA polymerase I to create flush ends, and the large vector fragment purified by agarose gel electrophoresis. Next, plasmid p368, which contains Tn903 on an approximately 1050 bp BamHI fragment, is digested with endonuclease BamHI, treated with the large fragment of DNA polymerase, and an approximately 1050-bp fragment is isolated after agarose gel electrophoresis; this fragment contains the gene from transposon Tn903 which confers resistance to the antibiotic kanamycin [Oka et al., J. Mol. Biol., 147, 217–226 (1981)]. Plasmid p368 has been deposited with ATCC, accession number 67700. Both fragments are then treated with the large fragment of DNA polymerase to create flush ends. Both fragments are mixed and incubated with T4 DNA ligase overnight at 15° C. After transformation into *E. coli* strain HB101 and selection for kanamycin resistant colonies, plasmid pRK252/Tn903 is obtained (see FIG. 5).

Plasmid pRK252/Tn903 is digested at its unique EcoRI site, followed by treatment with the large fragment of *E. coli* DNA polymerase to create flush ends. This fragment is added to synthetic Bg1II restriction site linkers, and incubated overnight with T4 DNA ligase. The resulting DNA is digested with an excess of Bg1II restriction endonuclease and the larger vector fragment purified by agarose gel electrophoresis. The resulting fragment is again incubated with T4 DNA ligase to recircularize the fragment via its newly-added Bg1II cohesive ends. Following transformation into *E. coli* strain HB101, plasmid pRK252/Tn903/Bg1II is obtained (see FIG. 5).

A derivative of plasmid pBR322 is constructed which contains the Ti plasmid T-DNA borders, the polylinker region of plasmid pUC19, and the selectable gene for kanamycin resistance in plants (see FIG. 6). Plasmid pBR325/Eco29 contains the 1.5-kbp EcoRI fragment from the nopaline Ti plasmid pTiT37. This fragment contains the T-DNA left border sequence; Yadav et al., Proc. Natl. Acad. Sci. USA, 79, 6322–6326 (1982). To replace the EcoRI ends of this fragment with HindIII ends, plasmid pBR325/Eco29 DNA is digested with EcoRI, then incubated with nuclease S1, followed by incubation with the large fragment of DNA polymerase to create flush ends, then mixed with synthetic HindIII linkers and incubated with T4 DNA ligase. The resulting DNA is digested with endonucleases ClaI and an excess of HindIII, and the resulting 1.1-kbp fragment containing the T-DNA left border is purified by gel electrophresis. Next, the polylinker region of plasmid pUC19 is isolated by digestion of the plasmid DNA with endonucleases EcoRI and HindIII and the smaller fragment (approx. 53 bp) is isolated by agarose gel electrophresis. Next, plasmid pBR322 is digested with endonucleases EcoRI and ClaI, mixed with the other two isolated fragments, incubated with T4 DNA ligase and transformed into *E. coli* strain HB101. The resulting plasmid, pCIB5, contains the polylinker and T-DNA left border in a derivative of plasmid pBR322 (see FIG. 6).

Figure 7:
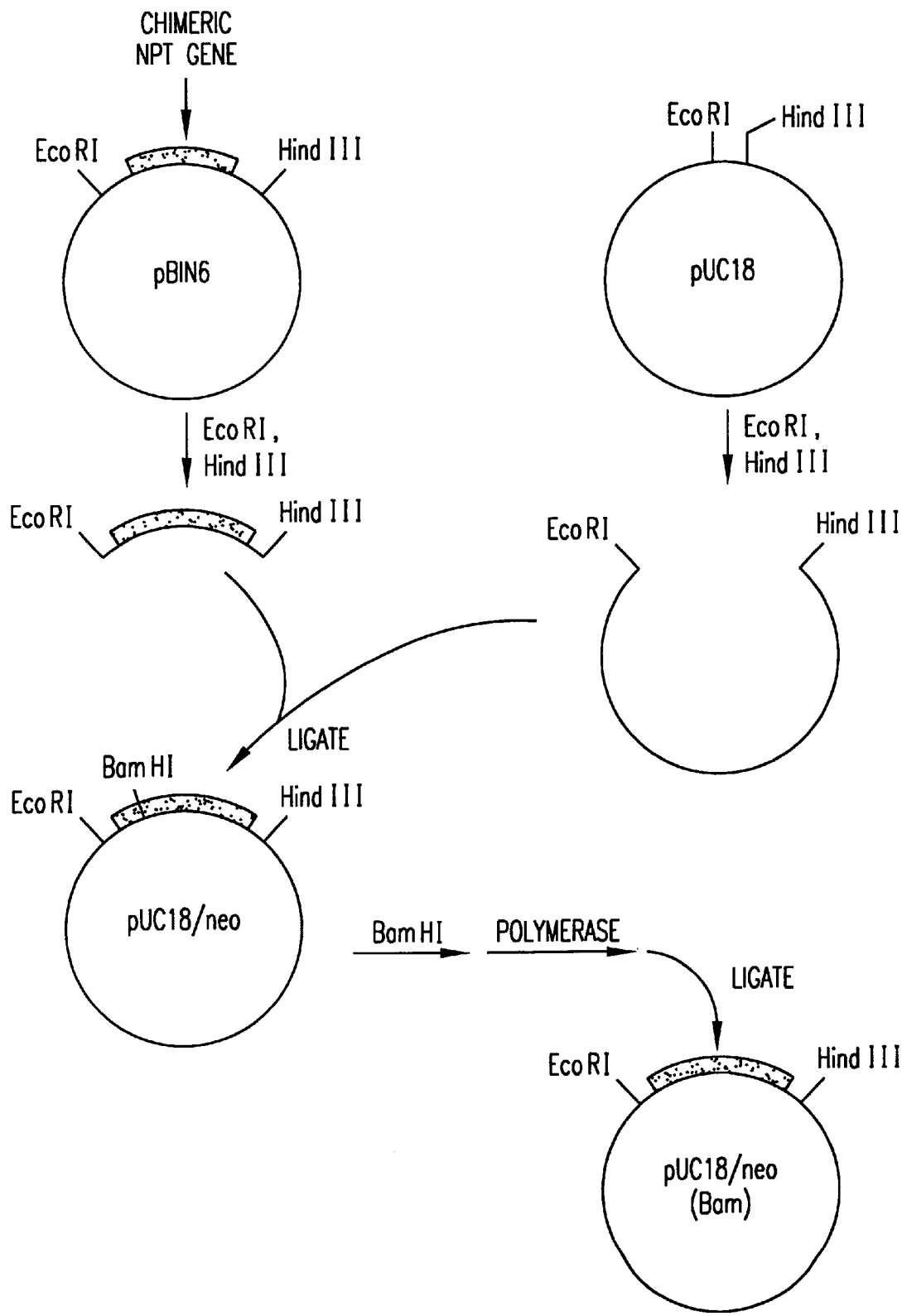
FIGS. 7 & 8. Construction of pCIB 4.
Figure 8:
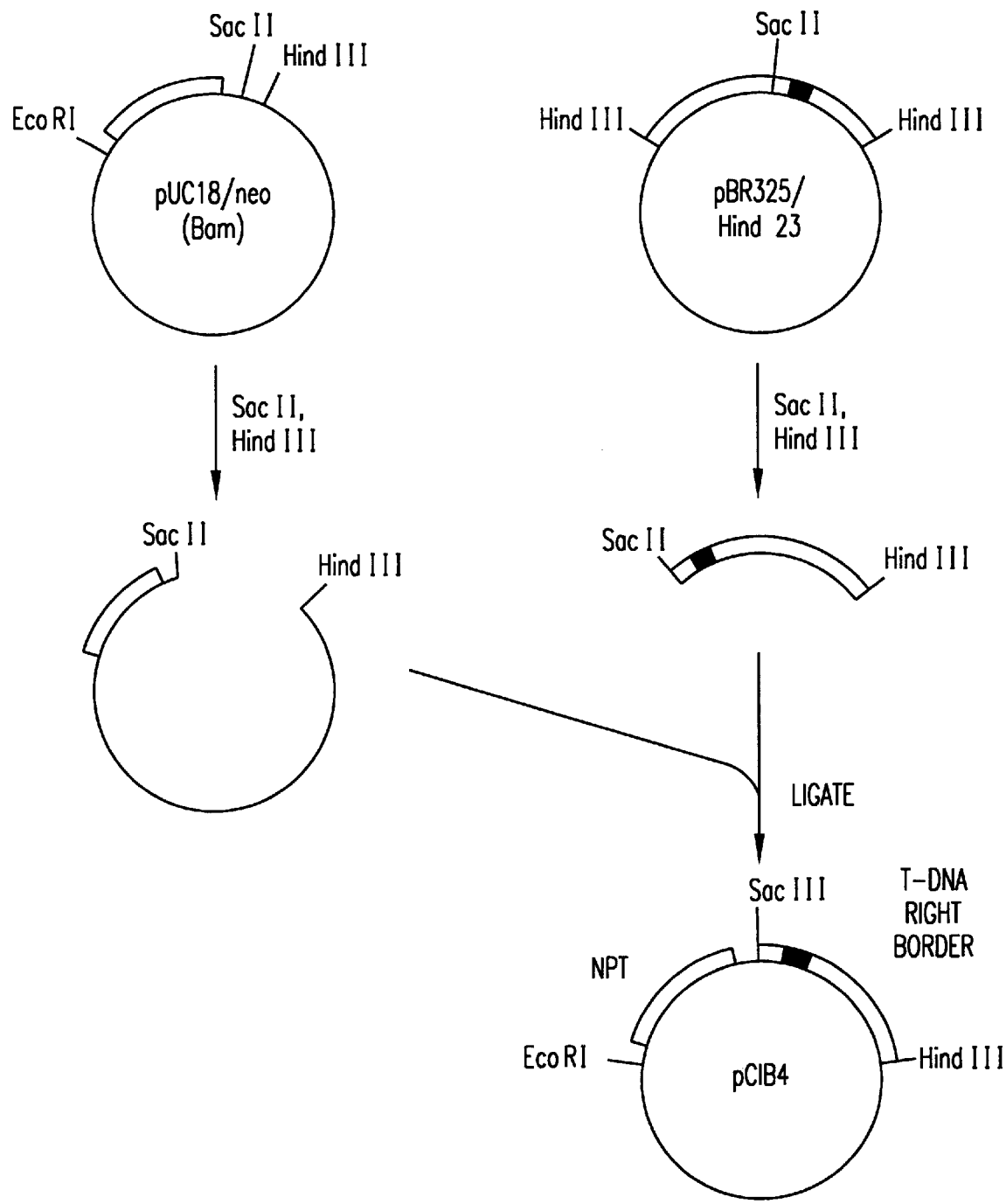

A plasmid containing the gene for expression of kanamycin resistance in plants is constructed (see FIGS. 7 and 8). Plasmid Bin6 is obtained from Dr. N. Bevan, Plant Breeding Institute, Cambridge, UK. This plasmid is described in the reference by Bevan, Nucl. Acids Res., 12, 8711–8721 (1984). Plasmid Bin6 DNA is digested with EcoRI and HindIII and the fragment approximately 1.5 kbp in size containing the chimeric neomycin phosphotransferase (NPT) gene is isolated and purified following agarose gel electrophoresis. This fragment is then mixed with plasmid pUC18 DNA which has been cleaved with endonucleases EcoRI and HindIII. Following incubation with T4 DNA ligase, the resulting DNA is transformed into *E. coli* strain HB101. The resulting plasmid is called pUC18/neo. This plasmid DNA contains an unwanted BamHI recognition sequence between the neomycin phosphotransferase gene and the terminator sequence for nopaline synthase; see Bevan, Nucl. Acids Res., 12, 8711–8721 (1984). To remove this recognition sequence, plasmid pUC18/neo is digested with endonuclease BamHI, followed by treatment with the large fragment of DNA polymerase to create flush ends. The fragment is then incubated with T4 DNA ligase to recircularize the fragment, and is transformed into *E. coli* strain HB101. The resulting plasmid, pUC18/neo(Bam) has lost the BamHI recognition sequence.

The T-DNA right border sequence is then added next to the chimeric NPT gene (see FIG. 8). Plasmid pBR325/Hind23 contains the 3.4-kbp HindIII fragment of plasmid pTiT37. This fragment contains the right T-DNA border sequence; Bevan et al., Nucl. Acids Res., 11, 369–385 (1983). Plasmid pBR325/Hind23 DNA is cleaved with endonucleases SacII and HindIII, and a 1.0 kbp fragment containing the right border is isolated and purified following agarose gel electrophoresis. Plasmid pUC18/neo(Bam) DNA is digested with endonucleases SacII and HindIII and the 4.0 kbp vector fragment is isolated by agarose gel electrophoresis. The two fragments are mixed, incubated with T4 DNA ligase and transformed into *E. coli* strain HB101. The resulting plasmid, pCIB4 (shown in FIG. 8), contains the T-DNA right border and the plant-selectable marker for kanamycin resistance in a derivative of plasmid pUC18.

Figure 9:
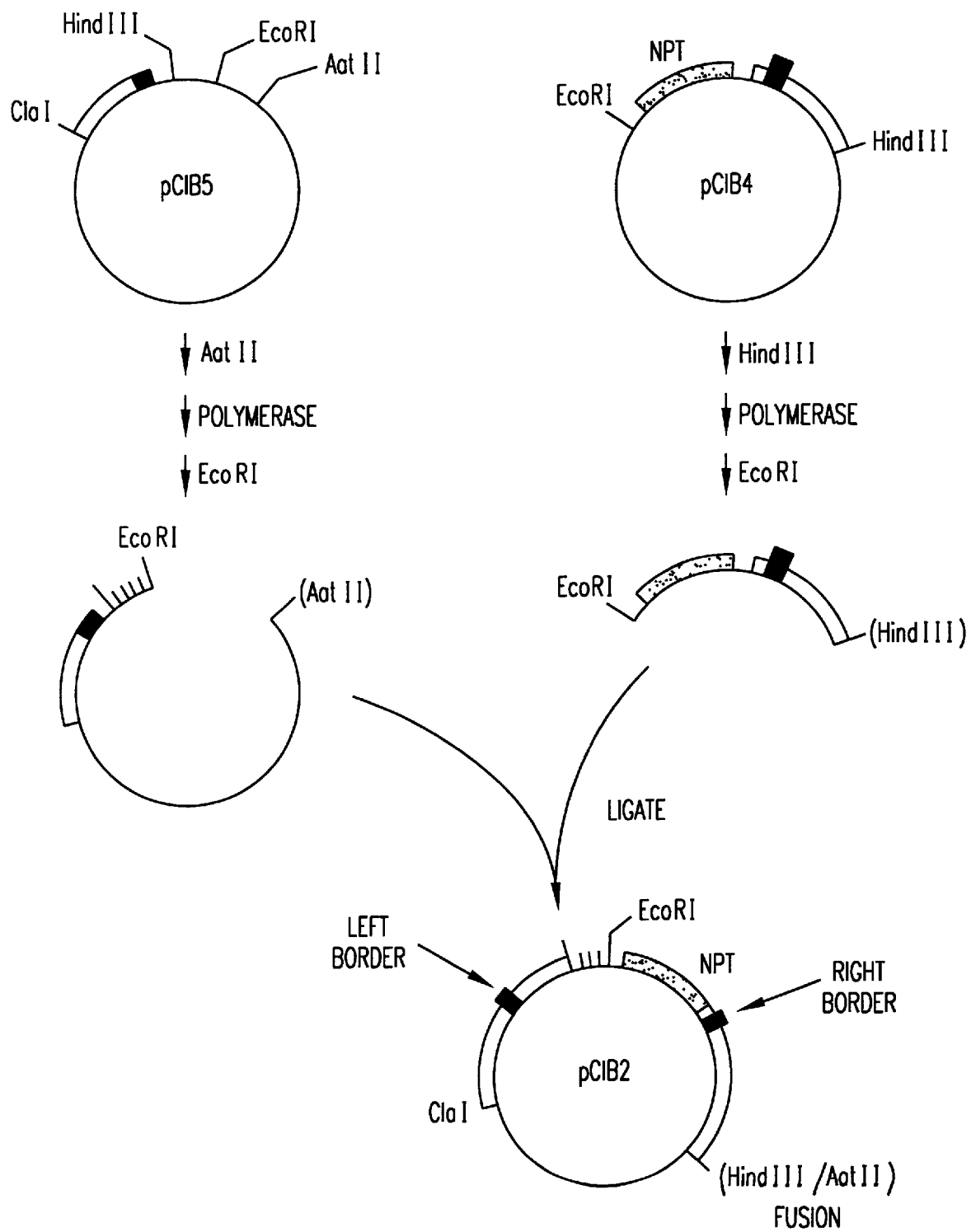
FIG. 9. Construction of p CIB 2.

Next, a plasmid is constructed which contains both the T-DNA left and right borders, with the plant selectable kanamycin-resistance gene and the polylinker of pUC18 between the borders (shown in FIG. 9). Plasmid pCIB4 DNA is digested with endonuclease HindIII, followed by treatment with the large fragment of DNA polymerase to create flush ends, followed by digestion with endonuclease EcoRI. The 2.6-kbp fragment containing the chimeric kanamycin-resistance gene and the right border of T-DNA is isolated by agarose gel electrophoresis. Plasmid PCIB5 DNA is digested with endonuclease AatII, treated with T4 DNA polymerase to create flush ends, then cleaved with endonuclease EcoRI. The larger vector fragment is purified by agarose gel electrophoresis, mixed with the pCIB4 fragment, incubated with T4 DNA ligase, and transformed into *E. coli* Strain HB101. The resulting plasmid, pCIB2 (shown in FIG. 9) is a derivative of plasmid pBR322 containing the desired sequences between the two T-DNA borders.

Figure 5:
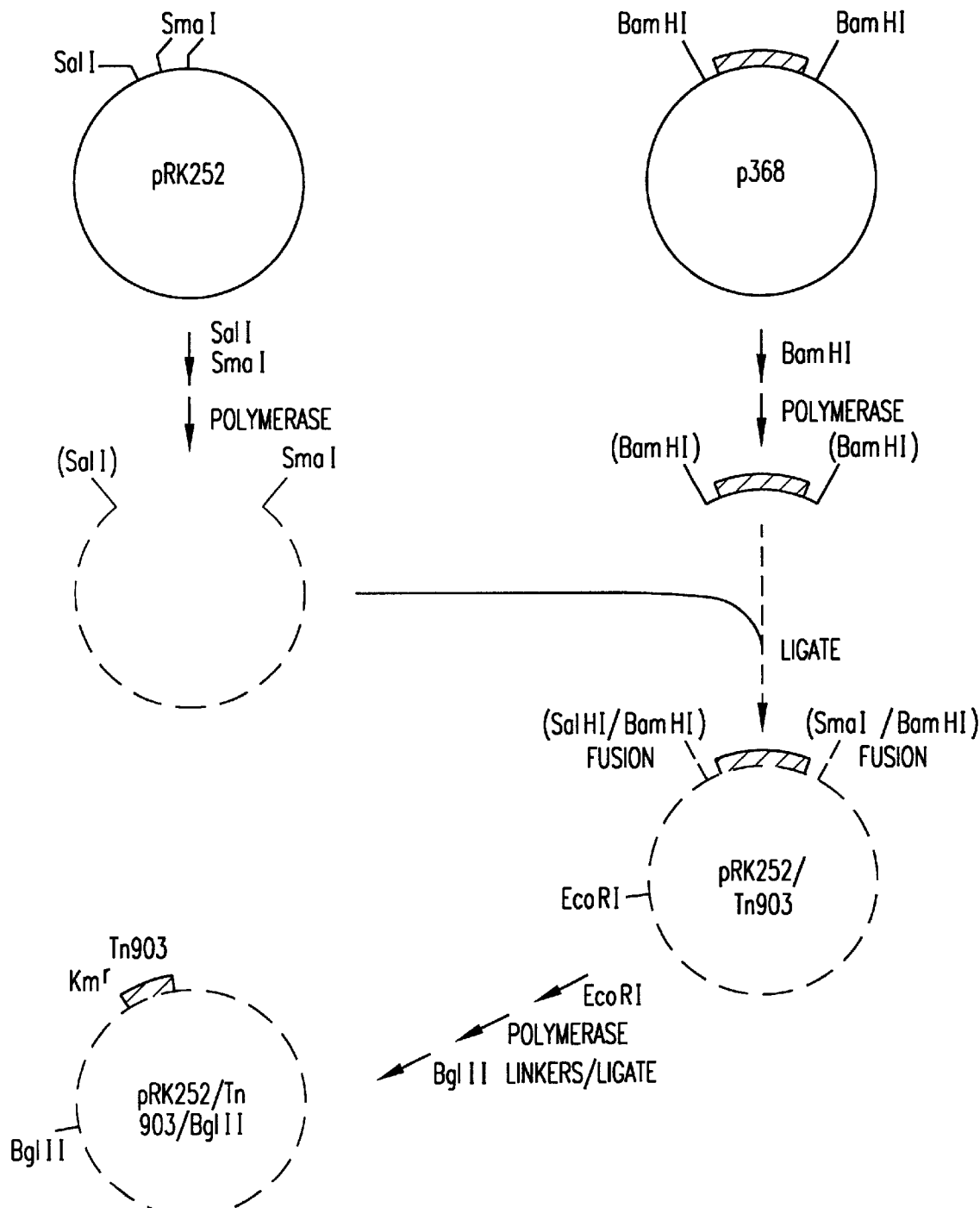
FIG. 5. Construction of pRK252/Tn903/BglII.
Figure 10:
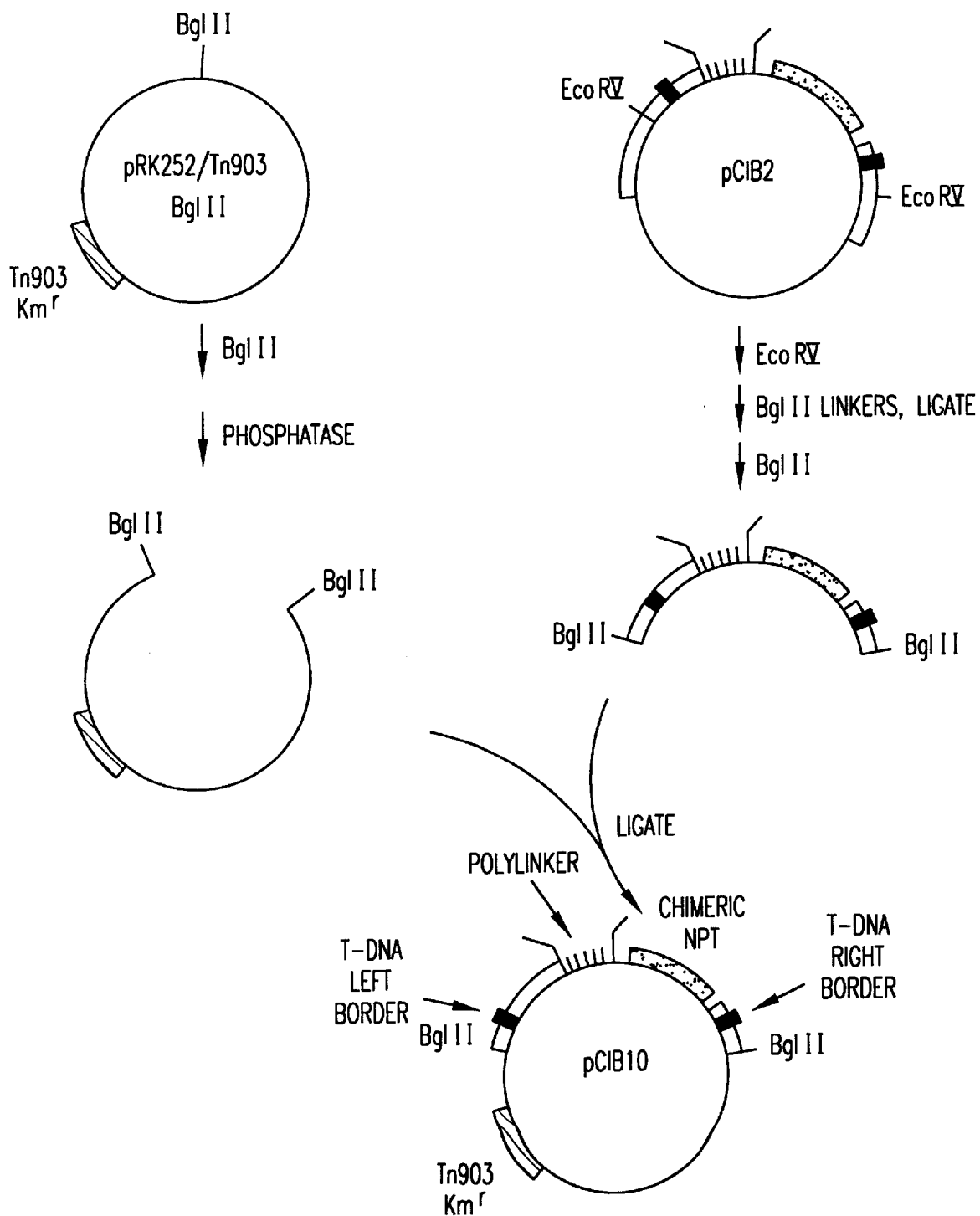
FIG. 10. Construction of pCIB 10, a broad host range plasmid containing T-DNA borders and gene for plant selection.

The following steps complete construction of the vector pCIB10, and are shown in FIG. 10. Plasmid pCIB2 DNA is digested with endonuclease EcoRV, and synthetic linkers containing BglII recognition sites are added as described above. After digestion with an excess of BglII endonuclease, the approximately 2.6-kbp fragment is isolated after agarose gel electrophoresis. Plasmid pRK252/Tn903/BglII, described above (see FIG. 5), is digested with endonuclease BglII and then treated with phosphatase to prevent recircularization. These two DNA fragments are mixed, incubated with T4 DNA ligase and transformed into *E. coli* strain HB101. The resulting plasmid is the completed vector, pCIB10.

EXAMPLE 4

Insertion of the Chimeric Protoxin Gene into Vector pCIB10

Figure 11:
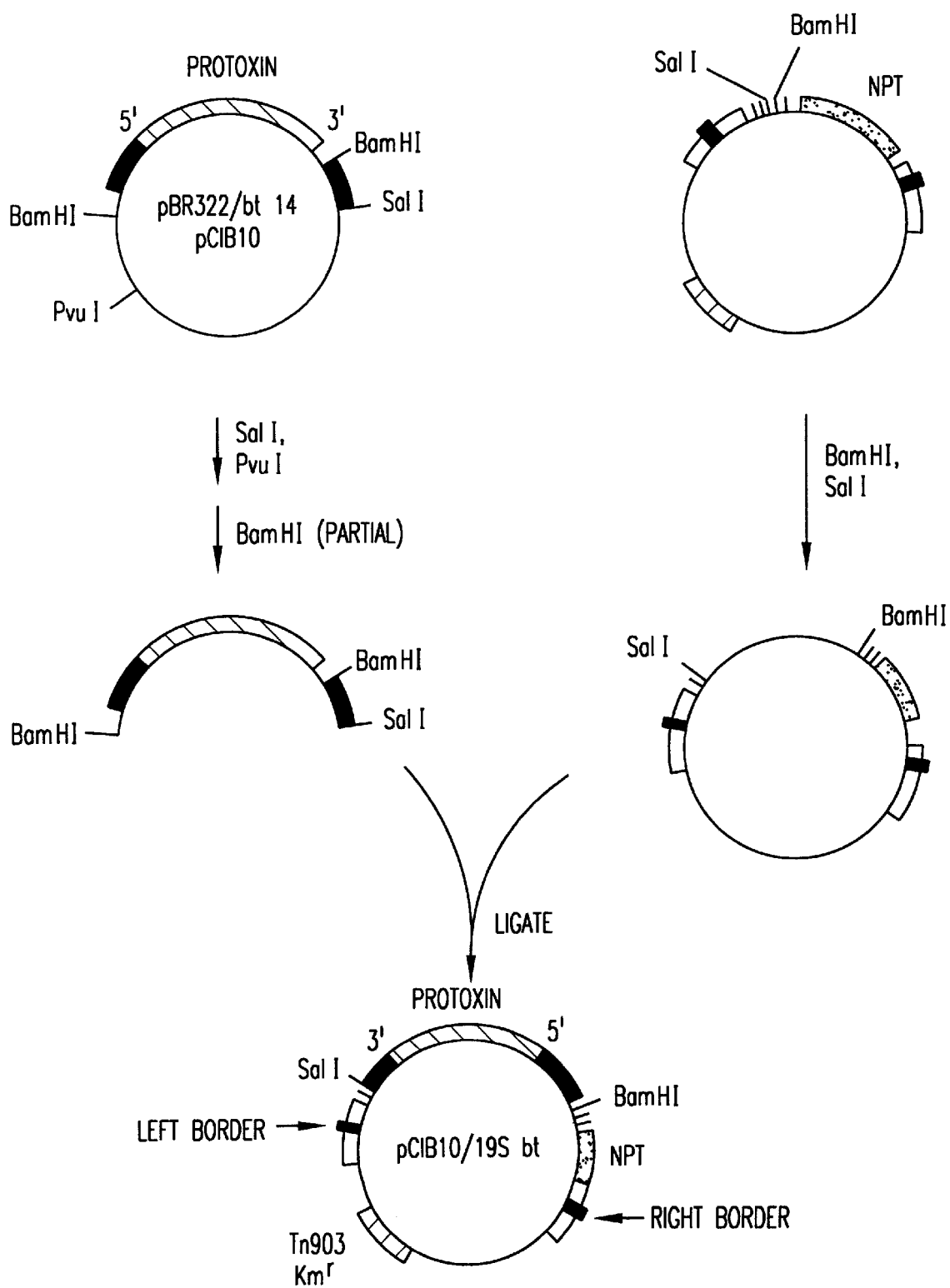
FIG. 11. Construction of pCIB10/19SBt.

The following steps are shown in FIG. 11. Plasmid pBR322/Bt14 DNA is digested with endonucleases PvuI and SalI, and then partially digested with endonuclease BamHI. A BamHI-SalI fragment approximately 4.2 kbp in size, containing the chimeric gene, was isolated following agarose gel electrophoresis, and mixed with plasmid pCIB10 DNA which has been digested with endonucleases BamHI and SalI. After incubation with T4 DNA ligase and transformation into *E. coli* strain HB101, plasmid pCIB10/19SBt is obtained (see FIG. 11). This plasmid contains the chimeric protoxin gene in the plasmid vector pCIB10.

In order to transfer plasmid pCIB10/19SBt from *E. coli* HB101 to Agrobacterium, an intermediate *E. coli* host strain S17-1 is used. This strain, obtainable from Agrigenetics Research Corp., Boulder, Co., contains mobilization functions that can transfer plasmid pCIB10 directly to Agrobacterium via conjugation, thus avoiding the necessity to transform naked plasmid DNA directly into Agrobacterium (reference for strain S17-1 is Simon et al., "Molecular Genetics of the Bacteria-Plant Interaction", A Puhler, ed, Springer Verlag, Berlin, pages 98–106, 1983). First, plasmid pCIB10/19SBt DNA is introduced into calcium chloride-treated S17-1 cells. Next, cultures of transformed S17-1 cells and *Agrobacterium tumefaciens* strain LBA4404 [Ooms et al., Gene, 14, 33–50 (1981)] are mixed and mated on an N agar (Difco) plate overnight at room temperature. A loopful of the resulting bacteria are streaked onto AB minimal media; Watson, B. et al., J. Bacteriol. 123: 255–264 (1975) plated with 50 ug/ml kanamycin and incubated at 28° C. Colonies are restreaked onto the same media, then restreaked onto N agar plates. Slow-growing colonies are picked, restreaked onto AB minimal media with kanamycin and single colonies isolated. This procedure selects for Agrobacteria containing the pCIB10/19SBt plasmid.

EXAMPLE 5

Transfer of the Chimeric Gene to Tobacco Plant Cells

Protoplasts of *Nicotiana tabacum* cv. "Coker 176" are prepared as follows. Four to five week old shoot cultures are grown aseptically in MS medium; Murashige and Skoog, Physiol. Plant., 15, 473–497 (1962) without hormones at 26° C. with a 16 hour light/8 hour dark photoperiod. Approximately 1.5 grams of leaf tissue are removed from the plant and distributed equally among 8–10 Petri dishes (100×25 mm, Lab-Tek), each containing 10 mls. of enzyme solution. Enzyme solution contains 1% cellulase R-10, obtained from Yakult Pharmaceutical Co., 0.25% macerase, from Calbiochem Co., 1% pectolyase Y-23, from Seishin Pharmaceutical Co., 0.45 M mannitol and 0.1×K3 salts; Nagy and Malign, Z. Pflanzenphysiol., 78, 453–455 (1976). Tobacco leaves are cut into thin strips with a scalpel, the dishes are sealed, placed on a gyrotory shaker at 35 rpm and incubated with the enzymes for 4–5 hours at room temperature.

Next, contents of the dishes are filtered through a cheesecloth-lined funnel and collected in a flask. The filtrate is pipetted into Babcock flasks containing 35 mls each of rinse solution. [Rinse solution contains 0.45M sucrose, MES (2-[N-morpholino]ethanesulfonic acid), and 0.1×K3 salts.] The bottles are centrifuged at 80×g for ten minutes, after which the protoplasts will have floated to the top of the bottle. The protoplasts are removed with a 1 ml pipet, combined into one bottle, and rinsed twice more. The resulting protoplasts are suspended in K3 medium in a 15 ml disposable centrifuge tube. Concentration of protoplasts is determined by counting in a Fuchs-Rosenthal hemocytometer. Protoplasts are then plated at a density of 100,000/ml in 6 mls of liquid K3 medium per 100×20 mm Petri dish (Corning). The dishes containing the protoplasts are incubated at 26° C. in the dark for two days, during which time cell wall regeneration will occur.

After two-day incubation, 5 ul of a stationary culture of *A. tumefaciens* containing pCIB10/19SBt are added to the dish of protoplasts. (The agrobacteria are grown in YEP medium plus 50 ug/ml kanamycin at 28° C. until stationary phase is reached.) After incubation for three more days at 26° C., cefotaxime (Calbiochem) is added to 500 ug/ml to kill the Agrobacteria. The following day, cells are diluted with 3 mls fresh K3 medium per dish, and cefotaxime added again to a concentration of 500 ug/ml. Cells are then grown at 26° C. for 2–3 weeks and then screened on selective medium as described by DeBlock et al., EMBO J., 3, 1681–1689 (1984).

EXAMPLE 6

Construction of a *Bacillus thuringiensis* Protoxin Chimeric Gene with the CaMV 35S Promoter Part I. Construction of CaMV 35S Promoter Cassette.

Figure 12:
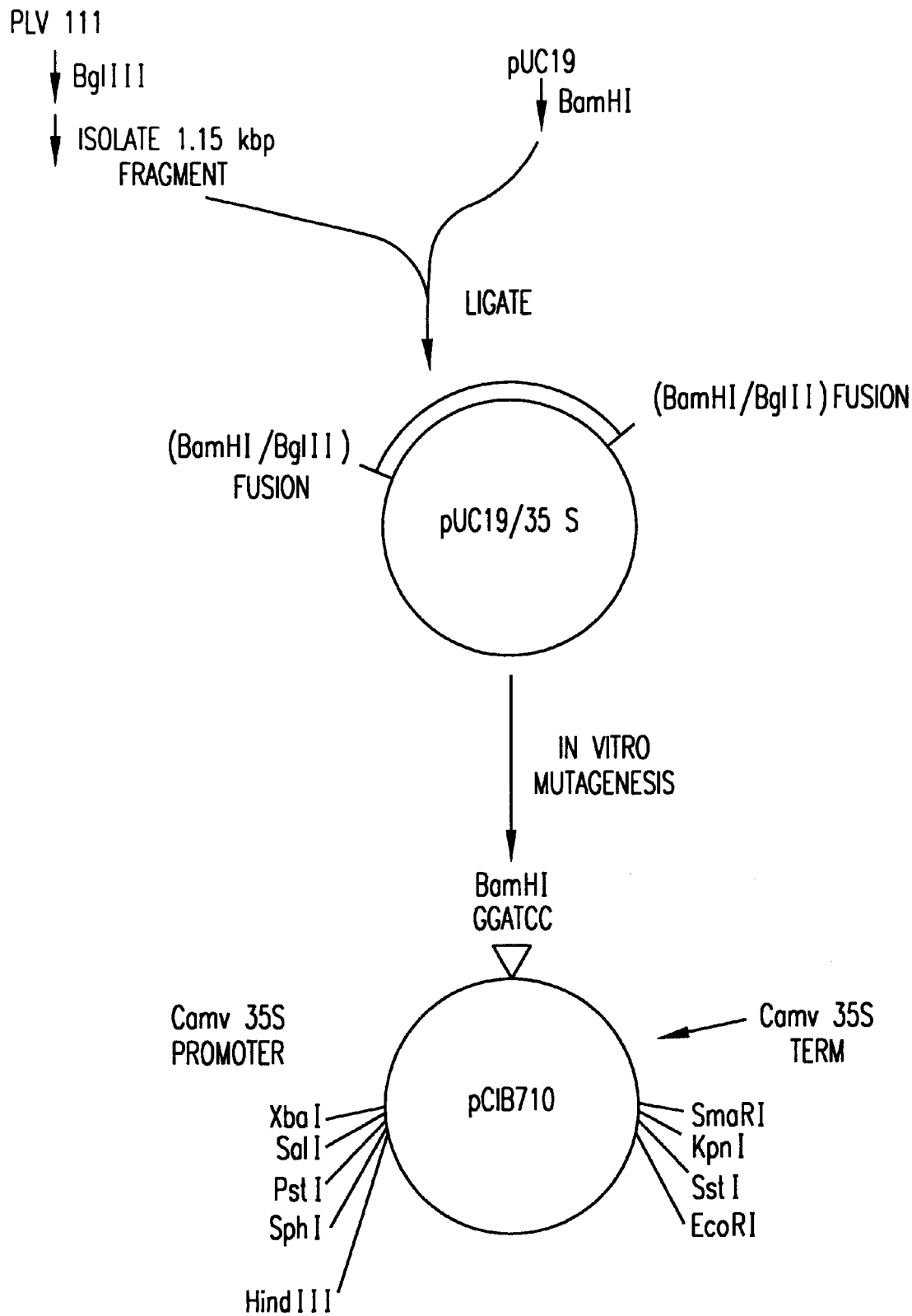
FIG. 12. Construction of pCIB 710.

A CaMV 35S Promoter Cassette Plasmid pCIB710 is constructed as shown in FIG. 12. This plasmid contains CaMV promoter and transcription termination sequences for the 35S RNA transcript [Covey, S. N., Lomonossoff, G. P. and Hull, R., Nucl. Acids Res., 9, 6735–6747 (1981)]. A 1149 bp BglII restriction fragment of CaMV DNA [bp 6494–7643 in Hohn et al., Current Topics in Microbiology and Immunology, 96, 194–220 and Apendices A to G (1982)] is isolated from plasmid pLV111 (obtained from Dr. S. Howell, Univ. of California—San Diego; alternatively, the fragment can be isolated directly from CaMV DNA) by preparative agarose gel electrophoresis as described earlier and mixed with BamHI-cleaved plasmid pUC19 DNA, treated with T4 DNA ligase, and transformed into *E. coli*. (Note the BamHI restriction site in the resulting plasmid has been destroyed by ligation of the BglII cohesive ends to the BamHI cohesive ends.) The resulting plasmid, called pUC19/35S, is then used in oligonucleotide-directed in-vitro mutagenesis to insert the BamHI recognition sequence GGATCC immediately following CaMV nucleotide 7483 in the Hohn reference. The resulting plasmid, pCIB710, contains the CaMV 35S promoter region and transcription termination region separated by a BamHI restriction site. DNA sequences inserted into this BamHI site will be expressed in plants by these CaMV transcription regulation sequences. (Also note that pCIB710 does not contain any ATG translation initiation codons between the start of transcription and the BamHI site.)

Part II. Insertion of the CaMV 35S Promoter/Terminator Cassette into pCIB10.

Figure 13:
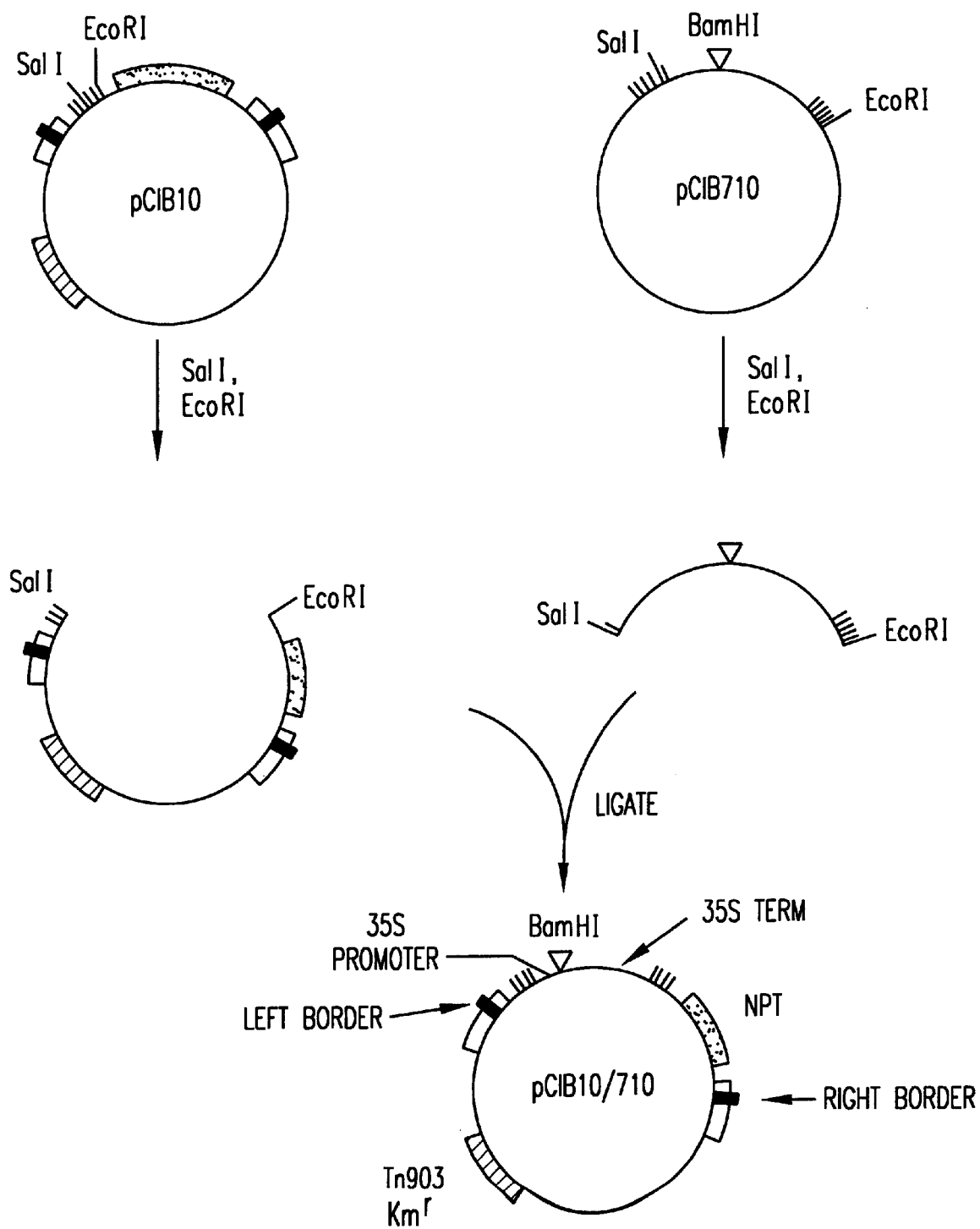
FIG. 13. Construction of pCIB10/710.

The following steps are outlined in FIG. 13. Plasmids pCIB10 and pCIB710 DNAs were digested with EcoRI and SalI, mixed and ligated. The resulting plasmid, pCIB10/710 has the CaMV 35S promoter/terminator cassette inserted into the plant transformation vector pCIB10. The CaMV 35S sequences are between the T-DNA borders in pCIB10, and thus will be inserted into the plant genome in plant transformation experiments.

Part III. Insertion of the *Bacillus thuringiensis* protoxin gene into pCIB10/710.

Figure 14:
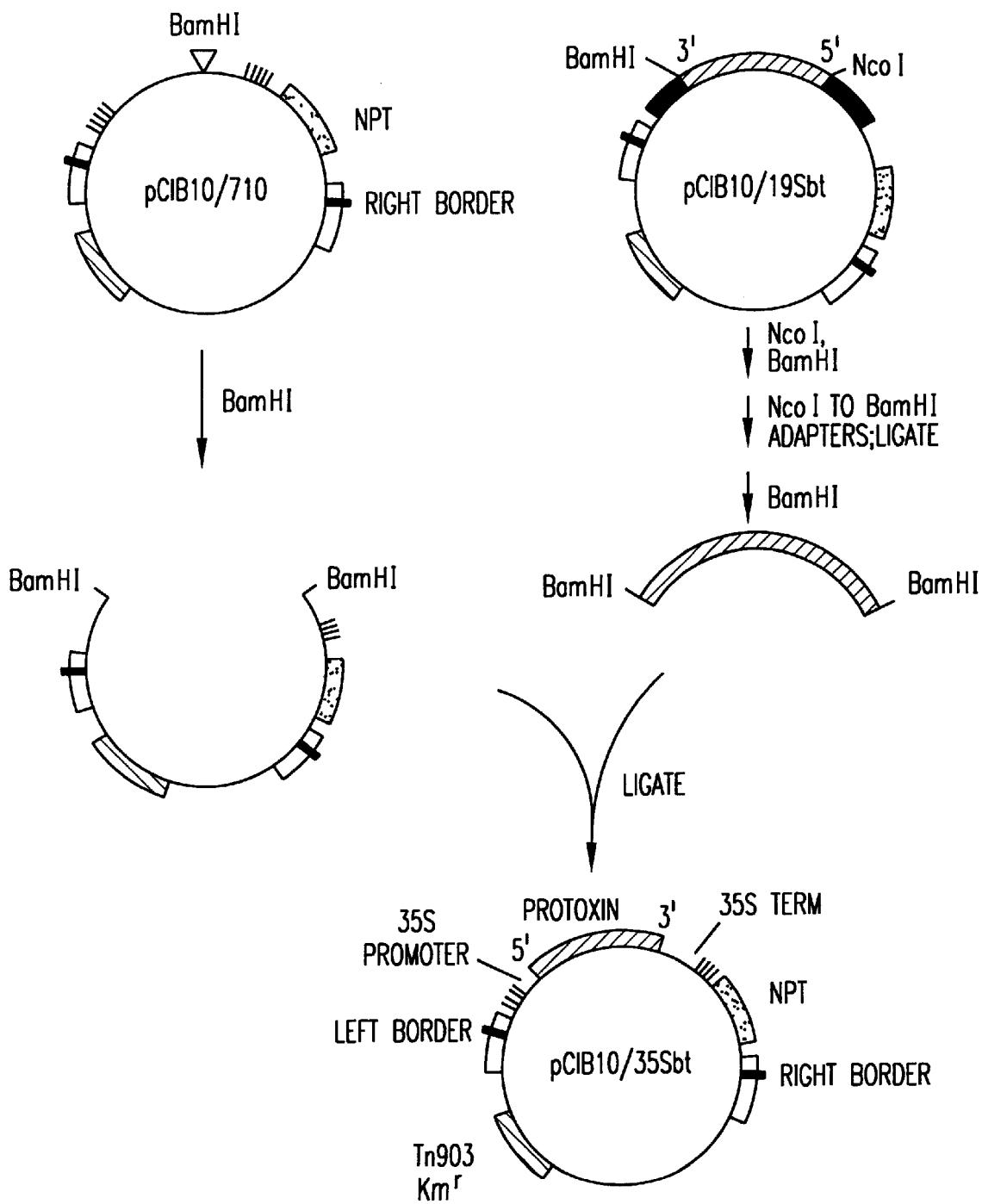
FIG. 14. Construction of pCIB10/35SBt.
Figure 15:
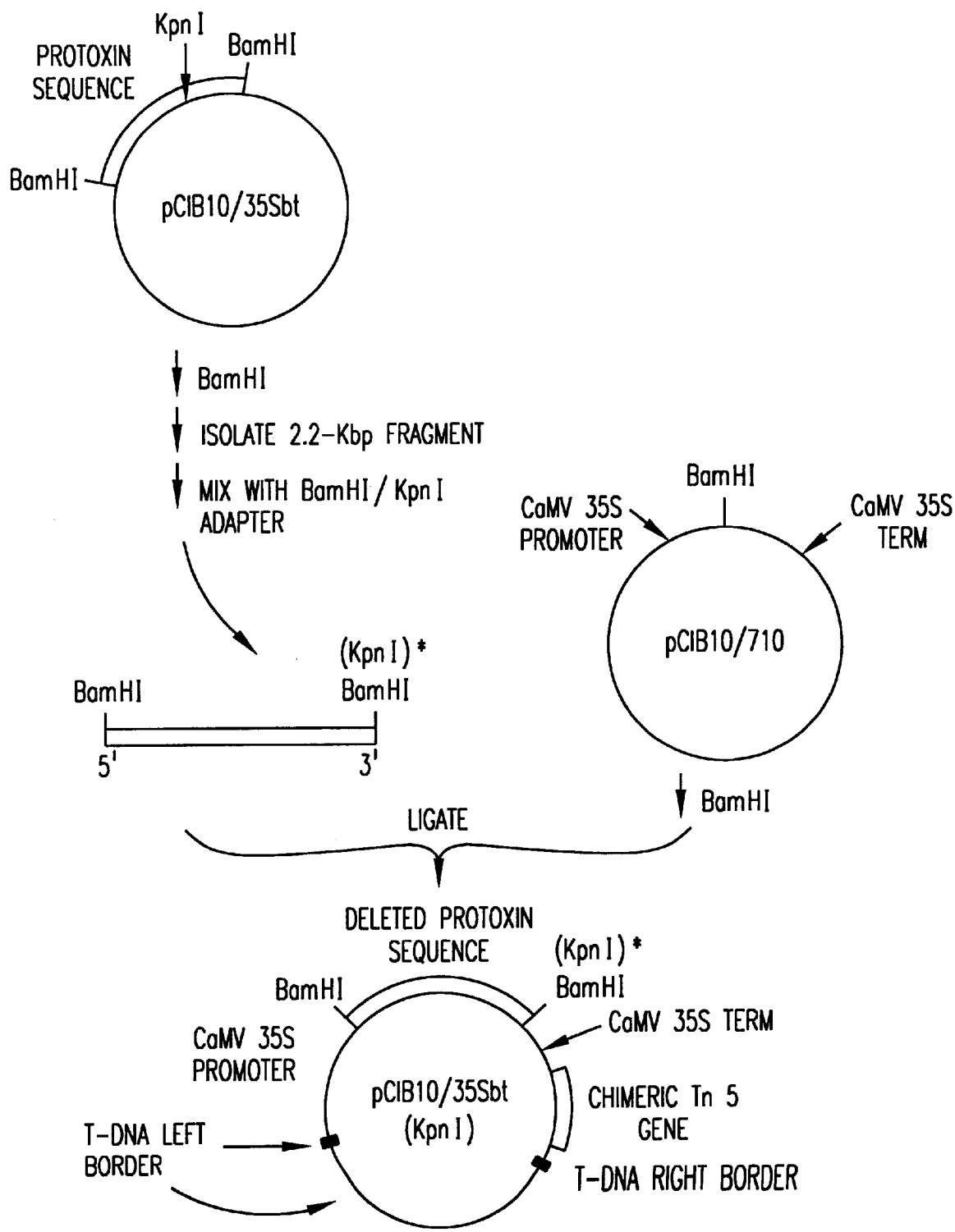
FIG. 15. Construction of pCIB10/35SBt(KpnI).

The following steps are outlined in FIG. 14. As a source of the protoxin gene, plasmid pCIB10/19SBt was digested with BamHI and NcoI, and the 3.6-kb fragment containing the protoxin gene was isolated by preparative gel electrophoresis. The fragment was then mixed with synthetic NcoI-BamHI adaptor with the sequence 5'-CATGGCCGGATCCGGC-3', then digested with BamHI. This step creates BamHI cohesive ends at both ends of the protoxin fragment. This fragment was then inserted into BamHI-cleaved pCIB10/710. The resulting plasmid, pCIB10/35SBt, shown in FIG. 14, contains the protoxin gene between the CaMV 35S promoter and transcription termination sequences.

Part IV. Transfer of the plasmid pCIB10/35SBt into *Agrobacterium tumefaciens* for plant transformation.

The plasmid pCIB10/35SBt was transferred into *A. tumefaciens* strain LpA4404 as described in example 4, above.

EXAMPLE 6a

Construction of pTOX, Containing a Chimeric Gene Encoding the Insecticidal Toxin Gene of *Bacillus thuringiensis* var *tenebrionis*

A gene encoding the insecticidal crystal protein gene of *Bacillus thuringiensis* var. *tenebrionis* has been characterized and sequenced [Sekar, V. et al., Proc. Natl. Acad Sci USA, 84 (1987) 7036–7040]. This coding sequence is isolated on a convenient restriction fragment, such as a HindIII fragment of approximately 3 kb in size, and inserted into an appropriate plant expression vector, such as the plasmid pCIB 770 [Rothstein, S. et al., Gene, 53 (1987) 153–161]. The plasmid pCIB 770 contains a chimeric kanamycin gene for expression in plants, as well as the promoter and terminator of the 35S RNA transcript of CaMV [cauliflower mosaic virus] separated by a unique BamH1 site. The restriction fragment bearing the toxin coding sequence is made compatible to the unique BamHI site of pCIB 770 by use of the appropriate molecular adapter and ligated together.

EXAMPLE 6b

Construction of pSAN, Containing a Chimeric Gene Encoding the Insecticidal Toxin Gene of *Bacillus thuringiensis* Strain San Diego A gene encoding the insecticidal protein of *Bacillus thuringiensis* strain san diego has been characterized and sequenced by Herrnstadt et al., EP-0-202-739 and EP-0-213-818. This coding sequence is isolated on a convenient restriction fragment and inserted into the appropriate plant expression vector, such as pCIB 770. The plasmid pCIB770 contains a chimeric kanamycin gene for expression in plants, as well as the promoter and terminator of the 35S RNA transcript of CaMV [cauliflower mosaic virus] separated by a unique BamH site. The restriction fragment bearing the toxin coding sequence is made compatible to the unique BamHI site of pCIB 770 by use of the appropriate molecular adapter and ligated together.

EXAMPLE 7

Construction of a Deleted *Bacillus thuringiensis* Protoxin Gene Containing Approximately 725 Amino Acids, and Construction of a Chimeric Gene Containing this Deleted Gene with the CaMV 35S Promoter A deleted protoxin gene containing approximately 725 amino acids is made by removing the COOH-terminal portion of the gene by cleaving at the KpnI restriction endonuclease site at position 2325 in the sequence shown in Formula I. Plasmid pCIB10/35SBt (FIG. 14) is digested with BamHI and KpnI, and the approximately 2.2-kbp BamHI/KpnI fragment containing the deleted protoxin gene is isolated by preparative agarose gel electrophoresis. To convert the KpnI site at the 3' end to a BamHI site, the fragment is mixed with a KpnI/BamHI adapter oligonucleotide and ligated. This fragment is then mixed with BamHI-cleaved pCIB10/710 (FIG. 13). The resulting transformants, designed pCIB10/35SBt(KpnI) and shown in FIG. 15, contain the deleted protoxin gene of approximately 725 amino acids. These transformants are selected on kanamycin.

EXAMPLE 8

Construction of a Deleted *Bacillus thuringiensis* Protoxin Gene Containing Approximately 645 Amino Acids, and Construction of a Chimeric Gene Containing this Deleted Gene with the CaMV 35S Promoter A deleted protoxin gene containing approximately 645 amino acids is made by removing the COOH-terminal portion of the gene by cleaving at the BclI restriction endonuclease site at position 2090 in the sequence shown in Formula I. Plasmid pCIB10/35SBt (FIG. 14) is digested with BamHI and BclI, and the approximately 1.9-kbp BamHI/BclI fragment containing the deleted protoxin gene is isolated by preparative agarose gel electrophoresis. Since BclI creates a cohesive end compatible with BamHI, no further manipulation is required prior to ligating this fragment into BamHI-cleaved pCIB10/710 (FIG. 13). The resulting plasmid, which has the structure pCIB10/35SBt (BclI) shown in FIG. 16, is selected on kanamycin.

EXAMPLE 9

Construction of a Deleted *Bacillus thuringiensis* Protoxin Gene Containing Approximately 607 Amino Acids, and Construction of a Chimeric Gene Containing this Deleted Gene with the CaMV 35S Promoter A deleted protoxin gene is made by introducing a BamHI cleavage site (GGATCC) following nucleotide 1976 in the sequence shown in Formula I. This is done by cloning the BamHI fragment containing the protoxin sequence from pCIB10/35SBt into mp18, and using standard oligonucleotide mutagenesis procedures described above. After mutagenesis, double-standard replicative form DNA is prepared from the M13 clone, which is then digested with BamHI. The approximately 1.9-kbp fragment containing the deleted protoxin gene is inserted into BamHI-cleaved pCIB10/710. The resulting plasmid, which the structure pCIB10/35SBt(607) shown in FIG. 17, is selected for on kanamycin.

Some of the following Examples describe specific protocols for transforming cotton cells and regenerating cotton plants from cotton cells and callus. It should be understood that those with ordinary skill in the art may vary the details of the protocols while still remaining within the limits of the present invention. For example, numerous plant tissue culture media are know, some of which are described in detail below. The ordinarily skilled tissue culture scientist would know how to vary these solutions in order to achieve the same or similar results. Thus, Example 11 discloses a modified White's stock solution as a seed germination and callus development media; Example 12 describes a Murashige and Skoog stock solution as a callus growth/maintenance media; Example 14 describes a Beasley and Ting stock solution as a plant germination medium. The ordinarily skilled tissue culture scientist knows how to vary these solutions in order to achieve results similar to those described in the Examples. Thus, the sugar in the callus growth medium may be glucose, which minimizes phenolic secretions, or sucrose, which promotes the formation of embryogenic callus.

The explants used in the transformation procedure may be from any suitable source, such as from seedlings, especially a hypocotyl or cotyledon, or from immature embryos of developing fruit.

Any antibiotic toxic to Agrobacterium may be used to kill residual Agrobacterium after the transformation step. Cefotaxime is preferred.

10. Regeneration of Cotton Plants (from Finer, Ciba-Geigy U.S. Application, Filed on the Same Day as the Present Application)

a) Media

All media in this example contain Murashige and Skoog inorganic salts and Gamborg's B-5 vitamins, are adjusted to pH 5.7, and have the following composition (mg/l):

| Macronutrients | |
|---|---|
| $MgSO_4.7H_2O$ | 370 |
| $KH_2PO_4$ | 170 |
| $KNO_3$ | 1900 |
| $NH_4NO_3$ | 1650 |
| $CaCl_2.2H_2O$ | 440 |

| Micronutrients | |
|---|---|
| $H_3BO_3$ | 6.2 |
| $MnSO_4.H_2O$ | 15.6 |
| $ZnSO_4.7H_2O$ | 8.6 |
| $NaMoO_4.2H_2O$ | 0.25 |
| $CuSo_4.5H_2O$ | 0.025 |
| $CaCl_2.6H_2O$ | 0.025 |
| KI | 0.83 |

-continued

| Micronutrients | |
|---|---|
| FeSO$_4$.7H$_2$O | 27.8 |
| Na$_2$EDTA | 37.3 |

| Vitamins | |
|---|---|
| Thiamine.HCl | 10 |
| Pyridoxine.HCl | 1 |
| Nicotinic acid | 1 |
| Myo-Inositol | 100 |

In addition, the various media have the following components.
Medium# Additional Components

| | |
|---|---|
| 1 | 20 g/l sucrose, 0.6% noble agar (Difco) |
| 2 | 30 g/l glucose, 2 mg/l alpha-naphthaleneacetic acid 1 mg/l kinetin, 0.8% noble agar |
| 3 | 30 g/l sucrose, 2 mg/l alpha-naphthaleneacctic acid 1 mg/1 kinetin, 0.8% noble agar |
| 4 | 20 g/l sucrose, 0.5 mg/l picloram |
| 5 | 20 g/l sucrose, 5 mg/l 2,4-dichlorophenoxyacetic acid |
| 6 | 20 g/l sucrose, 15 mM glutamine |

Media at 25° C., 28° C. and 31° C. refer, in addition to the temperature, to a photoperiod of 16 hours light: 8 hours dark at a light intensity of 20 microEm$^{-2}$s$^{-2}$.

b) Seed Sterilization and Planting

Seeds of cotton (*Gossypium hirsutum* var. Coker 310) are delinted by placing seed in concentrated H$_2$SO$_4$ for 2 min. Seeds are then washed 4 times with sterile, distilled water, dipped in 95% ethanol, flamed and planted on Medium #1 at 31° C.

c) Callus Induction

Seven days following planting, seedling hypocotyls are excised, sliced longitudinally, cut into 2 mm sections and placed on Medium #2 at 31° C. Hypocotyl sections (2 mm) are transferred weekly to fresh Medium #2 and these cultures are also maintained at 31° C. Following 4 weekly transfers to Medium #2, callus tissue proliferating on the hypocotyl sections is removed from the original explant and placed on Medium #3 at 31° C. The callus is transferred to fresh Medium #3 after one month and maintained for an additional 1 to 2 months.

d) Suspension Culture Initiation

For initiation of suspension cultures, 100 mg of callus tissue is placed into 35 ml of Medium #4 in a 125 ml DeLong flask. Suspensions are rotated for 6 weeks at 140 rpm, and 28° C., at which time they begin rapidly to proliferate.

e) Embryo Development and Plant Regeneration

The embryos that form in Medium #4 proliferate even faster following replacement of Medium #4 by Medium #5. This embryogenic suspension is divided and subcultured every 3–7 days into fresh Medium #5. For development of embryos proliferating in Medium #5, the embryos are washed with, and then placed into, Medium #6. Three to four weeks following transfer to Medium #6, the mature embryos are placed on a solid medium at 25° C. The solid medium consists of a modified MS medium containing MS salts with 40 mM KNO$_3$ in place of KNO$_3$ and NH$_4$NO$_3$, B-5 vitamins, 2% sucrose, 15 mM glutamine, and solidified with 0.2% Gelrite (pH 5.7). Embryos are placed in petri dishes at 25° C. Shoot development is sporadic on this medium and root elongation is enhanced with the transfer of the embryos to the above modified MS medium without glutamine. Germinating embryos are then planted in vermiculite in 4" pots and covered with a beaker (25° C.). After plantlets are established in vermiculite, the beaker is removed. Following one week at 28° C., the plantlets are placed in the greenhouse for further development into plants.

Figure 18:
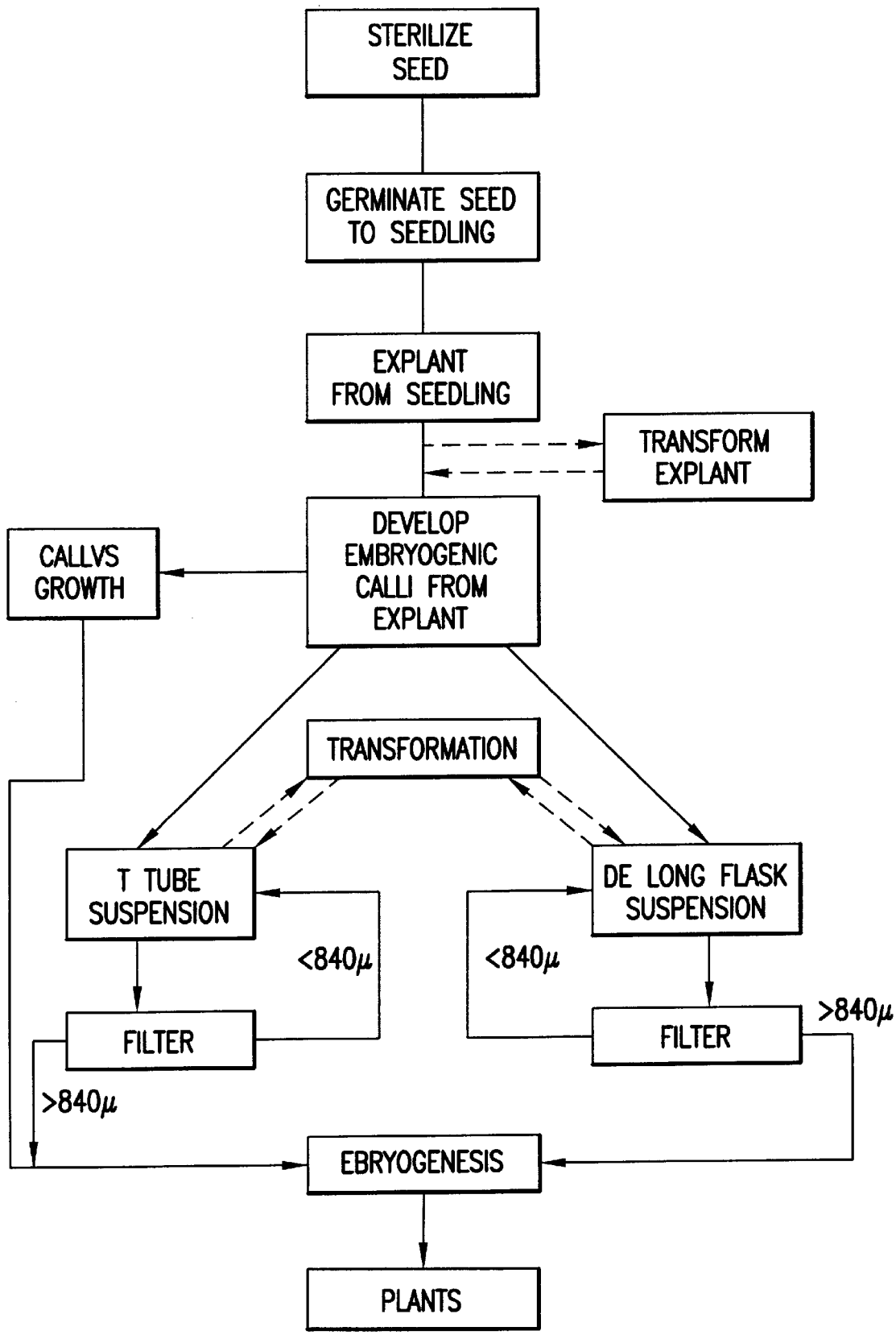
FIG. 18. Summary of procedure for the regeneration and transformation of cotton plants.

11–28. Regeneration of Cotton Plants (Substantially from Phytogen U.S. Application 07/122,162, Filed on Same Day as Present Application; See FIG. 18)

EXAMPLE 11

SEED GERMINATION AND CALLUS DEVELOPMENT MEDIA
COMPOSITION OF MODIFIED WHITE'S STOCK SOLUTION
(Phytomorphology 11:109–127, 1961)
(incorporated herein by reference)

| Component | Concentration per 1000 ml. | Comments |
|---|---|---|
| MgSO$_4$.7 H$_2$O | 3.6 g | Dissolve and make up |
| Na$_2$SO$_4$ | 2.0 g | the final volume to |
| NaH$_2$PO$_4$.H$_2$O | 1.65 g | 1000 ml. Label White's AStock. Use 100 ml/l of final medium. |
| Ca(NO$_3$)$_2$.4 H$_2$O | 2.6 g | Dissolve and make up |
| KNO$_3$ | 800 mg | the final volume to |
| KCl | 650 mg | 1000 ml. Label White's BStock. Use 100 ml/l of final medium. |
| Na$_2$MoO$_4$.2H$_2$O | 2.5 mg | Dissolve and make up |
| CoCl$_2$.6H$_2$O | 2.5 mg | the final volume to 100 |
| MnSO$_4$.H$_2$O | 300 mg | ml. Label White'sC |
| ZnSO$_4$.7 H$_2$O | 50 mg | Stock. Use 1.0 ml/l of |
| CuSO$_4$.5 H$_2$O | 2.5 mg | final medium. |
| H$_3$BO$_3$ | 50 mg | |
| Fe-EDTA | | Use 10 ml/l of MSFe EDTA. (See below) |
| Organic | | Use 10 ml/l of MS organic. (See below) |

EXAMPLE 12

CALLUS GROWTH/MAINTENANCE MEDIA
COMPOSITION OF MURASHIGE & SKOOG
(MS) STOCK SOLUTIONS
(Physiol. Plant 15:473–497, 1962)
(incorporated herein by reference)

| Component | Concentration per 1000 ml. of Stock | Comments |
|---|---|---|
| NH$_4$NO$_3$ | 41.26 g | Dissolve and make up |
| KNO$_3$ | 47.50 g | the final volume to |
| CaCl$_2$.2 H$_2$O | 11.00 g | 1000 ml. Label MS-Major |
| MgSO$_4$.7 H$_2$O | 9.25 g | Use 40 ml/l of final |
| KH$_2$PO$_4$ | 4.25 g | medium. |
| KI | 83 mg | Dissolve and make up |
| H$_3$BO$_3$ | 620 g | the final volume to |
| MnSO$_4$.H$_2$O | 1690 mg | 1000 ml. Label MS-Minor. Use 100 ml/l |
| ZnSO$_4$.7 H$_2$O | 860 mg | of final medium. |
| Na$_2$MoO$_4$.2 H$_2$O | 125 g | |
| CuSO$_4$.5 H$_2$O | 2.5 mg | |
| CoCl$_2$.6 H$_2$O | 2.5 mg | |
| Nicotinic acid | 50 mg | Dissolve and make up |

-continued

CALLUS GROWTH/MAINTENANCE MEDIA
COMPOSITION OF MURASHIGE & SKOOG
(MS) STOCK SOLUTIONS
(Physiol. Plant 15:473–497, 1962)
(incorporated herein by reference)

| Component | Concentration per 1000 ml. of Stock | Comments |
|---|---|---|
| Pyridoxin HCl | 50 mg | the final volume to 1000 ml. Label MS-Organic. Freeze in 10 ml aliquots. Use 10 ml/l of final medium. |
| Thiamine HCl | 10 mg | |
| Fe SO$_4$.7H$_2$O | 2.78 g | Dissolve 2.78 g of FeSO$_4$.7 H$_2$O in about 200 ml of deionized water. Dissolve 3.73 g of Na$_2$-EDTA.2 H$_2$O (disodium salt of ethlenediamino-tetraacetic acid dihydrate) in 200 ml of deionized water in another beaker. Heat the Na$_2$-EDTA solution on a hot plate for about 10 minutes. While constantly stirring, add FeSO$_4$ solution to Na$_2$-EDTA solution. Cool the solution to room temperature and make up the volume to 1000 ml. Label MSFe-EDTA. Cover bottle with foil and store in refrigerator. Use 10 ml/l of final medium. |
| Ne$_2$ EDTA.2 H$_2$O | 3.73 g | |
| Thiamine HCl | 50 mg | Dissolve and make up the volume to 500 ml. Label MS-Thiamine. Use 4.0 ml/l of final medium. |
| m-Inositol | 10 g | Dissolve and make up the final volume to 1000 ml. Label MS-glycine/inositol. Use 10 ml/l of final medium. |
| Glycine | 0.2 g | |

EXAMPLE 14

PLANT GERMINATION MEDIA
COMPOSITION OF BEASLEY AND TING'S STOCK SOLUTIONS
(Am. J. Bot. 60:130–139, 1973)

| Component | Concentration per 1000 ml. | Comments |
|---|---|---|
| KH$_2$PO$_4$ | 2.72 g | Dissolve and make up the volume to 100 ml. Label B&T-AStock. Use 10 ml/l final medium. |
| H$_3$BO$_3$ | 61.83 mg | |
| Na$_2$MoO$_4$.2 H$_2$O | 2.42 mg | |
| CaCl$_2$.2 H$_2$O | 2.6 g | Dissolve and make up the volume to 100 ml. Label B&T-BStock. Use 10 ml/l of final medium. |
| KI | 8.3 mg | |
| CoCl$_2$.6 H$_2$O | 0.24 mg | |
| MgSO$_4$.7 H$_2$O | 4.93 g | Dissolve and make up the volume to 100 ml. Label B&T - C Stock. Use 10 ml/l of final medium. |
| MnSO$_4$.H$_2$O | 169.02 mg | |
| ZnSO$_4$.7 H$_2$O | 86.27 mg | |
| CuSO$_4$.5 H$_2$O | 0.25 mg | |
| KNO$_3$ | 25.275 g | Dissolve and make up the volume to 200 ml. Label |

-continued

PLANT GERMINATION MEDIA
COMPOSITION OF BEASLEY AND TING'S STOCK SOLUTIONS
(Am. J. Bot. 60:130–139, 1973)

| Component | Concentration per 1000 ml. | Comments |
|---|---|---|
| | | BT-DStock. Use 40 ml/l of final medium. |
| Nicotinic acid | 4.92 mg | Dissolve and make up the final volume to 100 ml. Label B&T-Organics. Use 10 ml/l of final medium. |
| Pyridoxine HCl | 8.22 mg | |
| Thiamine HCl | 13.49 mg | |
| Fe-EDTA | | Use 10 ml/l of MS-Fe-EDTA. |
| Inositol | | 100 mg/l of final medium. |
| NH$_4$NO$_3$ (15 uM) | | 1200.6 mg/l of final medium. |

EXAMPLE 15

Regeneration of Plants Starting from Cotyledon Explants

Seeds of Acala cotton variety SJ2 of *Gossypium hirsutum* are sterilized by contact with 245% alcohol for three minutes, then twice rinsed with sterile water and immersed with a 15% solution of sodium hypochlorite for 15 minutes, then rinsed in sterile water. Sterilized seeds are germinated on a basal agar medium in the darkfor approximately 14 days to produce a seedling. The cotyledons of the seedlings are cut into segments of which are transferred aseptically to a callus inducing medium [see above] consisting of Murashige and Skoog (MS) major and minor salts supplemented with 0.4 mg/l thiamine-HCl, 30 g/l glucose, 2.0 mg/l alpha-naphthaleneacetic acid (NAA), 1 mg/l kinetin, 100 mg/l of m-inositol, and agar (0.8%). The cultures are incubated at about 30° C. under conditions of 16 hours light and 22 hours darkness in a Percivall incubator with fluorescent lights (cool daylight) providing a light intensity of about 2000–4000 lux. Calli are formed on the cultured tissue segments within 3 to 4 weeks and are white to gray-greenish in color. The calli formed are subcultured every three to four weeks onto a callus growth medium comprising MS medium containing 100 mg/l m-inositol, 2.0 g/l sucrose, 2 mg/l alpha-naphthalenacetic acid (NAA) and agar. Somatic embryos formed four to six months after first placing tissue explants callus inducing medium. The callus and embryos are maintained on callus growth medium by subculturing onto fresh callus growth medium every three to four weeks.

Somatic embryos which formed on tissue pieces are explanted either to fresh callus growth medium, or to Beasley & Ting's medium (embryo germination medium). The somatic plantlets which are formed from somatic embryos are transferred onto Beasley and Ting's medium which contained 15 mg/l ammonium nitrate and 15 mg/l casein hydrolysate as an organic nitrogen source. The medium is solidified by a solidifying agent (Gelrite) and plantlets are placed in Magenta boxes. The somatic embryos developed into plantlets within about three months. The plantlets are rooted at the six to eight leaf stage [about three to four inches tall], and are transferred to soil and maintained in an incubator under high humidity for three to four weeks, after which they are transferred to the greenhouse. After hardening, plants are transferred to open tilled soil.

EXAMPLE 16

Regeneration of Plants Starting from Cotyledon Explants—Variation 1

The procedure of Example 15 is repeated using instead half-strength MS medium in which all medium components have been reduced to one-half the specified concentration. Essentially the same results are obtained.

EXAMPLE 17

Regeneration of Different Cotton Varieties from Cotyledon Explants

The procedure of Examples 15 and 16 is repeated with Acala cotton varieties SJ4, SJ5, SJ2C-1, GC510, B1644, B2724, B1810, the picker variety Siokra and the stripper variety FC2017. All are successfully regenerated.

EXAMPLE 18

Regeneration of Cotton Plants from Cotyledon Explants with Suspension Cell Culture as Intermediate Step The procedure of Example 15 is repeated to the extent of obtaining callus capable of forming somatic embryos. Pieces of about 750–1000 mg of actively growing embryogenic callus is suspended in 22 ml units of liquid suspension culture medium comprised of MS major and minor salts, supplemented with 0.4 mg/l thiamine HCl, 20 g/l sucrose, 100 mg/l of inositol and alpha-naphthaleneacetic acid (2 mg/l) in T-tubes and placed on a roller drum rotating at 1.5 Å rpm under 16:8 light:dark regime. Light intensity of about 2000–4500 lux is again provided by fluorescent lights (cool daylight). After four weeks, the suspension is filtered through an 840 micron size nylon mesh to remove larger cell clumps. The fraction smaller than 840 microns are allowed to settle, ished once with about 20–25 ml of fresh suspension culture medium. This cell suspension is transferred to T-tubes (2 ml per tube) and each tube diluted with 15 ml of fresh suspension culture medium. The cultures are maintained by repeating the above at 10–12 day intervals. At each subculture, the suspension is filtered and only the fraction containing cell aggregates smaller than 840 microns is transferred to fresh suspension culture medium. In all instances, the fraction containing cell clumps larger than 840 microns is placed on to the callus growth medium to obtain mature somatic embryos. The somatic embryos that are formed on callus growth medium are removed and transferred to embryo germination medium. Using the protocol of Example 6, these are germinated, developed into plantlets and then field grown plants.

EXAMPLE 19

Regeneration of Cotton Plants from Cotyledon Explants with Suspension Cell Culture as an Intermediate Step—Variant 1

The procedure of Example 18 is repeated except that suspension cultures are formed by transferring 750–1000 mg of embryogenic calli to a DeLong flask containing 15–20 ml of the MS liquid medium containing 2 mg/l NAA. The culture containing flask is placed on gyrotory shaker and shaken at 100–110 strokes/minute. After three weeks the suspension is filtered through an 840 micron nylon mesh to remove the large cell clumps for plant growth, as in Example 18. The less than 840 micron suspension is allowed to settle, washed once in the MS liquid medium and resuspended in 2 to 5 ml of the MS liquid medium. The suspension is subcultured by transfer to fresh medium in a DeLong flask containing 1–2 ml of suspension and 15 ml of fresh MS liquid medium. The cultures are maintained by repeating this procedure at seven to ten day intervals. At each subculture only the less than 840 micron suspension is subcultured and the large clumps (840 microns or greater) are used for plant growth.

EXAMPLE 20

Production of Plants from Large Clumps of Suspension Cultured Cells [example 19]

After three or four subcultures using the suspension growth procedure of Examples 18 and 19, 1.5 to 2.0 ml of cell suspension from the T-tube and DeLong flask are in each instance plated onto agar-solidified MS medium containing 2 mg/l NAA and Beasley & Ting medium containing 500 mg/l casein hydrolysate. Within three to four weeks embryogenic calli with developing embryos became visible. Again, the 840 micron or greater cell clumps are plated on the callus growth medium giving rise to embryogenic clumps with developing embryos which ultimately grew into plants.

EXAMPLE 21

Transformation of Cotton Suspension Culture Cells to Tumorous-Phenotype by Agrobacteria LBA 4434 a/ Growth of the plant suspension culture. An Acala cotton suspension culture is subcultured into "T" tubes with the medium (MS medium containing 2 g/liter NAA) being changed every seven to ten days. After a medium change, the "T" tube is rotated 240° and the cells allowed to settle out. The supernatant is removed by pipeting prior to transformation and the resulting cells treated as described below.

b/ Description of Agrobacterium vector. The Agrobacterium strain LBA 4434 (Hoekema, A. et al. *Nature* 303: 179–180, 1983) contains a Ti plasmid-derived binary plant transformation system. In such binary systems, one plasmid contains the T-DNA of a Ti-plasmid, the second plasmid contains the vir-region of a Ti-plasmid, and together the two plasmids function to effect plant [transformation. In the strain LBA 4434, the T-DNA plasmid pAL 1050 contains $T_L$ of pTiAch5, an octopine Ti-plasmid. The vir plasmid in strain LBA 4434, pAL 4404, contains the intact virulence regions of pTiAch 5 (Ooms, G. et al. *Plasmid* 21: 15–29, 1982). Strain LBA 4434 is available from Dr. Robert Schilperoort of the Department of Biochemistry, University of Leiden, The Netherlands.

c/ Growth of Agrobacteria. The transforming Agrobacterium strain is taken from a glycerol stock, inoculated in a small overnight culture, from which a 50-ml culture is inoculated the following day. Agrobacteria are grown on YEB medium [YEB is per liter in water: 5 g beef extract, 1 g yeast extract, 5 g peptone, 5 g sucrose, adjusted to pH 21.2 with NaOH. After autoclaving, 1 ml of 2 M $MgCl_2$ is added] to which antibiotics as appropriate have been added. The absorbance at 600 nm of the 50 ml overnight culture is read, the culture is centrifuged and the pellet resuspended in the plant cell growth medium (MS medium plus NAA at 2 mg/ml) to a final absorbance at 600 nm of 0.5. Eight ml of this bacterial suspension is added to each "T" tube containing the plant cells from part a above.

d/ Infection. The "T"tube containing the plant and bacteria cells is agitated to resuspend all cells and returned to a roller drum for three hours to allow the Agrobacteria to attach to the plant cells. The cells are then allowed to settle and the residual supernatant removed. A fresh aliquot of growth medium is added to the "T" tube and this allowed to incubate on a roller drum for a period of 18 to 20 hours in the presence of any residual Agrobacteria which remained.

After this time, the cells are again allowed to settle, the supernatant is removed and the cells are ished twice with a solution of growth medium containing cefotaxime (200 ug/ml). After ishing, the cells from each T-tube are resuspended in 10 ml growth medium containing cefotaxime (200 ug/ml in all cases) and 1 ml aliquots of this plated on petri dishes.

e/ Growth of Transformed Tissue. The cells infected with Agrobacteria grew on the growth medium which had no added phytohormones, indicating the tissue had received the wild-type phytohormone genes in T-DNA. These cells developed into tumors, further indicating transformation of the cultures.

EXAMPLE 22

Cotton Suspension Culture Cells to a Kanamycin-Resistant Non-Tumorous Phenotype

The same procedure as in Example 21 is followed except that different transforming Agrobacteria is used and that the plant selection medium contained an antibiotic for the selection of transformed plant tissue.

a/ Growth of Plant Tissue. As in Example 21, part a.

b/ Description of Agrobacterium. The transforming Agrobacteria contained the T-DNA containing binary vector pCIB 10 (Rothstein, S. J. etal. *Gene* 53: 153–161, 1987) as well as the pAL 4404 vir plasmid. The T-DNA of pCIB 10 contains a chimeric gene composed of the promoter from nopaline synthase, the coding region from Tn5 [encoding the enzyme neomycin phosphotransferase], and the terminator from nopaline synthase.

c/ Growth of Agrobacteria. Agrobacteria containing pCIB 10 are grown on YEB containing kanamycin (50 ug/ml). Otherwise, conditions are as in Example 21, part c.

d/ Infection. Transformation is accomplished as detailed in Example 21 with the change that the 1 ml aliquots resulting in part c are plated immediately on medium containing selective antibiotics. Selection medium contained either kanamycin (50 ug/ml) or G418 (25 ug/ml). Expression of the nos/neo/nos chimeric gene in transformed plant tissue allows the selection of this tissue on either of these antibiotics.

e/ Growth of Transformed Tissue. Plant growth media in this and all following examples contained phytohormones as indicated in Example 1.

In 2–4 weeks, transformed tissue became apparent on the selection plates. Uninfected tissue or control tissue showed no signs of growth, turned brown and died. Transformed tissue grew very well in the presence of kanamycin or G418. At this time, tissue pieces which are growing well are subcultured to fresh selection medium. f/ Growth of Somatic Embryos. Somatic embryos formed on these tissue pieces. Somatic embryos are explanted to fresh medium (non selective).

g/ Germination. When the embryos had begun to differentiate and germinate, ie at the point where they are beginning to form roots and had two or three leaves, they are transferred to Magenta boxes containing growth medium. Growth is allowed to proceed until the plantlet had 15 to 22 leaves, at which time it is removed from the agar medium.

h/ Growth of Plantlet. The plantlet is now placed in potting soil, covered with a beaker to maintain humidity and placed in a Percival incubator for 4–22 weeks. At this time, the beaker is removed and the plant is transferred to the greenhouse.

i/ Growth of Plant in Greenhouse. The plants grew in the greenhouse, floared and set seed.

NO EXAMPLE 23 INCLUDED

EXAMPLE 24

Transformation of Cotton Suspension Culture Cells to a Hygromycin-Resistant Non-Tumorous Phenotype The same procedure as in Example 22 is followed except where noted. Different transforming Agrobacteria are used and the plant selection medium contained an antibiotic appropriate for the selection of transformed plant tissue.

b/ Description of Agrobacterium. The transforming Agrobacteria contained the T-DNA containing binary vector pCIB 2115 (Rothstein, S. J. etal. *Gene* 53: 153–161, 1987) as well as the vir plasmid. The T-DNA of pCIB 2115 contains a chimeric gene composed of the promoter and terminator from the cauliflower mosaic virus (CaMV) 35S transcript [Odell et al, Nature 313: 2210–812, 1985] and the coding sequence for hygromycin B phosphotransferase [Gritz, L. and J. Davies, Gene 25: 179–188].

c/ Growth of Agrobacteria. Agrobacteria containing pCIB 2115 are grown on YEB containing kanamycin (50 ug/ml).

d/ Infection. Transformation is accomplished as detailed in Example 21 with the change that the 1 ml aliquots resulting in part c are plated immediately on medium containing selective antibiotics. Selection medium contained 50 ug/ml hygromycin. Expression of the chimeric hygromycin gene in transformed plant tissue allows the selection of this tissue on medium containing hygromycin.

e/ Growth of Transformed Tissue. As in Example 22, part e except that the antibiotic hygromycin is used in the plant selection growth medium.

EXAMPLE 25

Plant Extraction Procedure

Plant tissue is homogenized in Extraction Buffer [ca 100 mg in 0.1 ml Extraction Buffer].

| Leaf Extraction Buffer |
| --- |
| 50 mM Na$_2$CO$_3$ pH 9.5 |
| 10 mM EDTA |
| 0.05% Triton X-100 |
| 0.05% Tween |
| 100 mM NaCl |
| 1 mM PMSF [Phenylmethylsulfonyl Fluoride] (add just prior to use) |
| 1 mM leupeptine (add just prior to use). |

After extraction, 2 M Tris pH 7.0 is added to adjust the pH of the extract to a pH of 8.0–8.5. The extract is then centrifuged 10 minutes in a Beckman microfuge and the supernatant used for ELISA analysis.

EXAMPLE 26

ELISA Analysis of Plant Tissue

ELISA [enzyme-linked immunosorbent assay] are very sensitive, specific assays for antigenic material. ELISA assays are very useful for studying the expression of polypeptide gene products. The development of ELISA techniques as a general tool is described by M. F. Clark et al in *Methods in Enzymology* 118:742–766 (1986); this is herein incorporated by reference.

An ELISA for the Bt toxin was developed using standard procedures and used to analyze transgenic plant material for expression of Bt sequences. The steps used in this procedure are as given below:

1. ELISA plate is pretreated with ethanol.

2. Affinity-purified rabbit anti-Bt antiserum (50 ul) at a concentration of 3 ug/ml in borate-buffered saline [see below] is added to the plate and this allowed to incubate overnight at 4 degrees C. Antiserum was produced in response to immunizing rabbits with gradient-purified Bt crystals [Ang, B. J. & Nickerson, K. W.; Appl. Environ. Microbiol. 36: 625–626 (1978)] solubilized with sodium dodecyl sulfate.

3. Wash with ELISA Wash Buffer [see below].

4. Treat 1 hour at room temperature with Blocking Buffer [see below].

5. Wash with ELISA Wash Buffer [see below].

6. Add plant extract in an amount to give 50 ug of protein (this is typically ca. 5 microliters of extract). Leaf extraction buffer is described below; protein is determined by the Bradford method [Bradford, M., Anal. Biochem. 72: 248 (1976)] using a commercially available kit [Bio-Rad, Richmond, Calif.]. If dilution of the leaf extract is necessary, ELISA Diluent [see below] is used. Allow this is incubate overnight at 4degrees C.

7. Wash with ELISA Wash Buffer [see below].

8. Add 50 ul affinity-purified goat anti-Bt antiserum at a concentration of 3 ug/ml protein in ELISA Diluent [see below]. Allow this to incubate for one hour at 37 degrees C.

9. Wash with ELISA Wash Buffer [see below].

10. Add 50 ul rabbit anti-goat antibody bound to alkaline phosphatase [commercially available from Sigma Chemicals, St. Louis, Mo.]. This is diluted 1:500 in Diluent. Allow to incubate for one hour at 37 degrees C.

11. Wash with ELISA Wash Buffer [see below].

12. Add 50 microliters substrate [0.6 mg/ml p-nitrophenyl phosphate in ELISA Substrate Buffer (see below)]. Incubate for 30 minutes at room temperature.

13. Terminate reaction by adding 50 microliters of 3 M NaOH.

14. Read absorbance at 405 nm in modified ELISA reader [Hewlett Packard, Stanford, Calif.].

Figure 16:
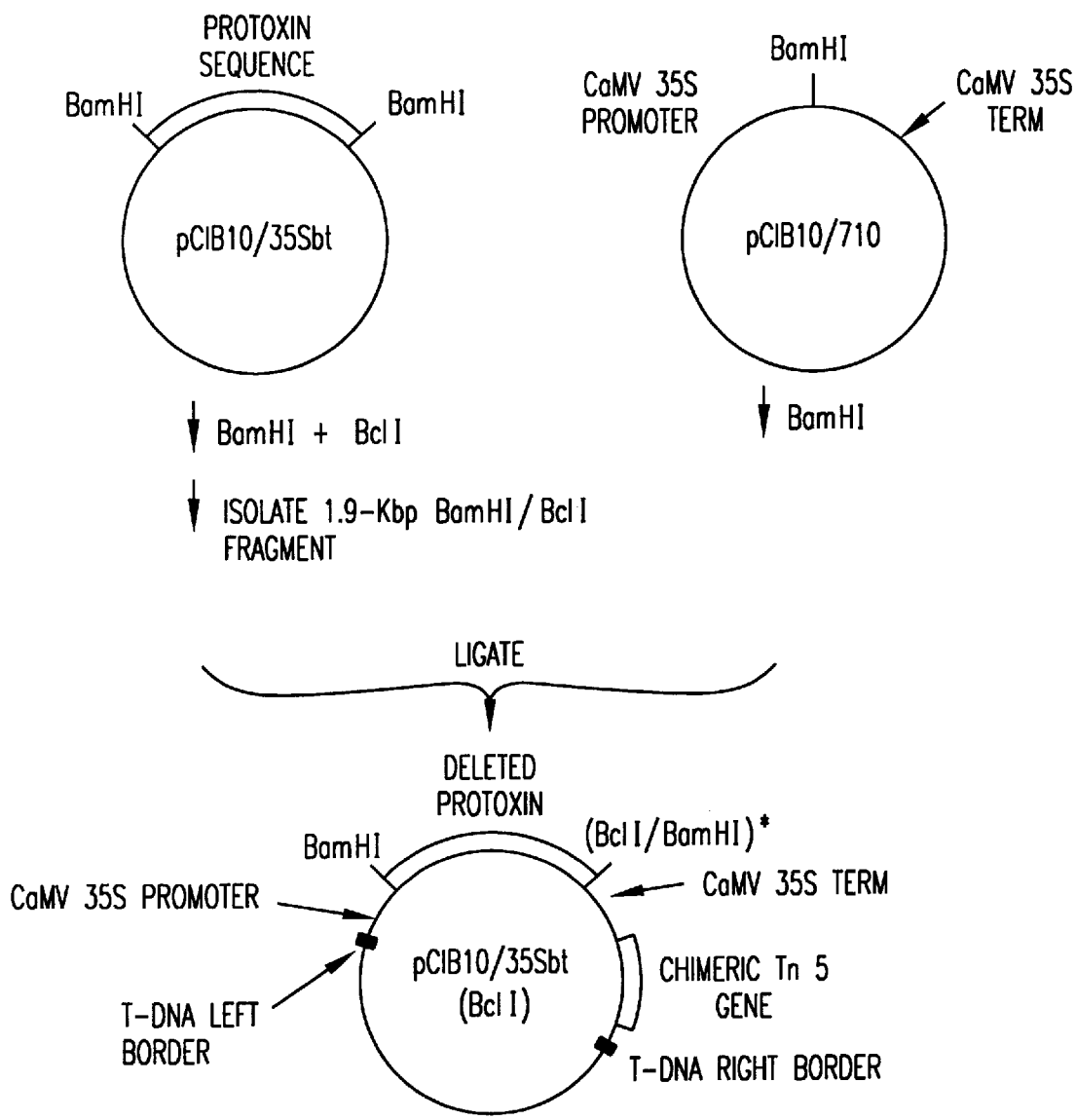
FIG. 16. Construction of pCIB10/35SBt(BclI).
Figure 17:
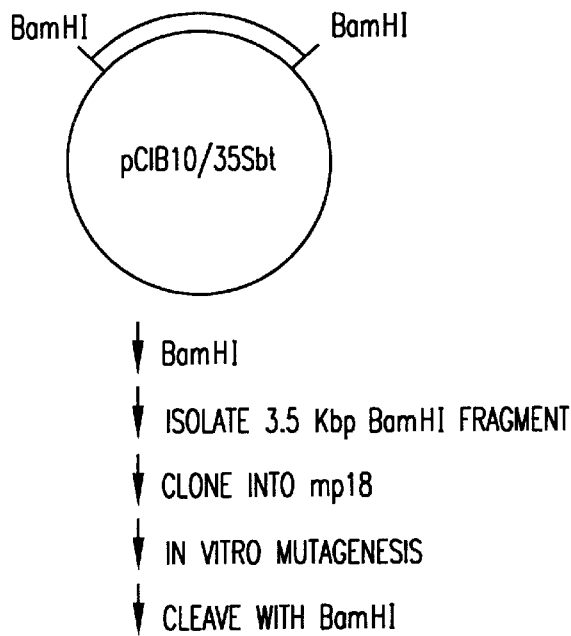
FIG. 17. Construction of pCIB10/35SBt(607).
Figure 17:
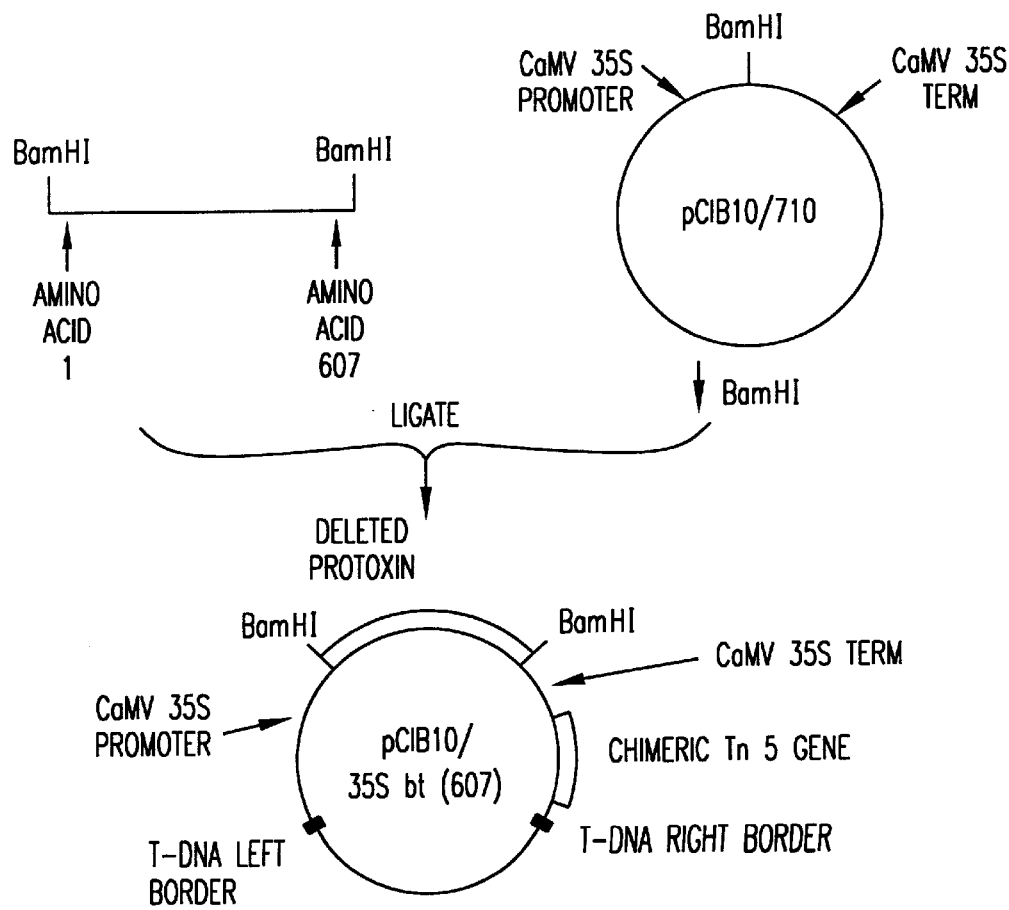

Plant tissue transformed with the pCIB10/35SBt(BclI) [see FIG. 16] construction, when assayed using this ELISA procedure shows a positive reaction, indicating expression of the Bt gene.

EXAMPLE 27

Elisa Buffers

| EPBS (ELISA Phosphate Buffered Saline) | |
|---|---|
| 10 mM NaPhosphate: | |
| Na$_2$HPO$_4$ | 4.68 grams/4 liters. |
| | NaH$_2$PO$_4$.H$_2$O |
| 0.976 grams/4 liters | |
| 140 mM NaCl | |
| NaCl | 32.7 grams/4 liters |
| pH should be approximately 7.4 | |

-continued

| Borate Buffered Saline |
|---|
| 100 mM Boric acid |
| 25 mM Na Borate |
| 75 mM NaCl |
| Adjust pH to 8.4–8.5 with HCl or NaOH as needed. |
| ELISA Blocking Buffer |
| In EPBS, |
| 1% BSA |
| 0.02% Na azide |
| ELISA Wash Buffer |
| 10 mM Tris-HCl pH 8.0 |
| 0.05% Tween 20 |
| 0.02% Na Azide |
| 2.5M TRIS |
| ELISA Diluent |
| In EPBS: |
| 0.05% Tween 20 |
| 1% BSA |
| 0.02% Na Azide |
| ELISA Substrate Buffer |
| In 500 mls, |
| 48 ml Diethanolamine, |
| 24. 5 mg MgCl$_2$; |
| adjust to pH 9.8 with HCl. |
| ELISA Substrate |
| 15 mg p-nitrophenyl phosphate in 25 ml Substrate Buffer |

EXAMPLE 28

Transformation of Cotton Cells to Insect Resistance and Bioassay of Transformed Cotton Cells Transformed embryogenic cotton cultures are obtained as in Example 24, with the variation that the vector used also contains the delected *Bacillus thuringiensis* protoxin gene with the CaMV 35S promoter described in Example 8.

Following hygromycin selection, antibiotic-resistant embryos and cell clumps are individually transferred to separate petri plates with fresh callus growth medium containing hygromycin (100 mg/L) and allowed to grow until the fresh weight of the culture is between 0.1 g and 0.5 g. At this point, each culture is a mixture of embryogenic cells, cell clumps, and embryos and is judged to be transformed based on the demonstrated phenotype of hygromycin resistance. Each culture is subdivided in half. One half is maintained on callus growth medium lacking hygromycin, with the variation that the other part is maintained on medium that also contains hygromycin (100 mg/L). After a three week period of growth, the culture maintained in the absence of hygromycin selection is then used for the feeding bioassay. The following example gives the data from such an assay.

*Heliothis virescens* eggs laid on sheets of cheesecloth are obtained from the CIBA-GEIGY Corporation in Vero Beach, Fla. The cheesecloth sheets are transferred to a large covered glass beaker and incubated at 29 degrees C. with wet paper towels to maintain humidity. The eggs hatch within three days. As soon as possible after hatching, the larvae are transferred to the transformed embryogenic cotton cultures. Usually six (6) larvae are placed on each culture. Controls are cotton callus cultures which are not transformed. The number and size of the larvae are scored after a six day period of growth by grouping the larvae into the following classes: class 0=larvae dead; class 1=larvae 0–5 mm in length; class 2=larvae 5–10 mm in length; class 3=larvae 10–15 mm in length. Four control and 23 transformed plant cultures are assayed.

The data obtained are as follows:

| Sample | # larvae Scored | % in class 0 | 1 | 2 | 3 |
|---|---|---|---|---|---|
| control | 23 | 4% | | | 96% |
| transformed | 106 | 54% | 6% | 23% | 17% |

In addition to the increased mortality and smaller size of the Heliothis larvae place don transformed cotton callus relative to control callus, the feeding behavior of the larvae on transformed samples is also different from the controls. Larvae on the transformed callus often stopped feeding and left the callus entirely.

Plant cultures for which no larvae feeding on them reached 10 mm in length are judged to have significant insecticidal activity compared to that of the controls. The portion of those cultures maintained separately on hygromycin selection was then plated and germinated to produce insecticidal plants according to the procedure of Example 24.

EXAMPLE 29

Figure 19:
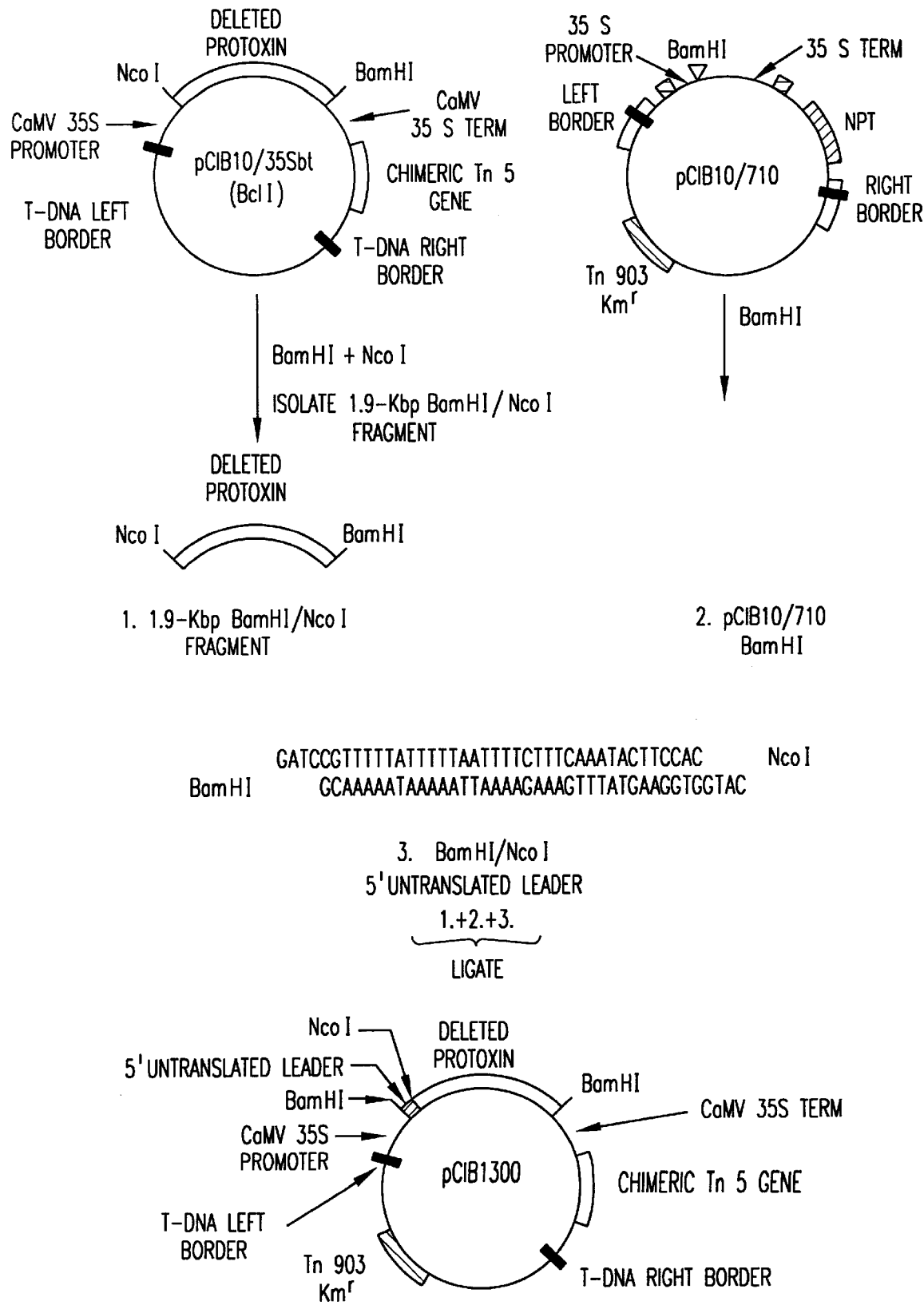
FIG. 19. Construction of pCIB1300, a plasmid having a chimeric gene containing the CaMV 35S promoter/AMV leader/Bt(Bcl)deletion/35S terminator.

Construction of pCIB1300, for High Level Expression in Plants pCIB1300 is engineered for high level expression of the Bt gene and contains an untranslated leader sequence 5' to the Bt gene to enhance expression in plants. The untranslated leader is a 40 bp sequence 5' to the initiation codon of the Bt gene and 3' to the CaMV 35S untranslated leader. The final pCIB1300 construct is engineered by the insertion of the 40 bp leader and deleted Bt gene into the BamH1 site of pCIB10/710 as shown in FIG. 19. A 1.9 kb NcoI-BamH1 fragment from pCIB10/35S Bt(Bcl) deletion is purified in low-gelling temperature agarose. The 40 bp leader is chemically synthesized as a double-stranded oligonucleotide with a 5' overhanging Bamh1 site and a 3' overhanging Nco1 site using an Applied Biosystems DNA Synthesizer. The sequence of the untranslated leader as shown in the center of FIG. 19 is derived from the alfalfa mosaic virus (AMV) coat protein untranslated leader described by Koper-Zwarthoff et al. [Koper-Zwarthoff, E. C., Lockard, R. E., Alzner-DeWeerd, B., RajBhandary, U. L. and J. F. Bol (1977) Proc. Natl. Acad. Sci. USA 74: 5504–5508]. The 40 bp leader, 1.9 kb Bt fragment and BamH1 linearized pCIB710 vector are joined in a three-part ligation using T4 DNA ligase to construct pCIB1300.

EXAMPLE 30

Isolation of cDNA Clones Coding for the Small Subunit of RuBPCase in Cotton

*Gossypium hirsutum* (Funk line RF522) plants are grown from seeds in the greenhouse with 14 hour daily light periods. Total RNA is isolated from young green leaves following the procedure of Newbury and Possingham (Plant Physiology 1977, 60: 543). PolyA$^+$ RNA is purified as described in Maniatis et al. 1982 p.197. Double-stranded cDNA (complementary DNA) is synthesized according to the procedure of Okayama and Berg (Mol. Cell. Biol. 1982, 2:161) with the following modifications:

A. First strand cDNA is primed with oligo-dT;
    B. After tailing the double-stranded cDNA with oligo-dG using polynucleotidyl-transferase, it is cloned into oligo-dC tailed pUC9 (Pst I site—from Pharmacia), and annealed; and
    C. The DNA is transformed into *E. coli* strain HB101.

Since, with the chlorophyll a/b (Cab) binding protein, RuBPCase is the most abundant protein in green leaves, we then screened our cDNA library for cDNA clones of the most abundant mRNAs. Nitrocellulose (Schleicher and Schuell) filter replicas of the cDNA clones are screened with the first cDNA strand, radioactively labeled with alpha-dCT$^{32}$P and reverse-transcriptase, the template being the same polyA$^+$ RNA as that used to construct the cDNA library. Six cDNA clones out of 275, are selected and analyzed further.

Northern analysis (done as described in Maniatis et al. 1982, p. 202) shows that two of these cDNA clones hybridize to a class of mRNA about 1100 nt long. They cross-hybridize with a Cab probe from tobacco. The other four hybridize to a class of mRNA 900 to 1000 nt long, a size consistent with that of the rbcS (small subunit of Rubisco). Cotton leaf mRNA, after hybrid selection using one of these four cDNA clones, is released and translated in vitro (as described in Maniatis et al. 1982, p.329) using rabbit reticulocytes in vitro translation kit (Promega Biotec). Electrophoresis on polyacrylamide gel of the translation products showed one major polypeptide of about 20 Kd, a molecular weight consistent with that of the precursor of the rbcS. The other 3 cDNA clones cross-hybridize with the clone used for the hybrid-release experiment.

Large portions of these cDNA clones are sequenced, using the dideoxy chain-termination technique (Sanger et al., 1977) after subcloning into M13. Comparison of their sequences with formerly published rbcS sequences from other species showed that they are indeed rbcS cDNA clones.

EXAMPLE 31

Isolation of Genomic clones of Small Subunit RuBPcase of Cotton

A. Cotton Genomic Southern Analysis

Genomic Southern blots are prepared by standard procedures using nitrocellulose filters. Prehybridization, hybridization and washing conditions are as described in Klessig et al. (Plant Mol. Biol. Reporter, 1983, 1:12). Genomic Southern analysis, using our rbcS cDNA clone as a probe, revealed 4 to 5 genomic fragments depending on the restriction enzyme used to digest the DNA. As expected, the rbcS is encoded by a small gene family in cotton, as in other species previously studied by others. The cotton rbcS multigene family is estimated to contain at least 5 members.

B. Isolation of rbcS Genomic Clones

In order to construct a cotton genomic library, partial Sau3a digests of cotton genomic DNA are size-fractionated on a 10% to 40% sucrose-gradient, and ligated into Lambda EMBL3 arms (Stratagene) digested with Bam HI. Packaging of Lambda recombinants, done using Packagene kit (Stratagene), is followed by transfection into *E. coli* strain K802. Nitrocellulose filter duplicate replicas are screened as described in Maniatis et al. 1982 p.320, using our rbcS cDNA clone from above as a probe. Twelve positive clones out of 450,000 plaques are purified. DNA is isolated from plate lysates of these recombinants phages, as described in Maniatis et al. (1982, p.80).

43

Figure 24:
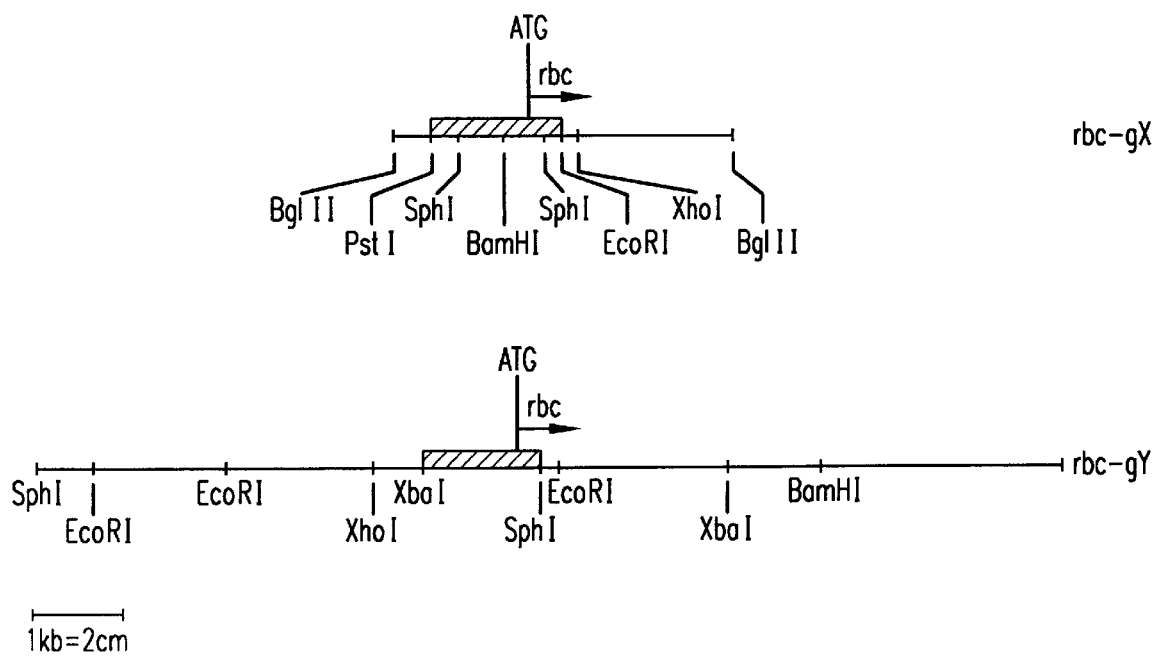
FIG. 24. Restriction map of the cotton genomic clones carrying rbc-gX and rbc-gY.

After comparing these genomic clones by their restriction digest pattern with various enzymes, five different rbcS genes are identified. Each one is subcloned into the plasmid vector pBSM13+ (Stratagene). These subclones are then mapped and partially sequenced in order to localize the 5' end of the gene and the first ATG (translational start site) of the transit peptide. A map of two of these genomic subclones, rbc-gX and rbc-gY is shown on FIG. 24. The Lambda EMBL3 phages containing the genomic DNA of subclones rbc-gX and rbc-gY have been deposited with the American Type Culture Collection.

C. Study of the Level of Expression of the rbcS Genes in Cotton Leaves

Forty-one additional rbcS cDNA clones are isolated from the cotton leaf cDNA library. Restriction mapping analysis, sequencing and hybrization of these cDNA clones to gene specific probes allows us to conclude that the gene carried by the genomic clone rbc-gX is responsible for about 17% of the leaf rbcS transcripts.

EXAMPLE 32

Construction of Chimeric Genes Using Cotton rbcS Promoter

A. Insertion of an Nco I Site at the First ATG of the rbcS Transit Peptides

The sequences of the transit peptides of the rbc-gX and rbc-gY are shown on FIGS. 26 and 25 respectively. An Nco I cleavage site (CCATGG) is introduced at the first ATG of the transit peptide of these two genes. This is done by cloning the PstI-EcoRI fragment of gene rbc-gX and the XbaI-SphI fragment of gene rbc-gY (hatched fragments on FIGS. 22 and 23 respectively) into mp18 and mp19 respectively, and using standard oligonucleotide site-directed mutagenesis procedures described above to introduce the NcoI site.

44

Figure 20:
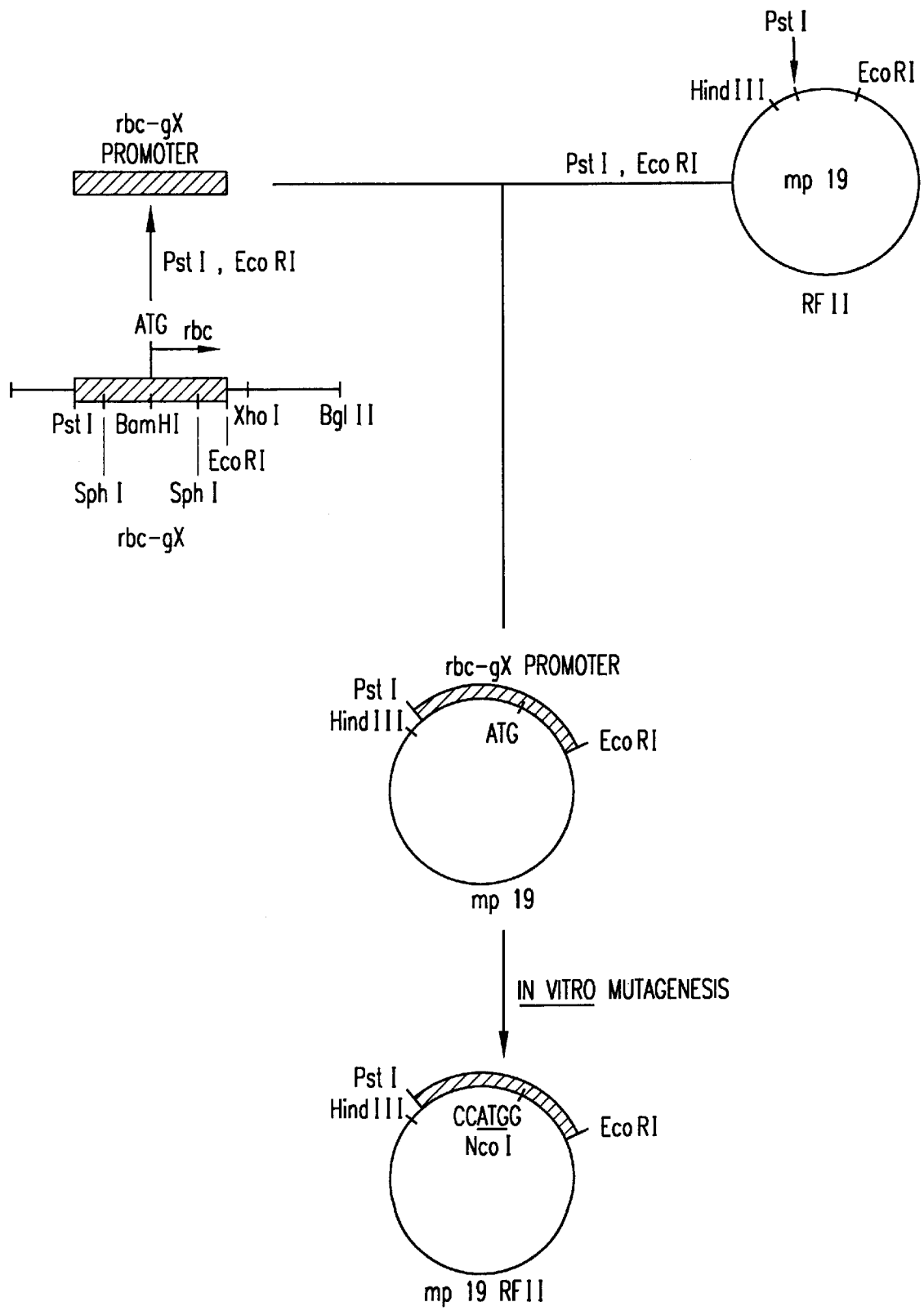
FIGS. 20, 21, and 22: Construction of pCIB 1301, having a chimeric gene containing the cotton rbc-gX promoter/Bt (607deletion) coding sequence.
Figure 21:
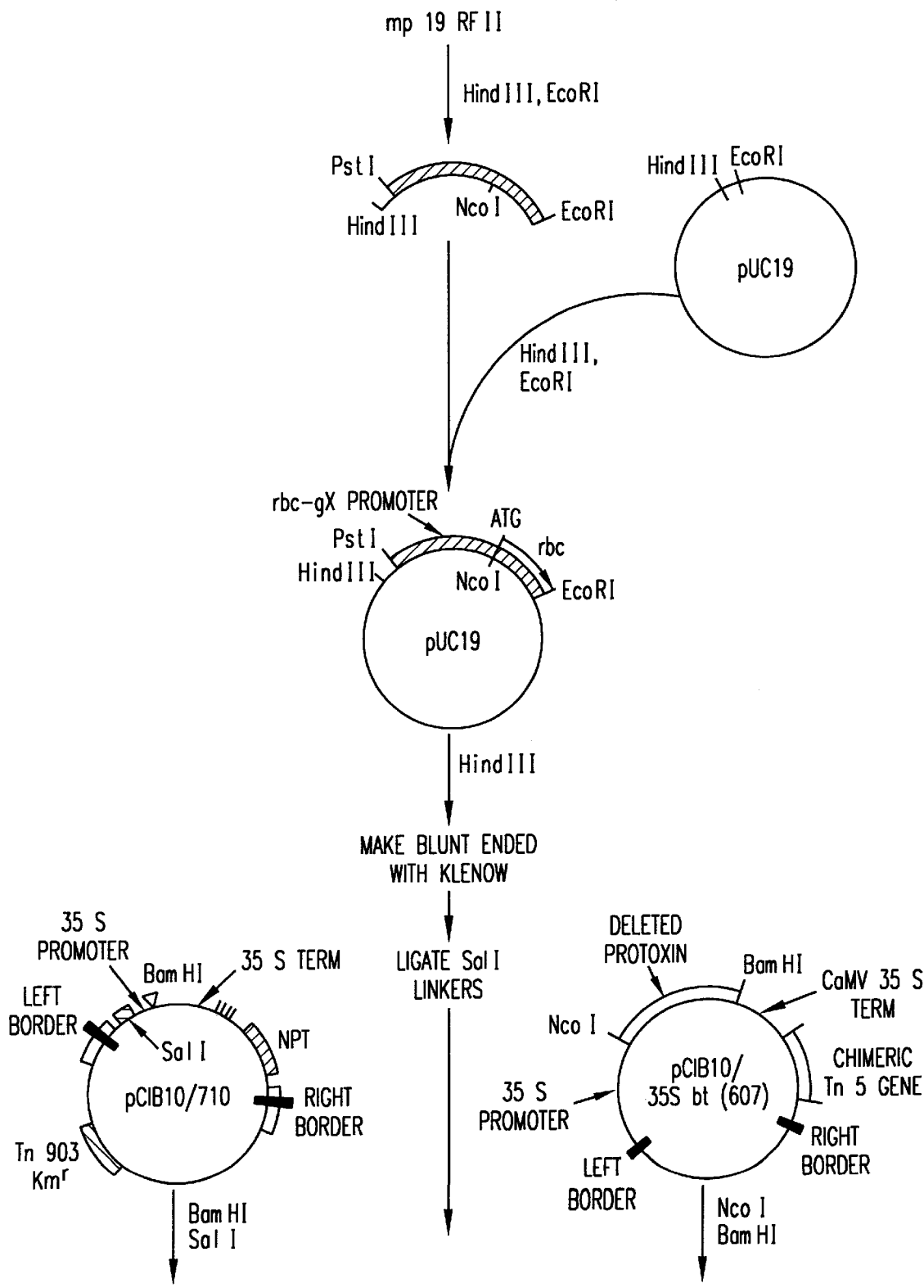
Figure 22:
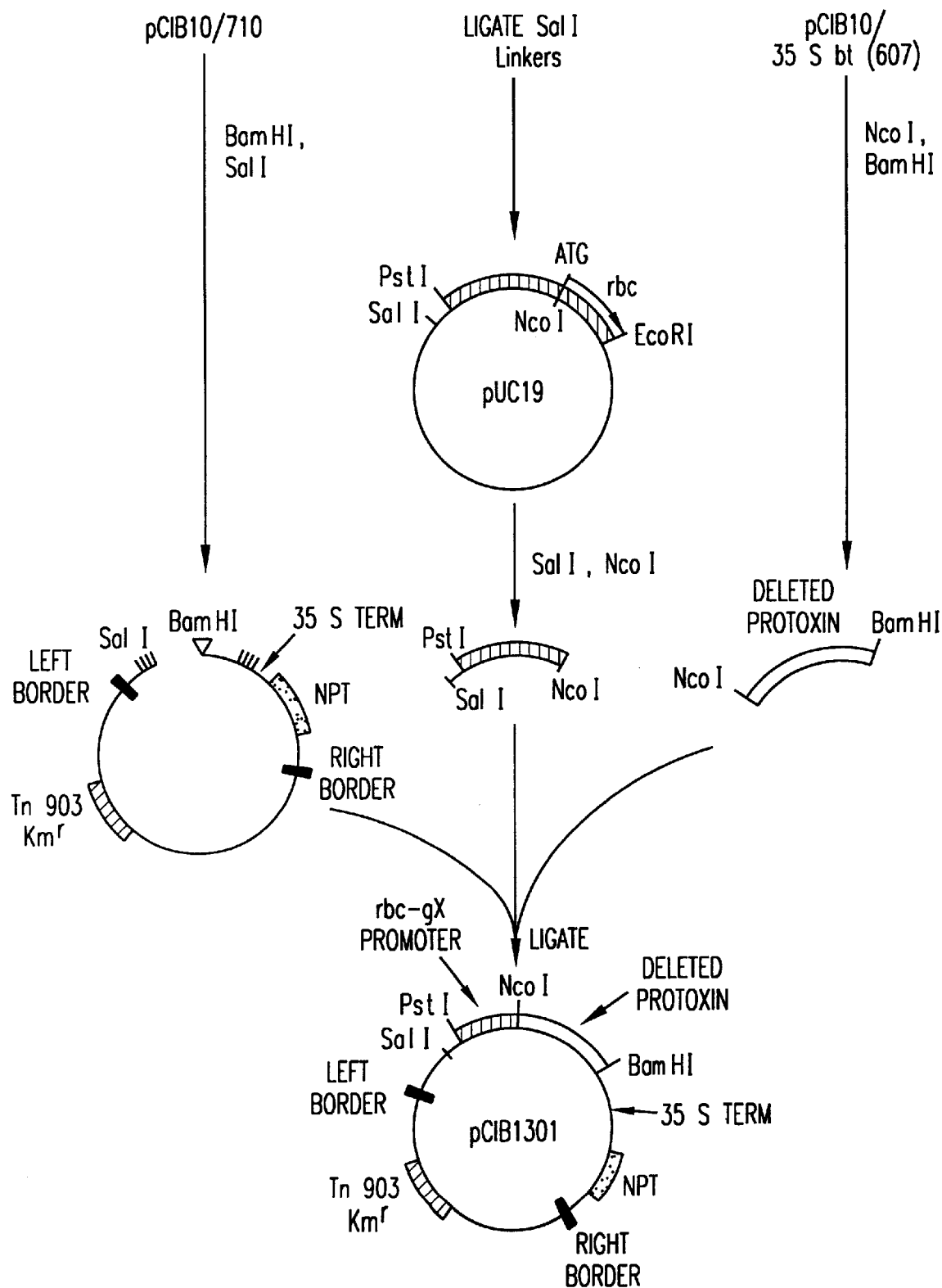

B. Construction of pCIB 1301, a Plasmid Bearing a Chimeric Gene Containing the Deleted *Bacillus thuringiensis* Protoxin Gene (607 Deletion) with the rbc-gX Gene Promoter After the site-directed mutagenesis, double-stranded replicative form DNA is isolated from the M13 clone, which is then digested with Hind III and Eco RI. The Hind III-Eco RI fragment containing the rbc-gX promoter is ligated together with Hind III and Eco RI digested plasmid pUC19 and the ligation mix then transformed into *E. coli* strain HB101. Plasmid DNA is isolated from ampicillin-selected transformants and digested with HindIII. The ends of the resulting molecule are made blunt-ended by treatment with the Klenow subunit of DNA polymerase I and Sal I linkers are ligated to these ends. The resulting linear molecule is digested with Sal I and Nco I and gel-purified. In a three-part ligation the gel-purified Sal I-Nco I fragment is joined to a gel-purified Bam HI-Sal I fragment from pCIB770, a broad-host range replicon used as an Agrobacterium Ti plasmid cloning vector (Rothstein, et al.[1987] Gene 53: 153–161) and a gel-purified Nco I-Bam HI fragment containing the truncated 607 amino acid Bt gene. The ligation mix is transformed into *E. coli* strain HB101. The resulting plasmid, pCIB1301, which is depicted graphically in FIGS. 20, 21, and 22, is selected on kanamycin.

Figure 23:
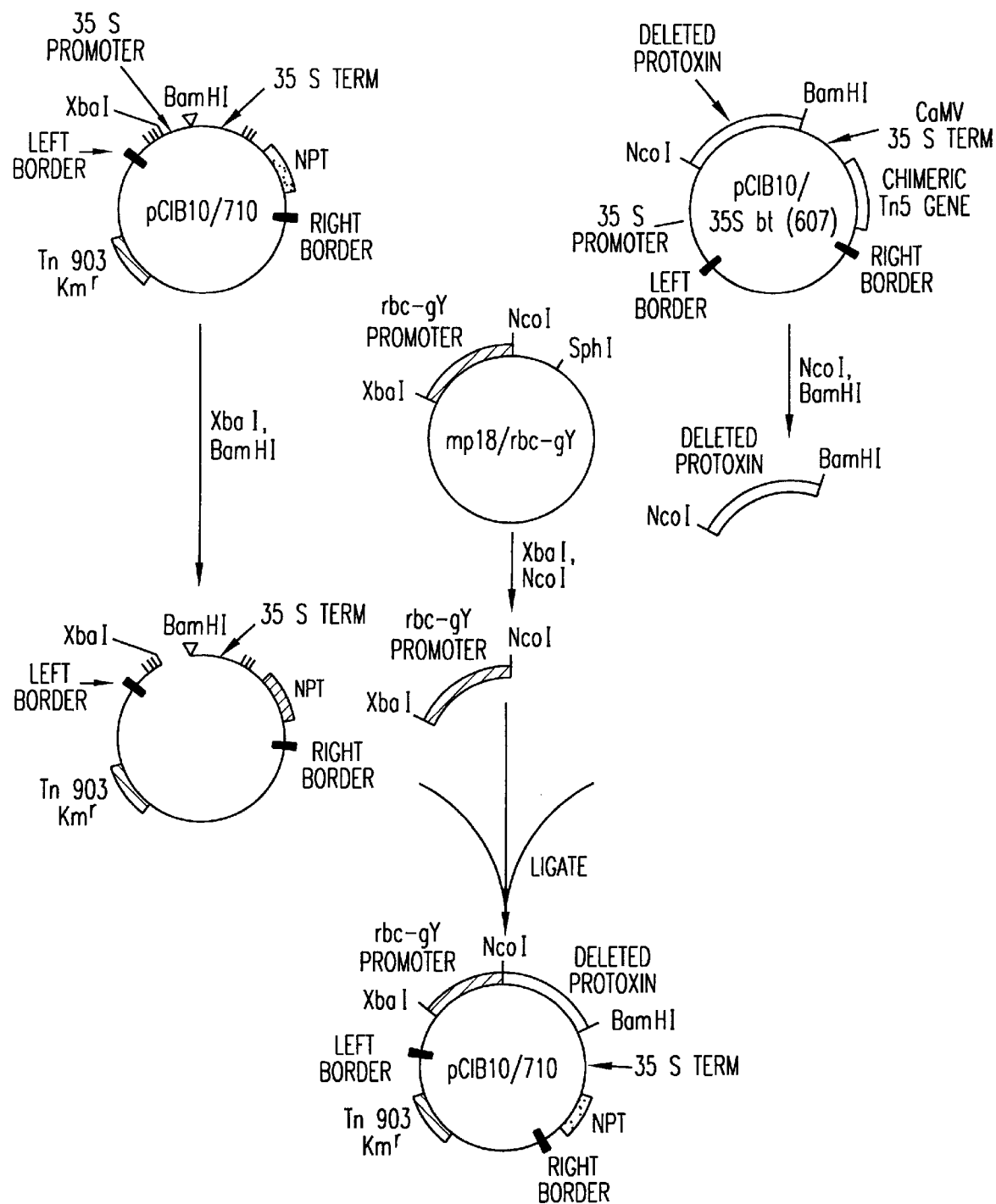
FIG. 23. Construction of pCIB1302, having a chimeric gene containing the cotton rbc-gY promoter/Bt(607deletion) coding sequence.

C. Construction of pCIB1302, a Plasmid Bearing a Chimeric Gene Containing the Deleted *Bacillus thuringiensis* Protoxin Gene (607 Deletion) with the rbc-gY Gene Promoter After the mutagenesis, double-stranded replicative form DNA is isolated from the M13 clone, which is then digested with Xba I-Nco I. The approximately 1.97 kb Nco I-Bam HI fragment, containing the deleted protoxin gene, is then ligated, together with the Xba I-Nco I rbc-gY promoter fragment, in a three way ligation, into Xba I-Bam HI cleaved pCIB10/710. The resulting plasmid, pCIB1302, the structure of which is shown in FIG. 23, is selected on kanamycin.

What we claim is:

1. An isolated DNA molecule comprising a nucleic acid fragment having the sequence of:
   (a) the approximately 1 kb DNA fragment of genomic clone rbc-gY (ATCC Accession No. 40486) between the XbaI site and the translation start site of the coding region of the cotton small subunit ribulose biphosphate carboxylase gene; or
   (b) the approximately 1 kb DNA fragment of genomic clone rbc-gX (ATCC Accession No. 40487) between the PstI site and the translation start site of the coding region of the ribulose biphosphate carboxylase gene.

2. The isolated DNA molecule of claim 1, wherein said DNA molecule comprises a nucleic acid fragment having the sequence of the approximately 1 kb DNA fragment of genomic clone rbc-gY (ATCC Accession No. 40486) between the XbaI site and the translation start site of the coding region of the cotton small subunit ribulose biphosphate carboxylase gene.

3. The isolated DNA molecule of claim 1, wherein said DNA molecule comprises a nucleic acid fragment having the sequence of the approximately 1 kb DNA fragment of genomic clone rbc-gX (ATCC Accession No. 40487) between the PstI site and the translation start site of the coding region of the cotton small subunit ribulose biphosphate carboxylase gene.

4. A chimeric gene comprising the DNA molecule of claim 2.

5. A chimeric gene comprising the DNA molecule of claim 3.

6. A vector comprising the DNA molecule of claim 2.

7. A vector comprising the DNA molecule of claim 3.

8. A bacterial or plant host cell comprising the chimeric gene of claim 4.

9. A bacterial or plant host cell comprising the chimeric gene of claim 5.

10. The host cell of claim 8, which is a plant cell.

11. The host cell of claim 9, which is a plant cell.

12. A plant comprising a plant cell of claim 10.

13. A plant comprising a plant cell of claim 11.

14. The plant of claim 12, which is a cotton plant.

15. The plant of claim 13, which is a cotton plant.

* * * * *

UNITED STATES PATENT AND TRADEMARK OFFICE
CERTIFICATE OF CORRECTION

PATENT NO. : 6,040,504
DATED : March 21, 2000
INVENTOR(S) : Douglas Rice et al.

It is certified that error appears in the above-identified patent and that said Letters Patent is hereby corrected as shown below:

Title page,
Item [75], Inventors: Annick de Framond, Pittsboro, N.C.; Douglas Rice, Des Moines, Iowa Signed and Sealed this First Day of January, 2002

Attest:

JAMES E. ROGAN
Attesting Officer
Director of the United States Patent and Trademark Office

SEQUENCE LISTING

```
<160> NUMBER OF SEQ ID NOS: 6

<210> SEQ ID NO 1
<211> LENGTH: 4360
<212> TYPE: DNA
<213> ORGANISM: Bacillus thuringiensis
<220> FEATURE:
<221> NAME/KEY: CDS
<222> LOCATION: (156)..(3623)

<400> SEQUENCE: 1
gttaacaccc tgggtcaaaa attgatattt agtaaaatta gttgcactttt gtgcattttt         60 tcataagatg agtcatatgt tttaaattgt agtaatgaaa aacagtatta tatcataatg        120
aattggtatc ttaataaaag agatggaggt aactt atg gat aac aat ccg aac         173
                                      Met Asp Asn Asn Pro Asn
                                      1               5 atc aat gaa tgc att cct tat aat tgt tta agt aac cct gaa gta gaa         221
Ile Asn Glu Cys Ile Pro Tyr Asn Cys Leu Ser Asn Pro Glu Val Glu
           10                  15                  20 gta tta ggt gga gaa aga ata gaa act ggt tac acc cca atc gat att         269
Val Leu Gly Gly Glu Arg Ile Glu Thr Gly Tyr Thr Pro Ile Asp Ile
       25                  30                  35 tcc ttg tcg cta acg caa ttt ctt ttg agt gaa ttt gtt ccc ggt gct         317
Ser Leu Ser Leu Thr Gln Phe Leu Leu Ser Glu Phe Val Pro Gly Ala
```

```
                40                          45                          50
gga ttt gtg tta gga cta gtt gat ata ata tgg gga att ttt ggt ccc          365
Gly Phe Val Leu Gly Leu Val Asp Ile Ile Trp Gly Ile Phe Gly Pro
 55                      60                      65                  70 tct caa tgg gac gca ttt ctt gta caa att gaa cag tta att aac caa          413
Ser Gln Trp Asp Ala Phe Leu Val Gln Ile Glu Gln Leu Ile Asn Gln
             75                      80                      85 aga ata gaa gaa ttc gct agg aac caa gcc att tct aga tta gaa gga          461
Arg Ile Glu Glu Phe Ala Arg Asn Gln Ala Ile Ser Arg Leu Glu Gly
                 90                      95                     100 cta agc aat ctt tat caa att tac gca gaa tct ttt aga gag tgg gaa          509
Leu Ser Asn Leu Tyr Gln Ile Tyr Ala Glu Ser Phe Arg Glu Trp Glu
            105                     110                     115 gca gat cct act aat cca gca tta aga gaa gag atg cgt att caa ttc          557
Ala Asp Pro Thr Asn Pro Ala Leu Arg Glu Glu Met Arg Ile Gln Phe
        120                     125                     130 aat gac atg aac agt gcc ctt aca acc gct att cct ctt ttt gca gtt          605
Asn Asp Met Asn Ser Ala Leu Thr Thr Ala Ile Pro Leu Phe Ala Val
135                     140                     145                 150 caa aat tat caa gtt cct ctt tta tca gta tat gtt caa gct gca aat          653
Gln Asn Tyr Gln Val Pro Leu Leu Ser Val Tyr Val Gln Ala Ala Asn
                155                     160                     165 tta cat tta tca gtt ttg aga gat gtt tca gtg ttt gga caa agg tgg          701
Leu His Leu Ser Val Leu Arg Asp Val Ser Val Phe Gly Gln Arg Trp
            170                     175                     180 gga ttt gat gcc gcg act atc aat agt cgt tat aat gat tta act agg          749
Gly Phe Asp Ala Ala Thr Ile Asn Ser Arg Tyr Asn Asp Leu Thr Arg
        185                     190                     195 ctt att ggc aac tat aca gat cat gct gta cgc tgg tac aat acg gga          797
Leu Ile Gly Asn Tyr Thr Asp His Ala Val Arg Trp Tyr Asn Thr Gly
    200                     205                     210 tta gag cgt gta tgg gga ccg gat tct aga gat tgg ata aga tat aat          845
Leu Glu Arg Val Trp Gly Pro Asp Ser Arg Asp Trp Ile Arg Tyr Asn
215                     220                     225                 230 caa ttt aga aga gaa tta aca cta act gta tta gat atc gtt tct cta          893
Gln Phe Arg Arg Glu Leu Thr Leu Thr Val Leu Asp Ile Val Ser Leu
                235                     240                     245 ttt ccg aac tat gat agt aga acg tat cca att cga aca gtt tcc caa          941
Phe Pro Asn Tyr Asp Ser Arg Thr Tyr Pro Ile Arg Thr Val Ser Gln
            250                     255                     260 tta aca aga gaa att tat aca aac cca gta tta gaa aat ttt gat ggt          989
Leu Thr Arg Glu Ile Tyr Thr Asn Pro Val Leu Glu Asn Phe Asp Gly
        265                     270                     275 agt ttt cga ggc tcg gct cag ggc ata gaa gga agt att agg agt cca         1037
Ser Phe Arg Gly Ser Ala Gln Gly Ile Glu Gly Ser Ile Arg Ser Pro
    280                     285                     290 cat ttg atg gat ata ctt aac agt ata acc atc tat acg gat gct cat         1085
His Leu Met Asp Ile Leu Asn Ser Ile Thr Ile Tyr Thr Asp Ala His
295                     300                     305                 310 aga gga gaa tat tat tgg tca ggg cat caa ata atg gct tct cct gta         1133
Arg Gly Glu Tyr Tyr Trp Ser Gly His Gln Ile Met Ala Ser Pro Val
                315                     320                     325 ggg ttt tcg ggg cca gaa ttc act ttt ccg cta tat gga act atg gga         1181
Gly Phe Ser Gly Pro Glu Phe Thr Phe Pro Leu Tyr Gly Thr Met Gly
            330                     335                     340 aat gca gct cca caa caa cgt att gtt gct caa cta ggt cag ggc gtg         1229
Asn Ala Ala Pro Gln Gln Arg Ile Val Ala Gln Leu Gly Gln Gly Val
        345                     350                     355 tat aga aca tta tcg tcc act tta tat aga aga cct ttt aat ata ggg         1277
```

```
                 Tyr Arg Thr Leu Ser Ser Thr Leu Tyr Arg Arg Pro Phe Asn Ile Gly
                     360                 365                 370 ata aat aat caa caa cta tct gtt ctt gac ggg aca gaa ttt gct tat     1325
Ile Asn Asn Gln Gln Leu Ser Val Leu Asp Gly Thr Glu Phe Ala Tyr
375                 380                 385                 390 gga acc tcc tca aat ttg cca tcc gct gta tac aga aaa agc gga acg     1373
Gly Thr Ser Ser Asn Leu Pro Ser Ala Val Tyr Arg Lys Ser Gly Thr
                    395                 400                 405 gta gat tcg ctg gat gaa ata ccg cca cag aat aac aac gtg cca cct     1421
Val Asp Ser Leu Asp Glu Ile Pro Pro Gln Asn Asn Asn Val Pro Pro
                410                 415                 420 agg caa gga ttt agt cat cga tta agc cat gtt tca atg ttt cgt tca     1469
Arg Gln Gly Phe Ser His Arg Leu Ser His Val Ser Met Phe Arg Ser
            425                 430                 435 ggc ttt agt aat agt agt gta agt ata ata aga gct cct atg ttc tct     1517
Gly Phe Ser Asn Ser Ser Val Ser Ile Ile Arg Ala Pro Met Phe Ser
        440                 445                 450 tgg ata cat cgt agt gct gaa ttt aat aat ata att cct tca tca caa     1565
Trp Ile His Arg Ser Ala Glu Phe Asn Asn Ile Ile Pro Ser Ser Gln
455                 460                 465                 470 att aca caa ata cct tta aca aaa tct act aat ctt ggc tct gga act     1613
Ile Thr Gln Ile Pro Leu Thr Lys Ser Thr Asn Leu Gly Ser Gly Thr
                    475                 480                 485 tct gtc gtt aaa gga cca gga ttt aca gga gga gat att ctt cga aga     1661
Ser Val Val Lys Gly Pro Gly Phe Thr Gly Gly Asp Ile Leu Arg Arg
                490                 495                 500 act tca cct ggc cag att tca acc tta aga gta aat att act gca cca     1709
Thr Ser Pro Gly Gln Ile Ser Thr Leu Arg Val Asn Ile Thr Ala Pro
            505                 510                 515 tta tca caa aga tat cgg gta aga att cgc tac gct tct acc aca aat     1757
Leu Ser Gln Arg Tyr Arg Val Arg Ile Arg Tyr Ala Ser Thr Thr Asn
        520                 525                 530 tta caa ttc cat aca tca att gac gga aga cct att aat cag ggg aat     1805
Leu Gln Phe His Thr Ser Ile Asp Gly Arg Pro Ile Asn Gln Gly Asn
535                 540                 545                 550 ttt tca gca act atg agt agt ggg agt aat tta cag tcc gga agc ttt     1853
Phe Ser Ala Thr Met Ser Ser Gly Ser Asn Leu Gln Ser Gly Ser Phe
                    555                 560                 565 agg act gta ggt ttt act act ccg ttt aac ttt tca aat gga tca agt     1901
Arg Thr Val Gly Phe Thr Thr Pro Phe Asn Phe Ser Asn Gly Ser Ser
                570                 575                 580 gta ttt acg tta agt gct cat gtc ttc aat tca ggc aat gaa gtt tat     1949
Val Phe Thr Leu Ser Ala His Val Phe Asn Ser Gly Asn Glu Val Tyr
            585                 590                 595 ata gat cga att gaa ttt gtt ccg gca gaa gta acc ttt gag gca gaa     1997
Ile Asp Arg Ile Glu Phe Val Pro Ala Glu Val Thr Phe Glu Ala Glu
        600                 605                 610 tat gat tta gaa aga gca caa aag gcg gtg aat gag ctg ttt act tct     2045
Tyr Asp Leu Glu Arg Ala Gln Lys Ala Val Asn Glu Leu Phe Thr Ser
615                 620                 625                 630 tcc aat caa atc ggg tta aaa aca gat gtg acg gat tat cat att gat     2093
Ser Asn Gln Ile Gly Leu Lys Thr Asp Val Thr Asp Tyr His Ile Asp
                    635                 640                 645 caa gta tcc aat tta gtt gag tgt tta tct gat gaa ttt tgt ctg gat     2141
Gln Val Ser Asn Leu Val Glu Cys Leu Ser Asp Glu Phe Cys Leu Asp
                650                 655                 660 gaa aaa aaa gaa ttg tcc gag aaa gtc aaa cat gcg aag cga ctt agt     2189
Glu Lys Lys Glu Leu Ser Glu Lys Val Lys His Ala Lys Arg Leu Ser
            665                 670                 675 gat gag cgg aat tta ctt caa gat cca aac ttt aga ggg atc aat aga     2237
Asp Glu Arg Asn Leu Leu Gln Asp Pro Asn Phe Arg Gly Ile Asn Arg
```

```
            680                 685                 690
caa cta gac cgt ggc tgg aga gga agt acg gat att acc atc caa gga    2285
Gln Leu Asp Arg Gly Trp Arg Gly Ser Thr Asp Ile Thr Ile Gln Gly
695                 700                 705                 710 ggc gat gac gta ttc aaa gag aat tac gtt acg cta ttg ggt acc ttt    2333
Gly Asp Asp Val Phe Lys Glu Asn Tyr Val Thr Leu Leu Gly Thr Phe
                715                 720                 725 gat gag tgc tat cca acg tat tta tat caa aaa ata gat gag tcg aaa    2381
Asp Glu Cys Tyr Pro Thr Tyr Leu Tyr Gln Lys Ile Asp Glu Ser Lys
        730                 735                 740 tta aaa gcc tat acc cgt tac caa tta aga ggg tat atc gaa gat agt    2429
Leu Lys Ala Tyr Thr Arg Tyr Gln Leu Arg Gly Tyr Ile Glu Asp Ser
            745                 750                 755 caa gac tta gaa atc tat tta att cgc tac aat gcc aaa cac gaa aca    2477
Gln Asp Leu Glu Ile Tyr Leu Ile Arg Tyr Asn Ala Lys His Glu Thr
760                 765                 770 gta aat gtg cca ggt acg ggt tcc tta tgg ccg ctt tca gcc cca agt    2525
Val Asn Val Pro Gly Thr Gly Ser Leu Trp Pro Leu Ser Ala Pro Ser
775                 780                 785                 790 cca atc gga aaa tgt gcc cat cat tcc cat cat ttc tcc ttg gac att    2573
Pro Ile Gly Lys Cys Ala His His Ser His His Phe Ser Leu Asp Ile
                795                 800                 805 gat gtt gga tgt aca gac tta aat gag gac tta ggt gta tgg gtg ata    2621
Asp Val Gly Cys Thr Asp Leu Asn Glu Asp Leu Gly Val Trp Val Ile
        810                 815                 820 ttc aag att aag acg caa gat ggc cat gca aga cta gga aat cta gaa    2669
Phe Lys Ile Lys Thr Gln Asp Gly His Ala Arg Leu Gly Asn Leu Glu
            825                 830                 835 ttt ctc gaa gag aaa cca tta gta gga gaa gca cta gct cgt gtg aaa    2717
Phe Leu Glu Glu Lys Pro Leu Val Gly Glu Ala Leu Ala Arg Val Lys
840                 845                 850 aga gcg gag aaa aaa tgg aga gac aaa cgt gaa aaa ttg gaa tgg gaa    2765
Arg Ala Glu Lys Lys Trp Arg Asp Lys Arg Glu Lys Leu Glu Trp Glu
855                 860                 865                 870 aca aat att gtt tat aaa gag gca aaa gaa tct gta gat gct tta ttt    2813
Thr Asn Ile Val Tyr Lys Glu Ala Lys Glu Ser Val Asp Ala Leu Phe
                875                 880                 885 gta aac tct caa tat gat aga tta caa gcg gat acc aac atc gcg atg    2861
Val Asn Ser Gln Tyr Asp Arg Leu Gln Ala Asp Thr Asn Ile Ala Met
        890                 895                 900 att cat gcg gca gat aaa cgc gtt cat agc att cga gaa gct tat ctg    2909
Ile His Ala Ala Asp Lys Arg Val His Ser Ile Arg Glu Ala Tyr Leu
            905                 910                 915 cct gag ctg tct gtg att ccg ggt gtc aat gcg gct att ttt gaa gaa    2957
Pro Glu Leu Ser Val Ile Pro Gly Val Asn Ala Ala Ile Phe Glu Glu
920                 925                 930 tta gaa ggg cgt att ttc act gca ttc tcc cta tat gat gcg aga aat    3005
Leu Glu Gly Arg Ile Phe Thr Ala Phe Ser Leu Tyr Asp Ala Arg Asn
935                 940                 945                 950 gtc att aaa aat ggt gat ttt aat aat ggc tta tcc tgc tgg aac gtg    3053
Val Ile Lys Asn Gly Asp Phe Asn Asn Gly Leu Ser Cys Trp Asn Val
                955                 960                 965 aaa ggg cat gta gat gta gaa gaa caa aac aac cac cgt tcg gtc ctt    3101
Lys Gly His Val Asp Val Glu Glu Gln Asn Asn His Arg Ser Val Leu
        970                 975                 980 gtt gtt ccg gaa tgg gaa gca gaa gtg tca caa gaa gtt cgt gtc tgt    3149
Val Val Pro Glu Trp Glu Ala Glu Val Ser Gln Glu Val Arg Val Cys
            985                 990                 995 ccg ggt cgt ggc tat atc ctt cgt gtc aca gcg tac aag gag gga tat    3197
Pro Gly Arg Gly Tyr Ile Leu Arg Val Thr Ala Tyr Lys Glu Gly Tyr
```

-continued

```
Pro Gly Arg Gly Tyr Ile Leu Arg Val Thr Ala Tyr Lys Glu Gly Tyr
    1000                1005                1010 gga gaa ggt tgc gta acc att cat gag atc gag aac aat aca gac gaa    3245
Gly Glu Gly Cys Val Thr Ile His Glu Ile Glu Asn Asn Thr Asp Glu
1015                1020                1025                1030 ctg aag ttt agc aac tgt gta gaa gag gaa gta tat cca aac aac acg    3293
Leu Lys Phe Ser Asn Cys Val Glu Glu Glu Val Tyr Pro Asn Asn Thr
                1035                1040                1045 gta acg tgt aat gat tat act gcg act caa gaa gaa tat gag ggt acg    3341
Val Thr Cys Asn Asp Tyr Thr Ala Thr Gln Glu Glu Tyr Glu Gly Thr
            1050                1055                1060 tac act tct cgt aat cga gga tat gac gga gcc tat gaa agc aat tct    3389
Tyr Thr Ser Arg Asn Arg Gly Tyr Asp Gly Ala Tyr Glu Ser Asn Ser
        1065                1070                1075 tct gta cca gct gat tat gca tca gcc tat gaa gaa aaa gca tat aca    3437
Ser Val Pro Ala Asp Tyr Ala Ser Ala Tyr Glu Glu Lys Ala Tyr Thr
    1080                1085                1090 gat gga cga aga gac aat cct tgt gaa tct aac aga gga tat ggg gat    3485
Asp Gly Arg Arg Asp Asn Pro Cys Glu Ser Asn Arg Gly Tyr Gly Asp
1095                1100                1105                1110 tac aca cca cta cca gct ggc tat gtg aca aaa gaa tta gag tac ttc    3533
Tyr Thr Pro Leu Pro Ala Gly Tyr Val Thr Lys Glu Leu Glu Tyr Phe
                1115                1120                1125 cca gaa acc gat aag gta tgg att gag atc gga gaa acg gaa gga aca    3581
Pro Glu Thr Asp Lys Val Trp Ile Glu Ile Gly Glu Thr Glu Gly Thr
            1130                1135                1140 ttc atc gtg gac agc gtg gaa tta ctt ctt atg gag gaa taa            3623
Phe Ile Val Asp Ser Val Glu Leu Leu Leu Met Glu Glu
        1145                1150                1155 tatatgcttt ataatgtaag gtgtgcaaat aaagaatgat tactgacttg tattgacaga  3683
taaataagga aattttata tgaataaaaa acgggcatca ctcttaaaag aatgatgtcc   3743 gtttttgta tgatttaacg agtgatattt aaatgttttt tttgcgaagg ctttacttaa   3803
cggggtaccg ccacatgccc atcaacttaa gaatttgcac tacccccaag tgtcaaaaaa  3863
cgttattctt tctaaaaagc tagctagaaa ggatgacatt ttttatgaat ctttcaattc  3923
aagatgaatt acaactattt tctgaagagc tgtatcgtca tttaacccct tctcttttgg  3983
aagaactcgc taaagaatta ggttttgtaa aaagaaaacg aaagttttca ggaaatgaat  4043
tagctaccat atgtatctgg ggcagtcaac gtacagcgag tgattctctc gttcgactat  4103
gcagtcaatt acacgccgcc acagcactct tatgagtcca gaaggactca ataaacgctt  4163
tgataaaaaa gcggttgaat ttttgaaata tatttttct gcattatgga aaagtaaact   4223
ttgtaaaaca tcagccattt caagtgcagc actcacgtat tttcaacgaa tccgtatttt  4283
agatgcgacg attttccaag taccgaaaca tttagcacat gtatatcctg ggtcaggtgg  4343
ttgtgcacaa actgcag                                                 4360

<210> SEQ ID NO 2
<211> LENGTH: 1155
<212> TYPE: PRT
<213> ORGANISM: Bacillus thuringiensis

<400> SEQUENCE: 2

Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30
```

-continued

```
Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                     85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445
```

-continued

```
Arg Ala Pro Met Phe Ser Trp Ile His Arg Ser Ala Glu Phe Asn Asn
450                     455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
            500                 505                 510
Val Asn Ile Thr Ala Pro Leu Ser Gln Arg Tyr Arg Val Arg Ile Arg
        515                 520                 525
Tyr Ala Ser Thr Thr Asn Leu Gln Phe His Thr Ser Ile Asp Gly Arg
530                 535                 540
Pro Ile Asn Gln Gly Asn Phe Ser Ala Thr Met Ser Ser Gly Ser Asn
545                 550                 555                 560
Leu Gln Ser Gly Ser Phe Arg Thr Val Gly Phe Thr Thr Pro Phe Asn
                565                 570                 575
Phe Ser Asn Gly Ser Ser Val Phe Thr Leu Ser Ala His Val Phe Asn
            580                 585                 590
Ser Gly Asn Glu Val Tyr Ile Asp Arg Ile Glu Phe Val Pro Ala Glu
        595                 600                 605
Val Thr Phe Glu Ala Glu Tyr Asp Leu Glu Arg Ala Gln Lys Ala Val
610                 615                 620
Asn Glu Leu Phe Thr Ser Ser Asn Gln Ile Gly Leu Lys Thr Asp Val
625                 630                 635                 640
Thr Asp Tyr His Ile Asp Gln Val Ser Asn Leu Val Glu Cys Leu Ser
                645                 650                 655
Asp Glu Phe Cys Leu Asp Glu Lys Lys Glu Leu Ser Glu Lys Val Lys
            660                 665                 670
His Ala Lys Arg Leu Ser Asp Glu Arg Asn Leu Leu Gln Asp Pro Asn
        675                 680                 685
Phe Arg Gly Ile Asn Arg Gln Leu Asp Arg Gly Trp Arg Gly Ser Thr
690                 695                 700
Asp Ile Thr Ile Gln Gly Gly Asp Asp Val Phe Lys Glu Asn Tyr Val
705                 710                 715                 720
Thr Leu Leu Gly Thr Phe Asp Glu Cys Tyr Pro Thr Tyr Leu Tyr Gln
                725                 730                 735
Lys Ile Asp Glu Ser Lys Leu Lys Ala Tyr Thr Arg Tyr Gln Leu Arg
            740                 745                 750
Gly Tyr Ile Glu Asp Ser Gln Asp Leu Glu Ile Tyr Leu Ile Arg Tyr
        755                 760                 765
Asn Ala Lys His Glu Thr Val Asn Val Pro Gly Thr Gly Ser Leu Trp
770                 775                 780
Pro Leu Ser Ala Pro Ser Pro Ile Gly Lys Cys Ala His His Ser His
785                 790                 795                 800
His Phe Ser Leu Asp Ile Asp Val Gly Cys Thr Asp Leu Asn Glu Asp
                805                 810                 815
Leu Gly Val Trp Val Ile Phe Lys Ile Lys Thr Gln Asp Gly His Ala
            820                 825                 830
Arg Leu Gly Asn Leu Glu Phe Leu Glu Glu Lys Pro Leu Val Gly Glu
        835                 840                 845
Ala Leu Ala Arg Val Lys Arg Ala Glu Lys Lys Trp Arg Asp Lys Arg
850                 855                 860
Glu Lys Leu Glu Trp Glu Thr Asn Ile Val Tyr Lys Glu Ala Lys Glu
```

-continued

```
                   865                 870                 875                 880
Ser Val Asp Ala Leu Phe Val Asn Ser Gln Tyr Asp Arg Leu Gln Ala
                    885                 890                 895

Asp Thr Asn Ile Ala Met Ile His Ala Ala Asp Lys Arg Val His Ser
                    900                 905                 910

Ile Arg Glu Ala Tyr Leu Pro Glu Leu Ser Val Ile Pro Gly Val Asn
                    915                 920                 925

Ala Ala Ile Phe Glu Glu Leu Glu Gly Arg Ile Phe Thr Ala Phe Ser
                930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
                965                 970                 975

Asn His Arg Ser Val Leu Val Val Pro Glu Trp Glu Ala Glu Val Ser
                980                 985                 990

Gln Glu Val Arg Val Cys Pro Gly Arg Gly Tyr Ile Leu Arg Val Thr
            995                 1000                1005

Ala Tyr Lys Glu Gly Tyr Gly Glu Gly Cys Val Thr Ile His Glu Ile
    1010                1015                1020

Glu Asn Asn Thr Asp Glu Leu Lys Phe Ser Asn Cys Val Glu Glu Glu
025                 1030                1035                1040

Val Tyr Pro Asn Asn Thr Val Thr Cys Asn Asp Tyr Thr Ala Thr Gln
                1045                1050                1055

Glu Glu Tyr Glu Gly Thr Tyr Thr Ser Arg Asn Arg Gly Tyr Asp Gly
                1060                1065                1070

Ala Tyr Glu Ser Asn Ser Ser Val Pro Ala Asp Tyr Ala Ser Ala Tyr
            1075                1080                1085

Glu Glu Lys Ala Tyr Thr Asp Gly Arg Arg Asp Asn Pro Cys Glu Ser
    1090                1095                1100

Asn Arg Gly Tyr Gly Asp Tyr Thr Pro Leu Pro Ala Gly Tyr Val Thr
105                 1110                1115                1120

Lys Glu Leu Glu Tyr Phe Pro Glu Thr Asp Lys Val Trp Ile Glu Ile
                1125                1130                1135

Gly Glu Thr Glu Gly Thr Phe Ile Val Asp Ser Val Glu Leu Leu Leu
            1140                1145                1150

Met Glu Glu
    1155

<210> SEQ ID NO 3
<211> LENGTH: 177
<212> TYPE: DNA
<213> ORGANISM: Gossypium hirsutum
<220> FEATURE:
<221> NAME/KEY: CDS
<222> LOCATION: (10)..(177)

<400> SEQUENCE: 3 ctactagca atg gct tcc tca atg atc tca tcg gct acc att gcc act gcc       51
            Met Ala Ser Ser Met Ile Ser Ser Ala Thr Ile Ala Thr Ala
                1               5                  10 tct ccg gca cag gct aac atg gtc gct cct ttc acc ggc ctc aag tct       99
Ser Pro Ala Gln Ala Asn Met Val Ala Pro Phe Thr Gly Leu Lys Ser
15                  20                  25                  30 gcc tct gct ttc cca gtc atc agg aag gcc aac aac gac att act tct      147
Ala Ser Ala Phe Pro Val Ile Arg Lys Ala Asn Asn Asp Ile Thr Ser
                35                  40                  45
```

-continued

```
ctc gca agc aat ggc ggc aga gtg caa tgc                           177
Leu Ala Ser Asn Gly Gly Arg Val Gln Cys
            50                  55

<210> SEQ ID NO 4
<211> LENGTH: 56
<212> TYPE: PRT
<213> ORGANISM: Gossypium hirsutum

<400> SEQUENCE: 4

Met Ala Ser Ser Met Ile Ser Ser Ala Thr Ile Ala Thr Ala Ser Pro
  1               5                  10                  15

Ala Gln Ala Asn Met Val Ala Pro Phe Thr Gly Leu Lys Ser Ala Ser
            20                  25                  30

Ala Phe Pro Val Ile Arg Lys Ala Asn Asn Asp Ile Thr Ser Leu Ala
        35                  40                  45

Ser Asn Gly Gly Arg Val Gln Cys
    50                  55

<210> SEQ ID NO 5
<211> LENGTH: 191
<212> TYPE: DNA
<213> ORGANISM: Gossypium hirsutum
<220> FEATURE:
<221> NAME/KEY: CDS
<222> LOCATION: (15)..(191)

<400> SEQUENCE: 5
aagcagtaat agca atg gcc tcc tcc atg atc tca tcg gca acc att gcc    50
              Met Ala Ser Ser Met Ile Ser Ser Ala Thr Ile Ala
                1               5                  10 acc gtg aac tgc tcc tcc ccg gca cag gcc aac atg gtg gcc ccc ttc    98
Thr Val Asn Cys Ser Ser Pro Ala Gln Ala Asn Met Val Ala Pro Phe
            15                  20                  25 acc ggc ctc aag tct gcc tct gct ttc cca gtc act agg aag gcc aac   146
Thr Gly Leu Lys Ser Ala Ser Ala Phe Pro Val Thr Arg Lys Ala Asn
        30                  35                  40 aac gac atc act tct ctt gca agc aat ggt ggg aga gtg caa tgc       191
Asn Asp Ile Thr Ser Leu Ala Ser Asn Gly Gly Arg Val Gln Cys
 45                  50                  55

<210> SEQ ID NO 6
<211> LENGTH: 59
<212> TYPE: PRT
<213> ORGANISM: Gossypium hirsutum

<400> SEQUENCE: 6

Met Ala Ser Ser Met Ile Ser Ser Ala Thr Ile Ala Thr Val Asn Cys
  1               5                  10                  15

Ser Ser Pro Ala Gln Ala Asn Met Val Ala Pro Phe Thr Gly Leu Lys
            20                  25                  30

Ser Ala Ser Ala Phe Pro Val Thr Arg Lys Ala Asn Asn Asp Ile Thr
        35                  40                  45

Ser Leu Ala Ser Asn Gly Gly Arg Val Gln Cys
    50                  55
```